(12) United States Patent
Yoong et al.

(10) Patent No.: US 7,582,291 B2
(45) Date of Patent: Sep. 1, 2009

(54) **BACTERIOPHAGE LYSINS FOR *ENTEROCOCCUS FAECALIS*, *ENTEROCOCCUS FAECIUM* AND OTHER BACTERIA**

(75) Inventors: Pauline Yoong, Boston, MA (US); Raymond Schuch, New York, NY (US); Daniel Nelson, New York, NY (US); Vincent A. Fischetti, West Hempstead, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 11/439,846

(22) Filed: May 24, 2006

(65) Prior Publication Data

US 2007/0025978 A1 Feb. 1, 2007

Related U.S. Application Data

(60) Provisional application No. 60/695,819, filed on Jun. 30, 2005.

(51) Int. Cl.
  *A61K 38/48* (2006.01)
  *A01N 63/00* (2006.01)
  *C12P 21/04* (2006.01)
  *C12N 9/00* (2006.01)
  *C12N 7/00* (2006.01)

(52) U.S. Cl. .................. 424/93.6; 424/94.1; 424/94.63; 435/183; 435/71.3; 435/235.1

(58) Field of Classification Search ................ 424/93.6, 424/94.1, 94.63; 435/69.1, 183
See application file for complete search history.

(56) References Cited

U.S. PATENT DOCUMENTS

| | | |
|---|---|---|
| 4,179,337 A | 12/1979 | Davis et al. |
| 4,301,144 A | 11/1981 | Iwashita et al. |
| 4,496,689 A | 1/1985 | Mitra |
| 4,615,697 A | 10/1986 | Robinson |
| 4,640,835 A | 2/1987 | Shimizu et al. |
| 4,670,417 A | 6/1987 | Iwasaki et al. |
| 4,680,338 A | 7/1987 | Sundoro |
| 4,791,192 A | 12/1988 | Nakagawa et al. |
| 4,948,580 A | 8/1990 | Browning |
| 5,413,792 A | 5/1995 | Ninomiya et al. |
| 5,554,380 A | 9/1996 | Cuca et al. |
| 5,654,010 A | 8/1997 | Johnson et al. |
| 5,808,022 A | 9/1998 | Huse |
| 5,863,560 A | 1/1999 | Osborne |
| 5,942,243 A | 8/1999 | Shah |
| 5,976,862 A | 11/1999 | Kauffman et al. |
| 6,056,954 A | 5/2000 | Fischetti et al. |
| 6,056,955 A | 5/2000 | Fischetti et al. |
| 6,132,970 A | 10/2000 | Stemmer |
| 6,783,930 B1 * | 8/2004 | Pelletier et al. ................ 435/5 |

FOREIGN PATENT DOCUMENTS

| | | |
|---|---|---|
| WO | WO 87/05330 A1 | 9/1987 |
| WO | WO 96/07399 A! | 3/1996 |
| WO | WO 96/40072 A2 | 12/1996 |
| WO | WO 97/03692 A! | 2/1997 |

OTHER PUBLICATIONS

Blast basic local alignment search tool. Sequence search of SEQ ID No. 1. p. 1-16.*

BLAST basic local alignment search tool. Sequence search of SEQ ID No. 1 carried out Sep. 17, 2007. p. 1-16.*

John D. Aplin, John C. Wriston, Jr.; Preparation, Properties, and Applications of Carbohydrate Conjugates of Proteins and Lipids;CRC Critical Reviews in Biochemistry; May 1981; pp. 259-306.

Thomas B. Broudy and Vincent A. Fischetti; In Vivo Lysogenic Conversion of Tox-*Streptococcus pyogenes* to Tox with Lysogenic Streptococci or Free Phage; American Society for Microbiology; Jul. 2003; pp. 3782-3786 vol. 71. No. 7.

Qi Cheng, Daniel Nelson, Shiwei Zhu, Vincent A. Fischetti; Removal of Group B Streptococci Colonizing the Vagina and Oropharynx of Mice with a Bacteriophoge Lytic Enzyme; American Society for Microbiology; Jan. 2005; pp. 111-117; vol. 49 No. 1.

Carol E. Chenoweth, Kristen A. Robinson, Dennis R. Schaberg; Efficacy of Ampicillin versus Trimethoprim-Sulfamethoxazole in a Mouse Model of Lethal Enterococcal Peritonitis; Sep. 1990; pp. 1800-1802; vol. 34 No. 9.

Jeffrey L. Cleland; Design and Production of Single-Immunization Vaccines Using Polylactide Polyglycolide Microsphere Systems; 1995; Vaccine Design: The Subunit and Adjuvant Approach; pp. 439-462; Plenurn Press, New York.

Vincent A. Frichetti; Novel Method to Control Pathogenic Bacteria on Human Mucous Membranes; 2003; Annals New York Academy of Sciences; pp. 207-214.

(Continued)

*Primary Examiner*—L Blaine Lankford
*Assistant Examiner*—Taeyoon Kim
(74) *Attorney, Agent, or Firm*—Brinks Hofer Gilson & Lione

(57) ABSTRACT

The present disclosure relates to bacteriophage lysins useful for the reduction of certain bacterial populations, including methods and compositions for the treatment of various bacterial infections. For example, bacteriophage lysins were isolated and shown to effectively kill various bacteria, including both *E. faecalis* and *E. faecium* (including vancomycin resistant strains), as well as other human pathogens.

27 Claims, 17 Drawing Sheets

OTHER PUBLICATIONS

Vincent A. Fischetti; Phage antibacterials make a comeback; Nature Publishing Group; Aug. 2001; pp. 734-735; vol. 19.

Sastry V. S. Gollapudi, Alok Gupta, Haragopal Thadepalli, Angel Perez; Use of Lymphokines in Treatment of Experimental Intra-Abdominal Abscess Caused by *Bacteroides fragilis*; American Society for Microbiology Infection and Immunity; Sep. 1988; pp. 2369-2372.

Carlos A. Guzmán, Carla Pruzzo, Maurizio Platé, Maria C. Guardati, Letizia Calegari; Serum dependent expression of *Enterococcus faecalis*; adhesions involved in the colonization of heart cells; Microbial Pathogenesis; 1991; pp. 399-409.

Stephan Harbarth, Sara Cosgrove, Yehuda Carmeli;Effects of Antibiotics on Nosocomial Epidemiology of Vancomycin-Resistant Enterococci; American Society for Mircobiology, Antimicrobial Agents and Chemotherapy; Jun. 2002; pp. 1619-1628; vol. 46, No. 6.

Maninder Singh Hora, Rajsharan K. Rana, Jack H. Numberg, Thomas R. Tice, Richard M. Gilley, Michael E. Hudson; Controlled Release of Interleukin-2 from Biodegradable Microspheres; Nature Publishing Group; Aug. 1990; pp. 755-799; vol. 8.

Olufunmi L. Johnson, Jeffrey L. Cleland, Hye Jung Lee, Margarita Charnis Eileen Duenas, Warren Jaworowicz, Douglas Shepard, Azin Shahzamani, Andrew J.S. Jones, Scott D. Putney; A month-long effect from a single injection of microencapsulated human growth hormone; Nature Publishing Group; Jul. 1996; pp. 795-799; vol. 2, No. 7.

James F. Kane; Effects of rare codon clusters on high-level expression of heterologous proteins in *Escherichia coli*; Current Biology Ltd. Current Opinion in Biotechnology; 1995 pp. 6:494-500.

Theresa M. Koehler; *Bacillus anthracis*; American Society for Microbiology;2000; pp. 54: 519-528.

Jutta M. Loeffler, Svetolik Djurkovic, Vincent A. Fischetti; Phage Lytic Enzymen Cpl-1 as a Novel Antimicrobial for Pneumococcal Bacteremia; American Society for Microbiology; Infection and Immunity; Nov. 2003; pp. 6199-6204; vol. 71, No. 11.

Jutta M. Loeffler, Daniel Nelson, Vincent A. Fischetti; Rapid Killing of *Streptococcus pneumoniae* with a Bacteriophage Cell Wall Hydrolase; Science; Dec. 7, 2001; pp. 2170-2172; vol. 294.

Martin J. Loessner, Susanne Gaeng, Siegfried Scherer;American Society for Mocrobiology, Journal of Bacteriology; Aug. 1999; pp. 4452-4460; vol. 181, No. 15.

Martin J. Loessner, Günther Wendlinger, Siegfried Scherer; Hetergeneous enddolysins in *Listeria monocytogenes* bacteriophages: a new class of enzymes and evidence for conserved holin genes within the siphoviral lysis cassettes; Blackwell Science Ltd., Molecular Microbiology; Mar. 1995; pp. 16(6): 1231-1241.

Martin J. Loessner, Simon K. Maier, Helmut Daubek-Puza, Günther Vendlinger, Siegfried Scherer; Three *Bacillus cereus* Bacteriophage Endolysins Are Unrelated but Reveal High Homology to Cell Wall Hydrolases from Different Bacilli; American Society for Microbiology, Journal of Bacteriology; May 1997; pp. 2845-2851; vol. 179, No. 9.

Rubens López, María P. González, Ernesto García, Pedro García; Biological roles of two new murein hydrolases of *Stretococcus pneumoniae* representing examples of module shuffling; Res. Microbiol.; 2000; pp. 437-443.

Rubens López, Ernesto García, Pedro García, José Luīs García; The Pneumococcal Cell Wall Degrading Enzymes: A Modular Design to Create New Lysins?; Microbial Drug Resistance; 1997; pp. 199-211; vol. 3 No. 2.

Daniel Nelson; Lawrence Loomis; Vincent A. Fischetti; Prevention and Elimination of Upper Respiratory Colonization of Mice by Group A Streptococci by Using a Bacteriophage Lytic Enzyme; Proceedings of the National Academy of Sciences of the United States of America; J STOR; Mar. 27, 2001; pp. 4107-4112; vol. 98, No. 7.

Vijaykumar Pancholi, Vincent A. Fischetti; Isolation and Characterization of the Cell-Associated Region of Group A Streptococcal M6 Protein; American Society for Microbiology, Journal of Bacteriology; Jun. 1998; pp. 2618-2624; vol. 170, No. 6.

Raymond Schuch, Daniel Nelson, Vincent A. Fishetti; A bacteriolytic agent that detects and kill *Bacillus anthracis*; Nature Publishing Group, letters to nature; Aug. 22, 2002; pp. 884-889; vol. 418.

Michelle M. Sheehan, José L. García, Rubens López, Pedro García; The lytic enzyme of the pneumococcal phage Dp-1; a chimeric lysine of intergeneric origin; Blackwell Science, Molecular Microbiology; Jun. 1995; pp. 25(4), 717-725.

Kavindra V. Singh, Teresa M. Coque, George M. Weinstock, Barbara E. Murray; In vivo testing of an *Enterococcus faecalis eraA* mutant and use of *efaA* homologs for species identification; FEMS Immunology and Medical Microbiology, Elsevier; 1998; pp. (21) 323-331.

Kavindra V. Singh, Xiang Qin, George M. Weinstock. Barbara E. Murray; Generation and Testing of Mutants of *Enterococcus faecalis* in a Mouse Peritonitis Mode; The Journal of Infectious Diseases; 1998; pp. 178: 1416-1420.

Claudia Gentry-Weeks, Monica Estay, Cindy Loui, Dale Baker; Intravenous Mouse Infection Model for Studying the Pathology of *Enterococcus faecalis* Infections; American Society for Microbiology, Infection and Immunity; Mar. 2003; pp. 1434-1441; vol. 71, No. 3.

Yesim Centinkaya, Pamela Falk, C. Glen Mayhall; Vancomycin-Resistant Enterococci; American Society for Microbiology, Clinical Microbiology Reviews; Oct. 2000; pp. 686-707; vol. 13, No. 4.

Pauline Yoong, Raymond Schuch, Daniel Nelson, Vincent A. Fischetti; PlyPH, a Bacteriolytic Enzyme with a Broad pH Range of Activity and Lytic Action against *Bacillus anthracis*; American Society for Microbiology, Journal of Bacteriology; Apr. 2006; pp. 2711-2714; vol. 188, No. 7.

Pauline Yoong, Raymond Schuch, Daniel Nelson, Vincent A. Fischetti; Identification of a Broadly Active Phage Lytic Enzyme with Lethal Activity against Antibiotic-Resistant *Enterococcus faecalis* and *Enterococcus faecium*; American Society for Microbiology, Journal of Bacteriology; Jul 2004 pp. 4808-4812; vol. 186, No. 14.

Ry Young; Bacteriophage Lysis; Mechanism and Regulation; American Society for Microbiology, Mircobiological Reviews; Sep. 1992; pp. 430-481; vol. 56, No. 3.

Ry Young, Ing-Nang Wang, William D. Roof; Phages will out: strategies of host cell lysis; Trends in Microbiology, Reviews; Mar. 2000; pp. 120-128; vol. 8, No. 3.

\* cited by examiner

FIGURE 1

SEQ ID NO:1 PlyV12

MTRRYTKMNVPQSLVNWFVNHRNLLTYSMYGSRNGSDGTADCSGSMSQALKEAGIPIQGLPSTVTLGQQLAKNGFYR
ISRNEDWNAETGDIVLMSWGADMASSGGAGGHVGVMMDSVNFISCDYSTQGAAGQAINTYPWNDYYEANKPAYIEVW
RYSESAPQTKNQANTAVTPQQKAYYEANEVKYVNGIWQIKCDYLSPIGFDYLENGIPVTMVNWVDKDGNDLPDGADQ
DLKAGMYFSFSSDETNIVDTGNGGYYGGYYWRLFEFGQFGPVWLSCWNKDDLVNYFQ

FIGURE 2

```
Sa     1   -----MELNTEIAIAWMSARQGK-VSYSMDY-RDGPN-SYDCSSSMYYALRSAGASSAGW
Spy    1   -----MTVLTEKAIAWMGLKEGR-VSYSMDY-RNGPD-SYDCSSAICSALIYAGASNPGW
Spn    1   -----MGVDIEKGVAWMQARKGR-VSYSMDF-RDGPD-SYDCSSSMYYALRSAGASSAGW
Sm     1   -----MGLNLETAIAWMRARKGQ-VSYSMDD-RNGPD-SYDCSSSHYYALLSGGAVSAGW
Ef     1   ----MSNINMETAIANMYALKARGITYSMNYSRTGADGTADCSGTVYDSLRKAGASDAGW
PlyV12 1   MTRRYTKMNMPQSLVNWFVNHRNLLTYSMYGSRNGSDGTADCSGSMSQALKEAGIPIQGL
                                                   DCSG       A
                                                      *

Sa     53  AVNTEYMHDWLIKNGMELIAENVDWNAVRGDIAIWGM---RGHSSGAGGHVVMFIDPENI
Spy    53  LLNTEYMHDWLMQNGFELIAENEDWDSQRADIAIWGL---RGQSAGAGGHVVMFIDADNI
Spn    53  AVNTEYMHAWLFENGMELISENAPWDAKRGDIFIWGR---RGASAGAGGHTCMFIDSDNI
Sm     53  AVNTEYEHDWLKKNGFELIAENTPWDAQRGDIFIWGC---RGYSSGAGGHTGLFYDSDNI
Ef     57  VLNTDSMHSWLEKNGFKLIAQNKEWSAKRGDVVIEGK---KGASGGSAGHVVLFISSTQI
PlyV12 61  PS-TVTTGQQLAKNGFYRISRNEDWNAETGDTVLMSWGADMASSGGAGGHVGWMMDSVNF
                                 GD V F      GS GHV I I     Q

Sa     110 IHCNWANNGIT-VNNYNQTAAASGWMYCYVYRLKSGASTQGKSLDTLVKETLAGNYGNGE
Spy    110 IHCNYANNNIT-IDNYNQTAAASGWMYSYAYRYN--------------------------
Spn    110 IHCNYAYDGIS-VNDHERWYYAGQPYMYVYRLT--------------------------
Sm     110 IHCNYRFDGIT-VNDHDDIWLYAGRPYMYVYRLT--------------------------
Ef     114 IHCTAKSATANGVYVDNEATTCPYSMGWYVYRLN--------------------------
PlyV12 120 ISCDYSTQGAA-------GQAINTYPWNDYYEAN--------------------------
           IH

Sa     169 ARKAVLGNQYEAVMSVINGKTTTNQKTVDQLVQEVIAGKHGNGEARKKSLGSQYDAVQKR
Spy    143 -----G----E---------QSQPTNKSIDELAQEVLAGKHGSGEQRKLSLCSNYDAVQAK
Spn    143 -------------------------NANAQ-PAEKKEGWQKDATGFWYAPANG-TYPKDEFE
Sm     143 -------------------------NPSAA-AEEIKTGWQNDDTGYWFVRANG-SYPKDQFE
Ef     148 -------------------------GGSTPPKPNTKKVKVLKHATNWSPSSKGAKMASFVKGG
PlyV12 147 -------------------------KPAYIEVWRYSESAPQTKNQANT-AVTPQQKA

Sa     229 VTELLKKQPSEPFKAQEVNKPTETKTSQTELTGQATATKEEGDLSFNGTILKKAVLDKIL
Spy    186 VNEMLK---------------------QPQVAEQSPAVKQDGDLLFNGAVLKKAILDKIL
Spn    178 YIEENK------------------------------------------------------
Sm     178 YIEENK------------------------------------------------------
Ef     186 TFNVKQ------------------------------------------------------
PlyV12 178 YYEANE------------------------------------------------------

Sa     289 GNCKKHDILPSYALTILHYEGLWGTSAVGKADNNWGGMTWTGQGNRPSGVTVTQGSARPS
Spy    225 AKCKEHDILPSYAITVLHFEGLWGQSAVGRADNNWGGMTWTGQGNRPSGITVTQGTERPA
Spn    184 --------------S-WFYFLDQGYMLAEKWLKHTDGNWYWFDR-DG-------------
Sm     184 --------------S-WFYFDANGYMVAEDWVKHTDGKWYWFDK-DG-------------
Ef     192 ----------------QRPISYSYSNQEYLIVNKGTVLGWVLSQDIEGG-----------
PlyV12 184 ----------------VKYVNGIFQIKCDYLSPIGFDYLENGIPVT--------------

Sa     349 NEGGHYMFYASVDDFLTDWFYLLRAGGSYKVSGAKTFSEAIKGMFKVGGAVYDYAASGED
Spy    285 VEGGHYMFYASVDDFLTDWFYLLRADGSYRISGAKTFSEAVKGMFKVGGATYDYAASGYD
Spn    215 ------YMATSWKRIGESWYYFNRDGSMVTGWIKYMENWYYCDATNG----DMKSNAFI
Sm     215 ------YMATSWKKINGKWYYFNRDGSMQTGWVKYYEKWYYLNSENG----DMVSNAEV
Ef     225 ---YGSDRVGGSKPKLPAGETKEEATFINGNAPITTRKNKPSLSSQTATPLYPGQSVRFL
PlyV12 214 -------MVNWVDKDGNDLPDGADQDLKAGMYFSFSSDETNIVDTGNG------------

Sa     409 SYIVGASSRLKAIEAENGSLDKFDKATDIGDGSKFKIDFTIEGLEVTINGITYELTKKPV
Spy    345 NYIVGMSSRLKAIEQENGPINKYDQQTDISVGQSDKIDVVIDSIEITINGVTYTATKKPI
Spn    264 RYNDG--------------MYLILPDGRLADKPQFTVEPDGLITAKV------------
Sm     264 PYNGC--------------MYLMLEDGRLAEKESFNLEPDGLITTK-------------
Ef     282 GLKSAEG-------------YIFIYATDGRYIPVRPMGKEAWGTFK-------------
PlyV12 255 GLYGG---------------YYWRLFEFGQFGPVWLSCWNKDDLVNYFQ-----------
```

FIGURE 12A

A        Mouse 1   Mouse 2   Mouse 3   Mouse 4   Mouse 5
         -14.51    -24.06    -14.51    -14.29    -12.10

```
                        SEQUENCE LISTING

<160> NUMBER OF SEQ ID NOS: 1

<210> SEQ ID NO 1
<211> LENGTH: 288
<212> TYPE: PRT
<213> ORGANISM: Enterococcal Bacteriophage pji-1

<400> SEQUENCE: 1

Met Thr Arg Arg Tyr Thr Lys Met Asn Val Pro Gln Ser Leu Val Asn
1               5                   10                  15

Trp Phe Val Asn His Arg Asn Leu Leu Thr Tyr Ser Met Tyr Gly Ser
            20                  25                  30

Arg Asn Gly Ser Asp Gly Thr Ala Asp Cys Ser Gly Ser Met Ser Gln
        35                  40                  45

Ala Leu Lys Glu Ala Gly Ile Pro Ile Gln Gly Leu Pro Ser Thr Val
    50                  55                  60

Thr Leu Gly Gln Gln Leu Ala Lys Asn Gly Phe Tyr Arg Ile Ser Arg
65                  70                  75                  80

Asn Glu Asp Trp Asn Ala Glu Thr Gly Asp Ile Val Leu Met Ser Trp
                85                  90                  95

Gly Ala Asp Met Ala Ser Ser Gly Gly Ala Gly Gly His Val Gly Val
            100                 105                 110

Met Met Asp Ser Val Asn Phe Ile Ser Cys Asp Tyr Ser Thr Gln Gly
        115                 120                 125

Ala Ala Gly Gln Ala Ile Asn Thr Tyr Pro Trp Asn Asp Tyr Tyr Glu
    130                 135                 140

Ala Asn Lys Pro Ala Tyr Ile Glu Val Trp Arg Tyr Ser Glu Ser Ala
145                 150                 155                 160

Pro Gln Thr Lys Asn Gln Ala Asn Thr Ala Val Thr Pro Gln Gln Lys
                165                 170                 175

Ala Tyr Tyr Glu Ala Asn Glu Val Lys Tyr Val Asn Gly Ile Trp Gln
            180                 185                 190

Ile Lys Cys Asp Tyr Leu Ser Pro Ile Gly Phe Asp Tyr Leu Glu Asn
        195                 200                 205

Gly Ile Pro Val Thr Met Val Asn Trp Val Asp Lys Asp Gly Asn Asp
    210                 215                 220

Leu Pro Asp Gly Ala Asp Gln Asp Leu Lys Ala Gly Met Tyr Phe Ser
225                 230                 235                 240

Phe Ser Ser Asp Glu Thr Asn Ile Val Asp Thr Gly Asn Gly Gly Tyr
                245                 250                 255
```

```
Tyr Gly Gly Tyr Tyr Trp Arg Leu Phe Glu Phe Gly Gln Phe Gly Pro
            260                 265                 270

Val Trp Leu Ser Cys Trp Asn Lys Asp Asp Leu Val Asn Tyr Phe Gln
        275                 280                 285
```

BACTERIOPHAGE LYSINS FOR *ENTEROCOCCUS FAECALIS*, *ENTEROCOCCUS FAECIUM* AND OTHER BACTERIA

RELATED APPLICATIONS

This application claims the benefit to U.S. provisional patent application Ser. No. 60/695,819, entitled "BACTERIOPHAGE LYSINS FOR *ENTEROCOCCUS FAECALIS, ENTEROCOCCUS FAECIUM* AND OTHER BACTERIA," filed Jun. 30, 2005 by Yoong, et al., which is hereby incorporated by reference in its entirety.

TECHNICAL FIELD

The present disclosure relates to the identification and use of phage associated lytic enzymes to rapidly and specifically detect and kill *Enterococci* bacteria and certain other bacteria, including certain antibiotic-resistant *Enterococcus faecalis* and *Enterococcus faecium* strains.

BACKGROUND

*Enterococcus faecalis* and *Enterococcus faecium* are gram-positive bacteria that commensally colonize the lower intestinal tract, oral cavity and vaginal tract of humans. In healthy individuals, *E. faecalis* and *E. faecium* colonization normally has no adverse effect on the host. However, the incidence of enterococcal infections has increased and since the 1970s and 1980s, *enterococci* have become major nosocomial pathogens. Enterococcal infections are mostly hospital-acquired though they are also associated with some community-acquired infections. Recent evidence suggests that *E. faecium* can be spread by direct contact with other infected patients, indirect transmission from hospital personnel (J M Boyce et al., 1994, J Clin Microbiol 32:1148; and E. Rhineheart et al., 1990, N Engl J Med 323:1814), or from contaminated hospital surfaces and equipment (L V Karanfil et al., 1992, Infect Control Hosp Epidemiol 13:195; and J M Boyce et al., 1994, J Clin Microbiol 32:1148; and L L Livomese Jr., 1992, Ann Intern Med 117:112). Of nosocomial infections *enterococci* account for 12% of bacteremia, 15% of surgical wound infections, 14% of urinary tract infections, and 5 to 15% of endocarditis cases (Huycke, M. M., D. F., Sahm and M. S. Gilmore. 1998. Emerging Infectious Diseases 4:239-249). Additionally *enterococci* are frequently associated with intraabdominal and pelvic infections. They are now the fourth leading cause of hospital-acquired infection and the third leading cause of bacteremia in the United States. Fatality ratios for enterococcal bactermia range from 12% to 68%, with death due to enterococcal sepsis in 4 to 50% of these cases. See T. G. Emori (1993) Clin. Microbiol. Rev. 6:428-442. *Enterococcus faecalis* or *E. faecalis* is the most common pathogen in the group of these pathogens, accounting for 80-90 percent of all enterococcal infections. See Lewis et al. (1990) Eur J. Clin Microbiol Infect Dis. 9:111-117.

Enterococcal infection is of particular concern because of the emergence of bacteria that are resistant to antibiotics such as aminoglycosides, penicillin, ampicillin and vancomycin. The acquisition of virulence factors and high-level antibiotic resistance by *enterococci* are causing these organisms to emerge as a leading source of nosocomial infections, particularly in immunocompromised patients. The development of multiple-drug resistant (MDR) *enterococci* has made enterococcal bacteria a major concern. For example, *E. faecium* is a prominent cause of infection in humans, with high levels of multidrug resistance (A. Kaufhold and R. Klein (1995) Zentralblatt fuer Bakteriologie 282 507). Antimicrobial resistance can be divided into two general types, 1) inherent or intrinsic resistance and 2) acquired resistance. The genes for intrinsic resistance, like other species characteristics, appear to reside on the chromosome. Acquired resistance results from either a mutation in the existing DNA or acquisition of new DNA. The various inherent traits expressed by enterococci include resistance to semisynthetic penicillinase-resistant penicillins, cephalosporins, low levels of aminoglycosides, and low levels of clindamycin. Examples of acquired resistance include resistance to chloramphenicol, erythromycin, high levels of clindamycin, tetracycline, high levels of aminoglycosides, penicillin by means of penicillinase, fluoroquinolones, and vancomycin. Resistance to high levels of penicillin without penicillinase and resistance to fluoroquinolones are not known to be plasmid or transposon mediated and presumably are due to mutation(s).

One promising approach to the detection and treatment of pathogenic gram positive bacteria is the use of bacteriophage lytic enzymes as bacteriolytic agents. Bacteriophage lytic enzymes responsible for bacterial host lysis are also known as lysins. Many lysins can rapidly break down the bacterial cell wall in order to release progeny phage (Young, R. 1992. Bacteriophage lysis: mechanism and regulation. Microbiol. Rev. 56:430-481). Structurally, lysins are commonly found as modular proteins with an amino terminal domain that confers the enzymatic activity for a peptidoglycan bond and a carboxy terminal domain that confers binding specificity to a carbohydrate epitope in the bacterial cell wall (Loessner, M., K. Kramer, F. Ebel, and S. Scherer. 2002). C-terminal domains of Listeria monocytogenes bacteriophage murein hydrolases determine specific recognition and high-affinity binding to bacterial cell wall carbohydrates. (Mol. Microbiol. 44:335-349; Lopez, R., E. Garcia, P. Garcia, and J. L. Garcia. 1997). The pneumococcal cell wall degrading enzymes: a modular design to create new lysins? (Micro*B*. Drug Resist. 3:199-211; Lopez, R., M. P. Gonzalez, E. Garcia, J. L. Garcia, and P. Garcia. 2000). Biological roles of two new murein hydrolases of *Streptococcus pneumoniae* representing examples of module shuffling. (Res. Microbiol. 151:437-443; Sheehan, M. M., J. L. Garcia, R. Lopez, and P. Garcia. 1997). The lytic enzyme of the pnemococcal phage Dp-1: a chimeric enzyme of intergeneric origin. (Mol. Microbiol. 25:717-725). Lysins are believed to provide at least one of the following enzymatic activities against a peptidoglycan substrate: muramidases, glucosaminidases, N-acetylmuramyl-L-alanine amidase and endopeptidases (Young, R. 1992. Bacteriophage lysis: mechanism and regulation. Microbiol. Rev. 56:430-481). Purified lysin from a bacteriophage can be applied exogenously to affect bacterial lysis (Loeffler, J. M., D. Nelson, and V. A. Fischetti. 2001. Rapid killing of *Streptococcus pneumoniae* with a bacteriophage cell wall hydrolase. Science. 294:2170-2172; Loessner, M., G. Wendlinger, and S. Scherer. 1995). Heterogeneous endolysins in *Listeria monocytogenes* bacteriophages: a new class of enzymes and evidence for conserved holin genes within the siphoviral lysis cassettes. (Mol. Microbiol. 16:1231-1241; Loessner, M., S. K. Maier, H. Daubek-Puza, G. Wendlinger, and S. Scherer. 1997). Three *Bacillus cereus* bacteriophage endolysins are unrelated but reveal high homology to cell wall hydrolases from different bacilli. (J. Bacteriol. 179:2845-2851; Nelson, D., L. Loomis, and V. A. Fischetti. 2001). Prevention and elimination of upper respiratory colonization of mice by group A *streptococci* by using a bacteriophage lytic enzyme. Prot. Natl. Acad. Sci. USA. 98:4107-4112).

Lysins are normally very specific to the bacterial species from which the lysin derived phage was isolated (Fischetti, V. A. 2003. Novel method to control pathogenic bacteria on human mucous membranes. Ann. N.Y. Acad. Sci. 987:207-214; Fischetti, V. A. 2001. Phage antibacterials make a comeback. Nature Biotechnol. 19:734-735). Although the range of bacteria targeted by lysins is less restrictive than the corresponding bacteriophage, lysins still maintain a degree of specificity, having minimal effects on other bacteria including commensal organisms. While bacteriophage host ranges are largely restrictive, recognizing only one specific antigen on its bacterial host, phage lysins are less restrictive, recognizing a specific carbohydrate molecule common to the particular species of host bacteria.

Bacterial resistance to phage lysins is believed to be less likely to arise as compared with bacteriophage adsorption. Bacterial lysis upon exposure to lysin is almost immediate, not giving bacteria much possibility for mutation and secondly, because lysins bind to highly conserved molecules in the bacterial cell wall that are under selective pressure not to mutate. This is evidenced by the lysins from *S. pneumoniae* phages binding to choline, an essential component on the *S. pneumoniae* cell wall, and a lysin, PlyC, targeting *S. pyogenes* by specifically binding the alternating ($\alpha 1 \rightarrow 2$) and ($\alpha 1 \rightarrow 3$) linked polyrhamnose backbone of surface carbohydrates. The exposure of bacteria to subinhibitory lysin concentrations and mutagenesis studies have not identified bacteria that are resistant to the action of phage lysins (Schuch, R., D. Nelson, and V. A. Fischetti. 2002. A bacteriolytic agent that detects and kills *Bacillus anthracis*," Nature, 418:884-888). In contrast, bacterial resistance to many antibiotics are easily identified using the techniques used above. Furthermore, the problem with lysogenic conversion is completely eliminated with phage lysins, and animal testing have determined lysins to be safe.

There is an ongoing need for therapies and agents effective in the diagnosis and control of bacterial contamination, colonization and infection. In addition, compounds with bacteriocidal effects may be useful in the decontamination of bacteria on inanimate surfaces and objects. The bactiophage lytic enzymes provided herein are useful in providing agents useful in the detection, treatment and decontamination of gram-positive bacteria, including *Enterococci* bacteria.

SUMMARY

This invention relates to approaches to control and treat certain gram positive bacteria, including Enterococcal bacteria, using lytic enzymes obtained from bacterial viruses, known as bacteriophages, which can be used to break down the bacterial cell wall of target bacteria, such as *Enterococci faecalis* and *Enterococcus faecium* bacteria. The bacteriophage lytic enzymes are naturally produced during the lytic life cycle of bacteriophages which occurs in the bacterial cytoplasm. The end of this cycle results in the production of a lytic enzyme that lyses the bacteria to release the viral progeny. The lytic enzyme, termed a lysin, can be purified from the lysate or produced recombindantly. Administration of small quantities of lytic enzymes to Gram-positive bacteria may cause a rapid lysis and death of the Gram-positive bacterial organism. Particularly preferred lysins are described in Yoong P, Schuch R, Nelson D, Fischetti V A, "Identification of a broadly active phage lytic enzyme with lethal activity against antibiotic-resistant *Enterococcus faecalis* and *Enterococcus faecium*," J Bacteriol. July; 186(14):4808-12 (2004), which is incorporated herein by reference in its entirety.

Bacteriophage lytic agents effective against certain gram positive bacteria, including certain *Enterococci* bacteria, are provided, along with corresponding polypeptide and polynucleotide sequences relating to the same. Compositions comprising the lytic enzymes, as provided, are useful in the diagnosis, treatment, and decontamination applications relating to several types of gram positive bacteria, as described herein, including certain *Enterococci* bacteria. Also provided are methods of treatment and decontamination using compositions comprising the lytic enzymes, polypeptides or polynucleotide sequences disclosed here.

Lysins exhibiting a lytic effect on one or more gram positive bacterial strains are provided herein. Preferably, the lysins have killing activity against one or more *Enterococci* bacterial species. In one aspect, lysins are provided that exhibit a lytic effect against the *E. faecalis* strain V12. Also provided are lysins with killing activity against vancomycin resistant strains of *E. faecalis* and strains of the closely related enterococcal pathogen, *E. faecium*. Methods and compositions relating to the diagnosis and treatment of gram positive bacteria, including *Enterococcus* bacteria, infection or colonization are also provided.

Preferably, the lysins comprise a polypeptide sequence having at least 80%, 95%, 90%, 95%, 96%, 97%, 98%, 99% or greater homology to SEQ ID NO:1. Also preferably, the lysins can be obtained from the enterococcal bacteriophage $\phi 1$ which infects the host *E. faecalis* strain V12. Preferably, lysins provided herein have at least 80% homology to SEQ ID NO:1 and killing activity against two or more gram positive bacterial strains. In one aspect, the lysin exhibits a lytic effect on multiple gram positive bacterial strains, including multiple *E. faecalis* strains. Preferably, the lysin also lyses vancomycin resistant strains of *E. faecalis* and strains of the closely related enterococcal pathogen, *E. faecium*. Lysins having lethal activity against one or more other bacterial pathogens such as *Staphylococcus aureus*, *S. pyogenes*, groups B, C, E and G *streptococci* are also provided herein.

In one aspect, a direct viability assay performed by incubating a lysin provided herein with *E. faecalis* strain V12 results in at least a 1-, 2-, 3- or 4-log reduction in viability when the *E. faecalis* strain is exposed to 25 units/mL of the lysin for 15 minutes, or a decrease of 200 milliunits of $OD_{600}$ per minute ($mOD_{600}/min$) in the optical density assay. In another particular aspect, the lysins provided exhibit lytic activity against *E. faecalis* strain V12 bacteria, as measured by at least a 20% decrease in $OD_{600}$ in 15 minutes, over a pH range of about 5.0 to 8.0, preferably about 5.0 to 7.5, and most preferably at about 6.0 to 7.5. Preferably, the lysins provided exhibit lytic activity against *E. faecalis* strain V12 bacteria, as measured by at least a 25% decrease in $OD_{600}$ after 15 minutes, at a pH of about 5.0 to about 8.0, more preferably at least a 40% decrease in $OD_{600}$ after 15 minutes, at a pH of about 5.0 to about 7.5, more preferably at least a 50% decrease in $OD_{600}$ after 15 minutes, at a pH of about 5.0 to about 7.0, more preferably at least a 60% decrease in $OD_{600}$ after 15 minutes, at a pH of about 5.0 to about 6.5, more preferably at least a 40%, 50%, 60%, 65% or 70% decrease in $OD_{600}$ after 15 minutes, at a pH of about 6.0.

BRIEF DESCRIPTION OF THE DRAWINGS

FIG. 1 shows the polypeptide sequence for PlyV12 (SEQ ID NO:1), a particularly preferred bacteriophage lysin for *Enterococci* bacteria.

FIG. 2 shows an alignment of the amino acid sequence of PlyV12 from *E. faecalis* bacteriophage $\phi 1$ (Ef) with lysins from five other Gram-positive bacteriophages.

FIG. 12A FIG. 12A shows the changes in $OD_{600}$ over a 20 minute period of endogenous enterococci isolated from fecal samples of five BALB/c mice to PlyV12.

DETAILED DESCRIPTION

Definitions

Figure 3:
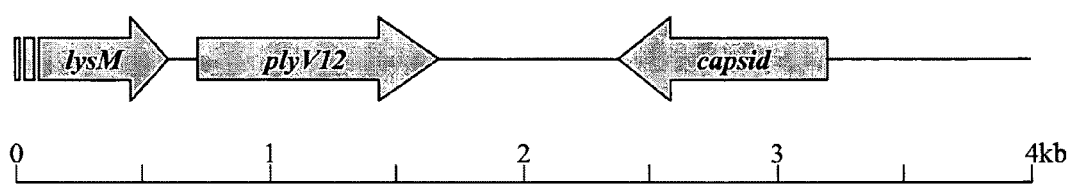
FIG. 3 is a schematic showing the locations and orientation of the ORFs identified from 4 kb of sequenced phage φ1 DNA.

Unless otherwise indicated, the certain terms used herein and their applicability to the present disclosure are defined below.

The term "isolated" means at least partially purified from a starting material. The term "purified" means that the biological material has been measurably increased in concentration by any purification process, including by not limited to, column chromatography, HPLC, precipitation, electrophoresis, etc., thereby partially, substantially or completely removing impurities such as precursors or other chemicals involved in preparing the material. Hence, material that is homogenous or substantially homogenous (e.g., yields a single protein signal in a separation procedure such as electrophoresis or chromatography) is included within the meanings of isolated and purified. Skilled artisans will appreciated that the amount of purification necessary will depend upon the use of the material. For example, compositions intended for administration to humans ordinarily must be highly purified in accordance with regulatory standards.

The term "lytic enzyme genetically coded for by a bacteriophage" refers to a polypeptide having at least some lytic activity against the host bacteria.

"Polypeptide" refers to a molecule comprised of amino acids which correspond to polypeptides encoded by a polynucleotide sequence which is naturally occurring. The polypeptide may include conservative substitutions where the naturally occurring amino acid is replaced by one having similar properties, where such conservative substitutions do not alter the function of the polypeptide (see, for example, Lewin "Genes V" Oxford University Press Chapter 1, pp. 9-13 1994).

"A native sequence phage associated lytic enzyme" refers to a polypeptide having the same amino acid sequence as an enzyme derived from nature. Such native sequence enzyme can be isolated from nature or can be produced by recombinant or synthetic means. The term "native sequence enzyme" specifically encompasses naturally occurring forms (e.g., alternatively spliced or modified forms) and naturally-occurring variants of the enzyme. In one example, the native sequence enzyme is a mature or full-length polypeptide that is genetically coded for by a gene from a bacteriophage specific for E. faecalis V12.

The term "effective amount" refers to an amount of an active ingredient sufficient to achieve a desired effect without causing an undesirable side effect. In some cases, it may be necessary to achieve a balance between obtaining a desired effect and limiting the severity of an undesired effect. The amount of active ingredient used will vary depending upon the type of active ingredient and the intended use of the composition of the present invention.

A "variant polypeptide sequence phage associated lytic enzyme" means a functionally active lytic enzyme genetically coded for by a bacteriophage specific for E. faecalis V12 having at least 50%, 55%, 60%, 65%, 70%, 75%, 80%, 85%, 90%, 95%, 97%, 98%, 99%, or even at least 99.5% amino acid sequence identity with a sequence described herein.

"Percent (%) polypeptide sequence identity" with respect to the lytic enzyme polypeptide sequences identified here is defined as the percentage of amino acid residues in a candidate sequence that are identical with the amino acid residues in the specific lytic enzyme polypeptide sequence, after aligning the sequences and introducing gaps, if necessary, to achieve the maximum percent sequence identity, and not considering any conservative substitutions as part of the sequence identity. Methods for alignment for purposes of determining percent amino acid sequence identity are described below.

Enterococcal Lysins

Bacteriophage lysins with killing activity against Enterococci bacteria and other gram positive bacteria are provided. Preferred bacteriophage lysins, including the PlyV12 lysin and variants thereof, provide killing activity against Enterococci bacteria, are identified and characterized in a series of exemplary embodiments described below. Other embodiments provide lysins with specific activity against other gram positive bacteria, which include variants and fragments of the lysins described herein. Particularly preferred lysins with killing activity against antibiotic resistant *E. faecalis* and *E. faecium* strains.

Lysins generally occur in a modular structure. The N-terminal module consists of a catalytic domain believed to possess the ability to break down the bacterial cell wall of certain bacteria. Ezymatic activities often associated with the catalytic domain are amidases, endopeptidases, glucosamidases and muramidases. The C-terminal module consists of a binding domain that is believed to have an affinity for a carbohydrate epitope on the target bacteria cell wall. The binding domain is believed to determine the specificity of the lysin.

Bacteriophage lytic agents effective against certain gram positive bacteria, including certain *Enterococci* bacteria, are provided, along with corresponding polypeptide and polynucleotide sequences relating to the same. Compositions comprising the lytic enzymes provided may be useful in the diagnosis, treatment, and decontamination applications relating to several types of gram positive bacteria, as described herein, including certain *Enterococci* bacteria. Methods of treatment and decontamination using compositions comprising the lytic enzymes, polypeptides or polynucleotide sequences are also disclosed.

Lysins exhibiting a lytic effect on one or more gram positive bacterial strains are provided herein. Preferably, the lysins have killing activity against one or more *Enterococci* bacterial species. In one aspect, lysins that exhibit a lytic effect against the *E. faecalis* strain V12 are provided. Lysins with killing activity against vancomycin resistant strains of *E. faecalis* and strains of the closely related enterococcal pathogen, *E. faecium* are also provided.

Preferably, the lysins comprise a polypeptide sequence having at least 80%, 85%, 90%, 95%, 96%, 97%, 98%, 99% or greater homology to SEQ ID NO:1. Also preferably, the lysins can be obtained from the enterococcal bacteriophage φ1 which infects the host *E. faecalis* strain V12. Lysins provided here have at least 80% homology to SEQ ID NO:1 and killing activity against two or more gram positive bacterial strains. In one example, the lysin exhibits a lytic effect on multiple gram positive bacterial strains, including multiple *E. faecalis* strains. The lysin also lyses vancomycin resistant strains of *E. faecalis* and strains of the closely related enterococcal pathogen, *E. faecium*. The lysins may also have lethal activity against one or more other bacterial pathogens such as *Staphylococcus aureus, S. pyogenes*, groups B, C, E and G streptococci.

The following references relating to the therapeutic application of lytic enzymes as an antibacterial agent are incorporated herein by reference in their entirety: Broudy, T. B., and V. A. Fischetti, "In vivo lysogenic conversion of Tox– *Streptococcus pyogenes* to Tox+ with lysogenic *streptococci* or free phage," *Infect. Immun.* 71, pp. 3782-3786 (2003); Cheng, Q., D. Nelson, S. Zhu, and V. A. Fischetti, "Removal of group B *streptococci* colonizing the vagina and oropharynx of mice with a bacteriophage lytic enzyme," *Antimicro B. Agents Chemother.* 49, pp. 111-117 (2005); Fischetti, V. A., "Novel method to control pathogenic bacteria on human mucous membranes," *Ann. N.Y. Acad. Sci.* 987, pp. 207-214 (2003); Fischetti, V. A., "Phage antibacterials make a comeback," *Nature Biotechnol.* 19, pp. 734-735 (2001); Koehler, T. M. Bacillus anthracis, pp. 519-528 (2000) in V. A. Fischetti, R. P. Novick, J. J. Ferretti, D. A. Portnoy, and J. I. Rood (ed.), Gram-positive pathogen, American Society for Microbiology, Washington, D. C.; Loeffler, J. M., D. Nelson, and V. A. Fischetti, "Rapid killing of *Streptococcus pneumoniae* with a bacteriophage cell wall hydrolase," *Science* 294, pp. 2170-2172 (2001); Loeffler, J. M., S. Djurkovic, and V. A. Fischetti, "Phage lytic enzyme Cpl-1 as a novel antimicrobial for pneumococcal bacteremia," *Infect. Immun.* 71, pp. 6199-6204 (2003); and Nelson, D., L. Loomis, and V. A. Fischetti, "Prevention and elimination of upper respiratory colonization of mice by group A *streptococci* by using a bacteriophage lytic enzyme," *Prot. Natl. Acad. Sci. USA.* 98, pp. 4107-4112 (2001).

Cloning of Phage Lysins from *E. faecalis* Bacteriophages

Lysins may be identified and isolated from *E. faecalis* phage φ1 from a genomic library. The putative ORFs from approximately 4 kb of sequenced φ1 DNA may be identified using the ORF Finder program within the National Center for Biotechnology Information (NCBI) website. DNA analysis reveals a common ORF of 945 bp in both positive clones from the Tsp509I and HindIII genomic libraries, which translates to a putative protein of 314 amino acids with a predicted molecular weight of 34 kDa. This ORF encoding the putative phage φ1 lysin is named plyV12 and its putative protein product PlyV12 (SEQ ID NO:1). This translated ORF may be searched against multiple databases using the BLAST program on the NCBI website. An alignment of the PlyV12 sequence from *E. faecalis* bacteriophage φ1 with lysins from bacteriophages of *Streptococcus agalactiae* (a group B *streptococcus*), *S. pyogenes* (a group A *streptococcus*), *S. pneumoniae, S. mitis* and *S. thermophilus* reveals similarities primarily limited to the amino termini of these molecules, which correspond to the catalytic domain of most lysins (FIG. 2). Since several of these lysins are known to confer N-acetylmuramyl-L-alanine amidase activity, PlyV12 is believed to be an amidase. The diminished sequence similarity among the carboxy terminal portions of all these lysins suggests that they have distinct cell wall binding epitopes and hence different bacterial specificities. The alignment suggests that PlyV12 is consistent with the modular structure found in most lysins.

FIG. 2 shows an alignment of the amino acid sequence of PlyV12 from *E. faecalis* bacteriophage φ1 (Ef) (SEQ ID NO:1) with lysins from five other Gram-positive bacteriophages. Those phages include λSa2 from *Streptococcus Agalactiae*, a group B *streptococcus*, (Sa) (SEQ ID NO:2); 315.3 from *S. pyogenes*, a group A *streptococcus*, (Spy) (SEQ ID NO:3); Dp-1 from *S. pneumoniae* (Spn) (SEQ ID NO:4); SM1 from *S. mitis* (Sm)(SEQ ID NO:5); and Sfi19 from *S. thermophilus* (St) (SEQ ID NO:6). Identical residues are highlighted by black boxes, while conserved residues are highlighted with gray boxes. The asterisks above the alignment denote an invariant cysteine and histidine residue among all six phage lysins, while residues of PlyV12 that correspond to consensus sequence of the CHAP domain are listed below the alignment.

ORFs proximal to plyV12 were identified in bacteriophage φ1. A total of approximately 4 kb of DNA including and surrounding the lysin ORF of phage φ1 was sequenced. Other than plyV12, two additional ORFs were identified within this region of DNA by the ORF Finder program (FIG. 3). A putative ORF encoding for a phage capsid protein was found 693 bp downstream of the lysin ORF, transcribed in the opposite direction. Another ORF was identified 116 bp upstream of the lysin ORF, orientated in the same direction, but encoded in a different reading frame. The 5' sequence of this ORF is incomplete. Nonetheless, a BLAST search was conducted with the 203 amino acid sequence translated from 612 bp of DNA sequence data.

Generally, holin proteins are encoded adjacent to lysin genes in what is termed the "lysis cassette" (Young, R., and U. Blasi. 1995. Holins: form and function in bacteriophage lysis.

FEMS Microbiol. Rev. 17:191-205; and Young, R., I.-N. Wang, and W. D. Roof. 2000. Phages will out: strategies of host cell lysis. Trends Microbiol. 8:120-128). There are an extensive number of holin families, and the amino acid sequences of holins are not usually conserved. However, holins are characteristically hydrophobic, a characteristic attributable to its transmembrane spanning domains. In an effort to determine if any of the unmatched ORFs encode for a holin gene, they may be tested for membrane solubility using an Internet accessible computer program (http://sos-ui.proteome.bio.tuat.ac.jp/sosui submit.html). The holin gene of phage φ1 is not believed to be within the 4 kb of sequenced DNA.

FIG. 3 is a schematic showing the locations and orientation of the ORFs identified from 4 kb of sequenced phage φ1 DNA. The ORFs are drawn approximately to scale in kilobases, shown below the illustration. The 612 bp of partial lysM sequence is represented as a first arrow 10, as well as the full length plyV12 lysin ORF, represented by a second arrow 20, with a predicted length of 945 bp. There is 116 bp separating both ORFs which are transcribed in different reading frames. Six hundred ninety three basepairs (693 bp) downstream of the lysin ORF is a putative ORF of 789 bp encoding for a capsid protein oriented in the opposite direction, represented by a third arrow 30.

Expression of *Enterococcus* Bacteria Lysogenic Phage Lysins

Expression and Lytic Activity of Enterococcal Phage Lysins

In one example, a lysin was produced by expression of a lysin in *E. coli* XL1-Blue. Initial OD assays carried out with lysates from 4 hour induced XL1-Blue/pBAD24-lysin2, lysed by the chloroform method, against *E. faecalis* V12 show optical density decrease that occurred at a rate that is much slower compared with other phage lysins that are characterized by lysins described by: Loeffler, J. M., D. Nelson, and V. A. Fischetti, "Rapid killing of *Streptococcus pneumoniae* with a bacteriophage cell wall hydrolase," *Science* 294, pp. 2170-2172 (2001); Nelson, D., L. Loomis, and V. A. Fischetti, "Prevention and elimination of upper respiratory colonization of mice by group A *streptococci* by using a bacteriophage lytic enzyme," *Prot. Natl. Acad. Sci. USA* 98, pp. 4107-4112 (2001); and Schuch, R., D. Nelson, and V. A. Fischetti, "A bacteriolytic agent that detects and kills *Bacillus anthracis*," *Nature* 418, pp. 884-888 (2002), which are incorporated by reference herein in their entirety.

Preferably, lysins produced by expression of PlyV12 in *E. coli* XL1-Blue are characterized by a lytic activity against *E. faecalis*. *E. faecalis* V12 incubated with PlyV12 crude lysate resulted in viability counts that were at least 10-fold, preferably at least 20-, 30-, 40-, 50-, 60-, 70-, 80-, 90-, 100-fold lower than *E. faecalis* incubated with buffer. Viability assays were conducted to confirm the production of a protein with a lytic activity against *E. faecalis*. *E. faecalis* V12 incubated with PlyV12 crude lysate results in viability counts that are at least 100-fold lower than *E. faecalis* incubated with buffer. SDS-PAGE of XL1-Blue/pBAD24-lysin2 induced lysate do not show an overexpressed protein band at 34 kDa, the predicted molecular weight of PlyV12. Collectively, these results suggest that PlyV12 may be expressed at very modest levels in *E. coli* XL1-Blue.

In another example, a lysin is produced by cloning into pBluescript KS+. For example, the plyV12 ORF with about 100 bp of φ1 flanking sequence were also be cloned into pBluescript KS+ resulting in pBluescript-lysin2. SDS-PAGE of overnight induced XL1-Blue/pBluescript-lysin2 lysate also does not show an overexpressed protein band of molecular weight 34 kD. This result suggests that PlyV12 is also expressed at relatively low levels from this plasmid.

The yields of PlyV12 from 4 hour induced XL1-Blue/pBAD24-lysin2 cultures lysed by different methods may be compared by titering of lytic activity against *E. faecalis* V12. Lysis by homogenization yields about four-fold more lytic activity than lysis with chloroform, while lysis with BugBuster provides the lowest yield among all three methods.

A lysin may also produced by expression of PlyV12 in *E. coli* RosettaBlue. The codon usage frequency of *E. coli* strains may be examined in a number of ways. The plyV12 sequence was analyzed on the *E. coli* Codon Usage Analyzer 2.0 program at www.biology.ualberta.ca/pilgrim.hp/links/usage2.0c.html. This approach demonstrates that approximately 20% of the plyV12 ORF is below the threshold of expression in *E. coli* when codons present in *E. coli* at less than 10% were taken into consideration. References to the Codon Usage Database at www.kazusa.or.jp/codon, as well as an article on rare codon clusters in *E. coli* (64) confirm that over 10% of PlyV12 codons are used by *E. coli* at a frequency of less than 1%. Based on this approach, it is believed that the codon usage pattern in plyV12 is not compatible with that of *E. coli*. The *E. coli* RosettaBlue strain harbors a ColE1-compatible chloramphenicol resistant plasmid that encodes tRNA genes for AGG, AGA, AUA, CUA, CCC and GGA. Codons used by *E. coli* at a frequency of less than 1% and occurring at least 5 times in plyV12 are GGA, ACA, AGU, CCA and CCU. Since only one of these tRNA genes is supplemented by the RosettaBlue strain, that for GGA, expression of PlyV12 in RosettaBlue is predicted to be higher than in XL1-Blue.

Lysates of 4 hour induced PlyV12 expression from pBAD24-lysin2 in RosettaBlue produce an optical density decrease of *E. faecalis* V12 as compared to lysate from RosettaBlue. However, SDS-PAGE of cell lysates still does not show an overexpressed protein band at 34 kDa, suggesting that despite expression of PlyV12 (as evidenced by lytic activity against *E. faecalis*), high level expression is not achieved. Similar results obtained from SDS-PAGE of whole cell pellets (not shown) indicate that PlyV12 is not sequestered within inclusion bodies.

Expression of Histidine Tagged PlyV12 in *E. coli* RosettaBlue

Lysates from induced RosettaBlue/pBAD24-lysin2 and RosettaBlue/pBAD24-6×his-lysin was separated by SDS-PAGE and subjected to Western blotting using antibodies against the polyhistidine tag. A positive band in the RosettaBlue/pBAD24-6×his-lysin lane corresponds to the predicted size of histidine tagged PlyV12 at approximately 38 kDa, while there are no visible bands in the RosettaBlue/pBAD24-lysin2 lane. These results suggest that the histidine tagged PlyV12 is expressed in *E. coli* RosettaBlue.

Cell lysates containing histidine tagged PlyV12 exhibit a slower rate of lytic activity against *E. faecalis* V12 as compared to lysates containing native PlyV12 measured by the OD assay. To determine if the histidine tag was interfering with the lytic activity of PlyV12, the polyhistidine tag was cleaved using enterokinase. Enterokinase treatment results in formation of a precipitate, along with the inactivation of PlyV12. Instead, the less efficient lytic activity of histidine tagged PlyV12 was attributed to the elimination of the upstream φ1 sequence. A new clone of untagged plyV12 lacking the additional upstream sequence (pBAD24-lysin1.5) also contains less efficient lytic activity than pBAD24-lysin2, which harbors approximately 100 bp of φ1 sequence upstream. The lytic efficiencies of lysates containing histidine tagged PlyV12, and PlyV12 expressed from pBAD-lysin1.5 are comparable as measured by the OD assay.

Expression of PlyV12 in *B. megaterium* WH320

PlyV12 may be identified based on a genetic screening process in which a φ1 genomic library is screened for lytic agents active against *E. faecalis* strain V12. A 945 bp open reading frame (ORF) is identified after DNA sequencing of a lytic clone. The ORF translates into a protein of 314 amino acids with a molecular mass of approximately 34 kilo Daltons (kDa). The plyV12 gene is initially cloned into several *Escherichia coli* expression systems, however, the enzyme yields are very low in all cases. PlyV12 (as other lytic enzymes) is translated without a leader sequence, thus it is believed to remain in the cytoplasm, where it may not exert an effect on its peptidoglycan substrate, making it possible to be expressed in a wide range of systems. Subsequently, the plyV12 gene and approximately 100 bp of flanking sequence may be amplified by polymerase chain reaction and cloned into an *E. coli-Bacillus* shuttle vector pDG148, yielding pPY1.

A lysin may also be expressed in *B. megaterium*. For example, PlyV12 is expressed in *Bacillus megaterium* strain WH320 (MoBiTec, Marco Island, Fla.) by induction with isopropyl-β-D-thiogalactopyranoside. *B. megaterium* WH320 harboring pDG148-lysin2 is induced with IPTG for up to 3 hours, with samples removed every hour. Lysates from the different induction times are OD assayed against *E. faecalis* V12. While all samples contained lytic activity against *E. faecalis* V12, the 1 hour induced sample has the most efficient lytic activity. Despite the lytic activity of PlyV12 expressed in *B. megaterium* being higher than in *E. coli*, as observed by the increased rate of optical density decrease, the protein still was not distinguishable by SDS-PAGE of lysates. Lysates of induced *B. megaterium*/pVK55a-lysin2 and *B. megaterium*/pDG148-6×his-lysin did not contain detectable lytic activity against *E. faecalis* by the OD assay. Furthermore, a Western blot of *B. megaterium*/pDG148-6×his-lysin lysate with poly-histidine antibodies is negative.

Expression of *E. faecalis* Lysogenic Phage Lysins in *E. coli*

Lysates of different clones, along with that of plyV12, were tested to investigate the rate of *E. faecalis* lysis, as measured by OD assays. XL1-Blue/pBAD-EF1293 does not grow when induced, while XL1-Blue/pBAD-EF0355 grows significantly slower than other clones. In contrast, RosettaBlue/pBAD-EF1293 grows upon induction at 37° C. for 4 hours, but RosettaBlue/pBAD-lysin2 grows at a slower rate than other clones.

Figure 4A:
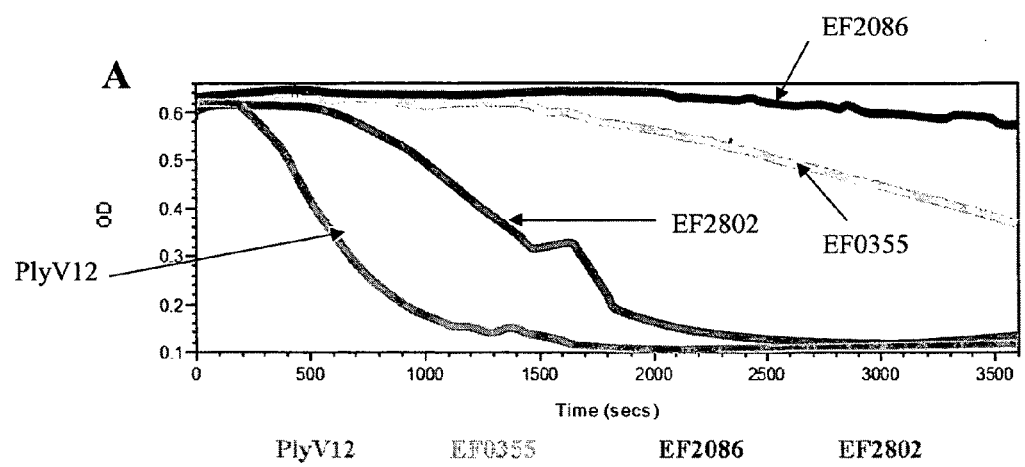
FIG. 4A is a graph showing a comparison of the lytic activities of E. faecalis V583 lysogenic phage lysins with that of PlyV12 expressed in E. coli XL1-Blue by OD assays of E. faecalis V12.
Figure 4B:
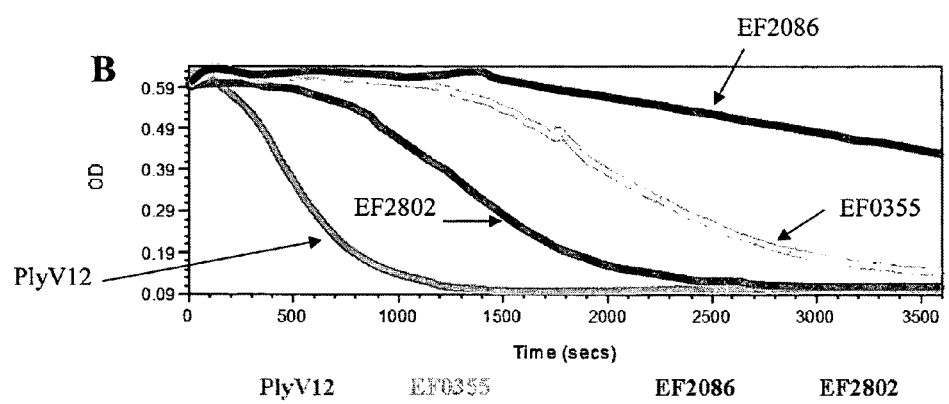
FIG. 4B is a graph showing a comparison of the lytic activities of E. faecalis V583 lysogenic phage lysins with that of PlyV12 expressed in E. coli XL1-Blue by OD assays of E. faecalis V12.

FIG. 4A, 4B and FIGS. 5A, 5B show the OD assays of the lytic activities of different lysin clones on *E. faecalis* V12 expressed in XL1-Blue and RosettaBlue under varying induction conditions. More specifically, FIGS. 4A and 4B show a comparison of the lytic activities of *E. faecalis* V583 lysogenic phage lysins with that of PlyV12 expressed in *E. coli* XL1-Blue by OD assays of *E. faecalis* V12, measured by OD assays. To obtain the data for FIG. 4A, clones was induced for 4 hours at 37° C. To obtain the data for FIG. 4B, clones were induced for 4 hours at 30° C., followed by overnight incubation at 4° C. with gentle shaking, followed by addition of one hundred microliters of each *E. coli* lysate to an equal volume of *E. faecalis* V12 suspension. All reactions were carried out in 96 well plates and change in optical density at 600 nm was monitored on an automated spectrophotometer over 1 hour, with readings taken every 30 seconds.

Figure 5A:
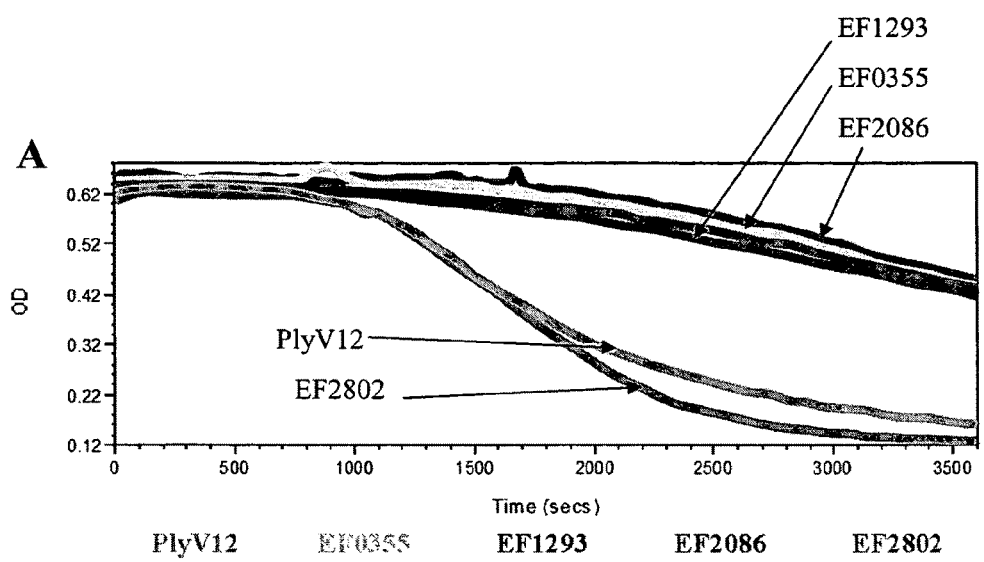
FIG. 5A is a graph showing a comparison of the lytic activities of E. faecalis V583 lysogenic phage lysins with that of PlyV12 expressed in E. coli RosettaBlue by OD assays of E. faecalis V12.
Figure 5B:
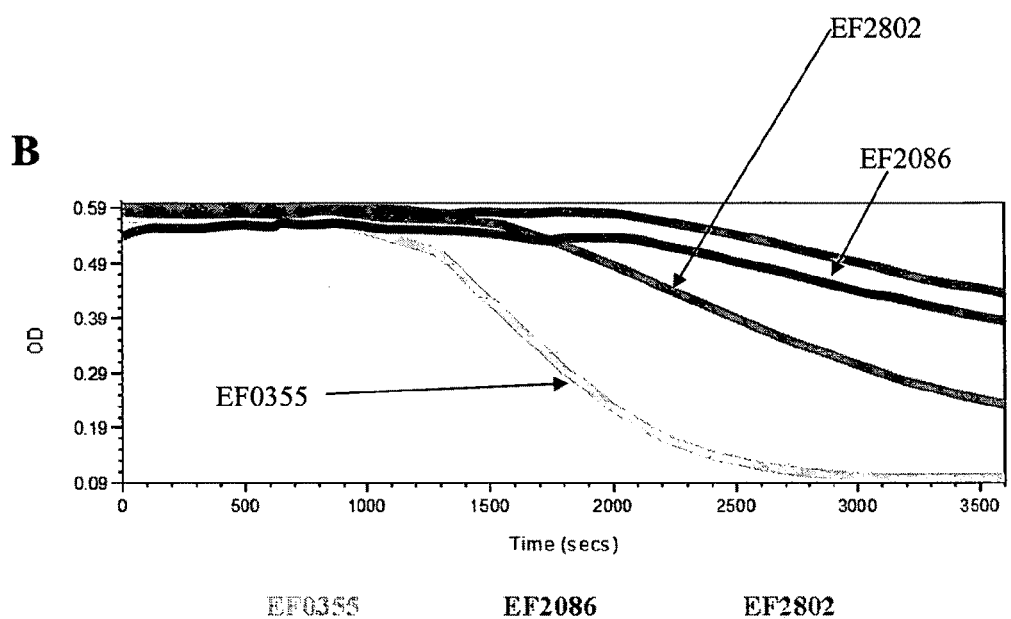
FIG. 5B is a graph showing a comparison of the lytic activities of E. faecalis V583 lysogenic phage lysins with that of PlyV12 expressed in E. coli RosettaBlue by OD assays of E. faecalis V12.

PlyV12 lysate is represented by lines 100 (FIG. 4A) and 101 (FIG. 4B), EF0355 by line 120 (FIG. 4A) and 121 (FIG. 4B), EF2086 by line 130 (FIG. 4A) and 131 (FIG. 4B) and EF2802 by line 110 (FIG. 4A) and 111 (FIG. 4B). All clones were lysed using the BugBuster reagent. Under both induction conditions in XL1-Blue, lysates containing EF0355 and EF2802 demonstrate a lytic effect on *E. faecalis* V12, although their rate of enterococcal lysis is slower than that of PlyV12 (FIG. 4). FIGS. 5A and 5B show a comparison of the lytic activities of *E. faecalis* V583 lysogenic phage lysins with that of PlyV12 expressed in *E. coli* RosettaBlue by OD assays of *E. faecalis* V12. In obtaining data for FIG. 5A, clones were induced for 4 hours at 37° C. In obtaining data for FIG. 5B, clones were induced for 4 hours at 30° C., followed by overnight incubation at 4° C. with gentle shaking. One hundred microliters of each *E. coli* lysate were added to an equal volume of *E. faecalis* V12 suspension. All reactions were carried out in 96 well plates and change in optical density at 600 nm was monitored on an automated spectrophotometer over 1 hour, with readings taken every 30 seconds.

A PlyV12 lysate is represented by lines 200 (FIG. 5A), EF0355 by line 220 (FIG. 5A) and 221 (FIG. 5B), EF2086 by line 230 (FIG. 5A) and 231 (FIG. 5B), EF1293 by line 240 (FIG. 5A), and EF2802 by line 210 (FIG. 5A) and 211 (FIG. 5B). In RosettaBlue, after a 4 hour induction at 37° C., the only lysogenic phage lysin to demonstrate lysis of *E. faecalis* is EF2802 (FIG. 5A). After a 4 hour induction at 30° C. followed by overnight incubation at 4° C. however, EF0355 demonstrates *E. faecalis* lysis in addition to EF2802 (FIG. 5B). Under these induction conditions, RosettaBlue/pBAD24-EF1293 and RosettaBlue/pBAD24-lysin2 grow poorly. Despite several V583 lysogenic phage lysins exhibiting lytic activity against *E. faecalis*, their rate of enterococcal lysis is not significantly greater than PlyV12. Although the assays shown here were carried out using *E. faecalis* V12, assays with strain V583 give very similar results.

Preferably, a lysin kills *E. faecalis* V12 within a period of 1 hour or less. More preferably, combination of one hundred microliters of a lysin added to an equal volume of *E. faecalis* V12 suspension results in a reduction in optical density at 600 nm as monitored on an automated spectrophotometer over an initial induction period. For example, FIG. 4A and FIG. 4B show reduction in the optical density of a PlyV12 lysin (SEQ ID NO:1) from about 0.6 to less than 0.2, approximately a 67% reduction, after about 15 min. Reduction of optical density for other lysins are also shown in FIG. 4A and FIG. 4B. Similarly, FIG. 5A shows reduction in the optical density of a PlyV12 lysin (SEQ ID NO:1) from about 0.6 to less than 0.2, approximately a 50% reduction, after about 30 min. Reduction of optical density for other lysins are also shown in FIG. 5A. FIG. 5B shows reduction in the optical density of a PlyV12 lysin (SEQ ID NO:1) from about 0.6 to less than 0.2, approximately a 50% reduction, after about 30 min. Reduction of optical density for other lysins are also shown in FIG. 5B.

Purification of *Enterococcus* Bacteria Lysogenic Phage Lysins

Figure 6:
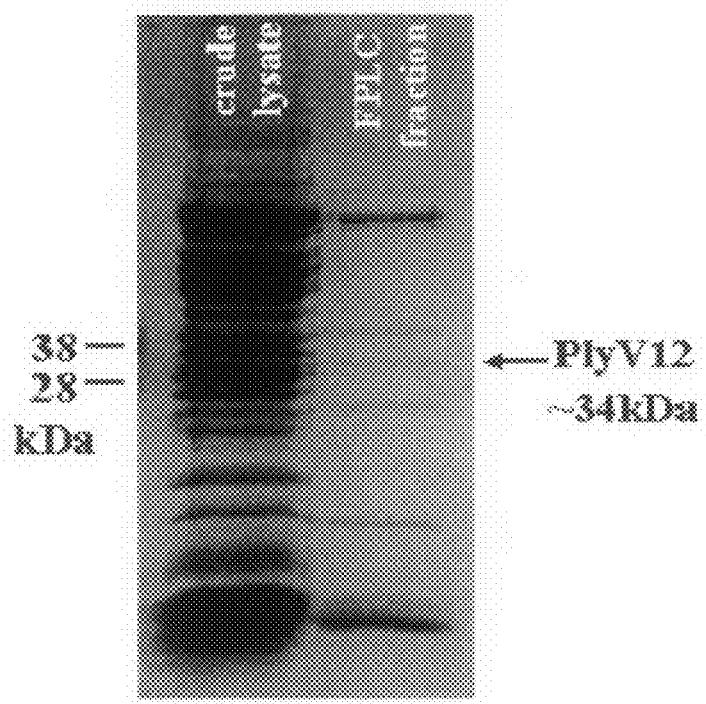
FIG. 6 shows results from SDS-PAGE purification of PlyV12 on a cation exchange column.

Fractions of PlyV12 purified over the HiTrap SP HP cation exchange columns corresponding to the major $OD_{280}$ peak at approximately 330 mM NaCl containing lytic activity against *E. faecalis* V12 by the OD assay were pooled. SDS-PAGE of these purification fractions indicates the presence of approximately 8 protein bands, including a protein at 34 kDa, the predicted size of PlyV12 (FIG. 6). The final PlyV12 sample were purified to >85% based on spot densitometry (Alpha Innotech's AlphaImager™, San Leandro, Calif.) of the SDS-PAGE gel images of crude and purified PlyV12.

FIG. 6 shows the purification of PlyV12 on a cation exchange column. PlyV12 is expressed from *B. megaterium* WH320/pDG148-lysin2 by induction with IPTG for 1 hour. The cell lysate is purified through cation exchange columns (Hi Trap SP HP, Amersham Biosciences). Elution fractions containing lysin activity were pooled and subjected to separation by sodium dodecyl sulfate-polyacrylamide gel electrophoresis (SDS-PAGE). PlyV12 has a predicted molecular weight of about 34 kDa. The arrow shows the position of its migration.

Upon elution from the cation exchange columns, purified PlyV12 typically contains less than 10 units/mL of lytic activity. Unless otherwise indicated, purified PlyV12 used in all subsequent experiments were concentrated to 25-30 units/mL in a 30 kDa cutoff Amicon Ultra unit (Millipore). Interestingly, lytic activity of PlyV12 higher than 30 units/mL was not achieved despite further concentration.

Analysis of the Lytic Activity of PlyV12 Under Different Conditions

PlyV12 or a PlyV12 variant polypeptide may be exposed to a range of different biochemical conditions—including pH, temperature and salinity—to determine the conditions optimal to its killing activity against various bacteria. PlyV12 is an example of a preferred lysin.

Susceptibility of *E. faecalis* V12 to PlyV12 at Different Stages of Growth

*E. faecalis* V12 grown in BHI at 37° C. for between one to four hours, with approximate OD600 values ranging from 0.07 to 1.6, are equally susceptible to PlyV12, as measured and compared by OD assays. Beyond 5 hours of growth, however, the rate of OD decrease is slower in comparison, although still susceptible to PlyV12 action. For this reason, assays with PlyV12 are preferably carried out with *E. faecalis* V12 grown for three hours at 37° C.

The pH Range of PlyV12 Activity

In another particular aspect, the lysins provided exhibit lytic activity against *E. faecalis* strain V12 bacteria, as measured by at least a 20% decrease in $OD_{600}$ in 15 minutes, over a pH range of about 5.0 to 8.0, preferably about 5.0 to 7.5, and most preferably at about 6.0 to 7.5. Preferably, the lysins provided exhibit lytic activity against *E. faecalis* strain V12 bacteria, as measured by at least a 25% decrease in $OD_{600}$ after 15 minutes, at a pH of about 5.0 to about 8.0, more preferably at least a 40% decrease in $OD_{600}$ after 15 minutes, at a pH of about 5.0 to about 7.5, more preferably at least a 50% decrease in $OD_{600}$ after 15 minutes, at a pH of about 5.0 to about 7.0, more preferably at least a 60% decrease in $OD_{600}$ after 15 minutes, at a pH of about 5.0 to about 6.5, and more preferably at least a 40%, 50%, 60%, 65% or 70% decrease in $OD_{600}$ after 15 minutes, at a pH of about 6.0. Preferably, a composition comprises PlyV12 at a pH of about 5.0, 6.0, 7.0, 8.0 or any pH interval of 0.05 therebetween, or any pH interval that is a multiple of 0.05 therebetween, including pH values of 5.2, 6.5, 7.5 and 8.5.

Figure 7:
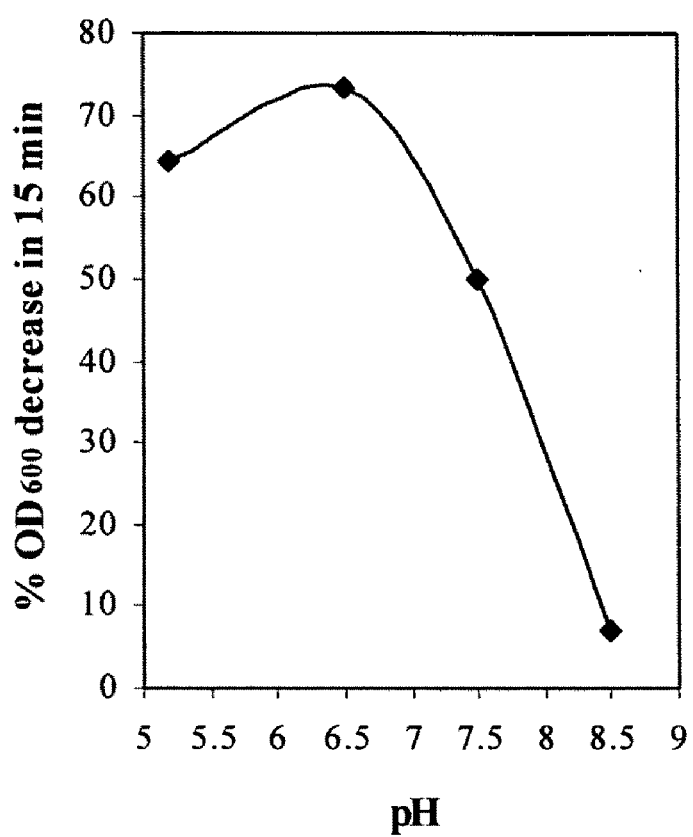
FIGS. 7 is graph showing the lytic activity of PlyV12 at different pH conditions.

As shown in FIG. 7, PlyV12 has maximal activity at about pH 6.0, while retaining activity at pH 5.0 and 7.5. PlyV12 activity against *E. faecalis* strain V12 may be tested at pH 5.2, 6.5, 7.5 and 8.5. PlyV12 activity may be measured by an optical density assay and plotted as the percentage decrease in optical density at 600 nm in 15 minutes. Activity decreases rapidly at higher pH, resulting in near inactivation at pH 8.5, a profile common among bacteriophage lysins (Loeffler, J. M., S. Djurkovic, and V. A. Fischetti, "Phage lytic enzyme Cpl-1 as a novel antimicrobial for pneumococcal bacteremia," *Infect. Immun.* 71, pp. 6199-6204 (2002)).

PlyV12 Activity in the Presence of Increasing NaCl

Figure 8:
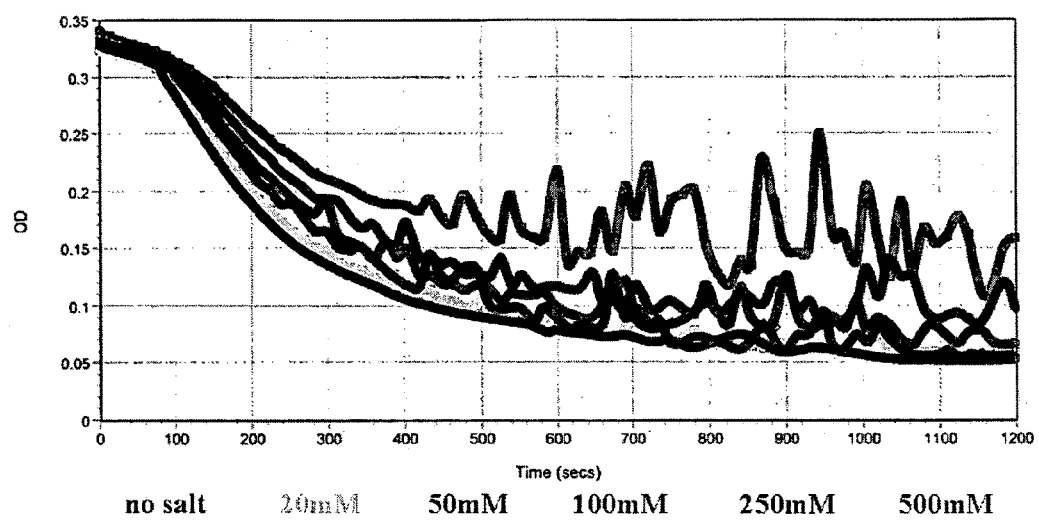
FIG. 8 is a graph showing the effect of increasing salt concentrations on PlyV12 activity.

The lysins were characterized by an increased lytic activity in sodium chloride concentrations up to at least about 250 mM. Preferably, the addition of varying amounts of a 5M sodium chloride stock solution to a lysin and *E. faecalis* V12-PlyV12 and performing an OD assay results in a killing activity of the lysin (measured by greater decrease in optical density measurements) of at least 50% after 1 hour in salt concentrations of up to about 250 mM. For example, PlyV12 function at physiological salt concentrations, while sodium chloride greater than 250 mM deteriorated its activity. FIG. 8 shows the effect of increasing NaCl salt concentration on PlyV12 activity. To obtain the data shown in FIG. 8, a 5M sodium chloride stock solution was added to *E. faecalis* V12-PlyV12 lytic assays and measured by the OD assay. A control reaction with no sodium chloride was added, as represented in red (300), NaCl added to 20 mM in yellow (310), 50 mM in green (320), 100 mM in purple (330), 250 mM in blue (340) and 500 mM in gray (350). Changes in optical density at 600 nm were monitored on an automated spectrophotometer over 20 minutes, with readings taken every 15 seconds.

In one embodiment, a composition comprising PlyV12 at a salt concentration of about 0.9% salt (sodium chloride) is provided. Other embodiments provide compositions comprising PlyV12 in a sodium and/or chloride concentration of about 10, 20, 30, 40, 50, 60, 70, 80, 90, 100, 110, 120, 130, 140, 150, 160, 170, 180, 190, 200, 210, 220, 230, 240, or 250 mM, more preferably between about 0 mM and about 500 mM, including intervals of 1 mM therebetween, and most preferably between about 0 mM and about 250 mM.

Specificity of PlyV12 Action

Figure 9A:
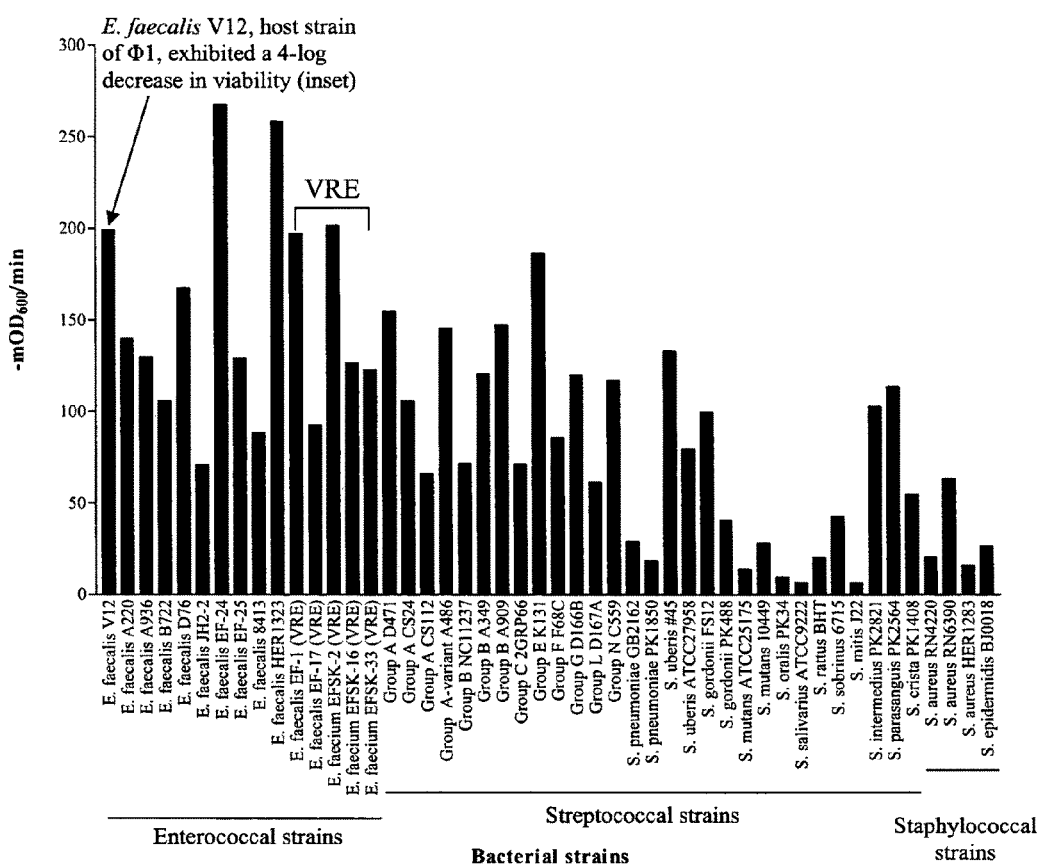
FIG. 9A is a graph showing the activity of PlyV12 against various enterococcal, streptococcal and staphylococcal strains.
Figure 9B:
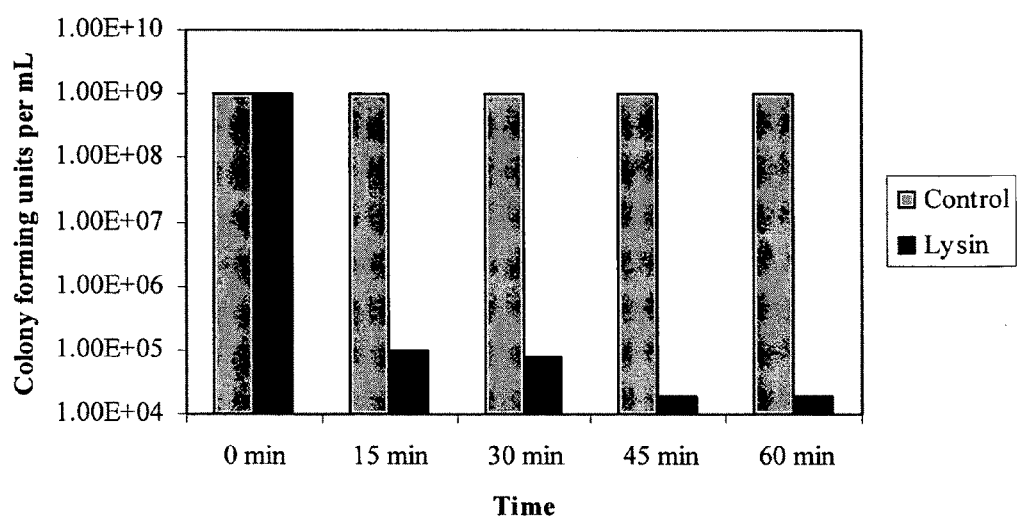
FIG. 9B is a graph showing the activity of PlyV12 in a direct viability assay performed with E. faecalis strain Vi 2 incubated with PlyV12.

Preferably, the lysins exhibit killing activity against two or more bacteria. For example, in addition to killing its host bacterial strain *E. faecalis* strain V12, PlyV12 also has lytic activity against at least 14 clinical and laboratory *E. faecalis* and *E. faecium* strains, including two vancomycin resistant *E. faecalis* strains and three vancomycin resistant *E. faecium* strains (FIG. 9A, 9B). PlyV12 exhibits significant lethal activity against other pathogens such as *S. pyogenes*, groups B, C, E and G *streptococci*, with minimal effects against commensal bacteria (with the exception of *S. gordonii*). PlyV12 may be used as a therapeutic agent specific for multiple pathogens responsible for serious infections. While the organization of the primary structure of PlyV12 and the nature of its enzymatic activity make PlyV12 consistent with other bacteriophage lysins previously studied, PlyV12 is believed to be the first bacteriophage lysin described to have activity against *Enterococcus* species. PlyV12's spectrum of activity against numerous bacterial strains is believed to be unique.

Lysin lytic activity may be expressed as units per milliliter (units/mL), in which units represent the reciprocal of the highest dilution of enzyme resulting in a 50% reduction in bacterial optical density at a wavelength of 600 nm ($OD_{600}$) in 15 minutes. Subsequent bacterial killing experiments may be carried out with a 25 units/mL PlyV12 preparation. For the lysin killing assays, the bacterial strains to be assayed may be grown to mid logarithmic phase in brain-heart infusion broth, pelleted and resuspended in PBS at pH 7.4 to $OD_{600}$ of 2.0. The pH profile experiments for PlyV12 activity may be performed after the bacterial cells are resuspended in 100 mM acetate buffer at pH 5.2, 100 mM MOPS at pH 6.5, or 100 mM Tris at pH 7.5 or pH 8.5. A hundred microliter bacterial suspension may be mixed with 100 µL of PlyV12 at 25 units/mL. For optical density assays, the $OD_{600}$ of the mixture may be monitored every 15 seconds with shaking over a 15 minute period on an automated 96 well plate reader (Molecular Devices' SpectraMax Plus 384, Sunnyvale, Calif.). For viability assays, the bacteria and PlyV12 mix may be incubated at room temperature with gentle shaking for specified amounts of time, and at designated time points, aliquots may be removed, serially diluted and plated on agar plates to obtain viability counts.

FIG. 9A shows the activity of PlyV12 lysin against various bacteria. PlyV12 activity against *enterococcal, streptococcal* and staphylococcal strains were measured as the rate of decrease in OD per minute, expressed in milliunits of $OD_{600}$ per minute. This velocity measurement permits direct comparison of PlyV12 activities among bacterial species. Vancomycin resistant *enterococci* strains are indicated as "VRE" in FIG. 9A.

PlyV12 has bactericidal activity against certain strains of *E. faecalis* and *E. faecium* tested, including certain clinical strains and strains resistant to the antibiotic vancomycin. Vancomycin is considered the last line of defense against many bacterial pathogens that were already resistant to other available antibiotics (Cetinkaya, M., P. Falk, and C. G. Mayhall. 2000. Vancomycin-resistant *enterococci*. Clin. Microbiol. Rev. 13:686-707). *Enterococci* are a leading cause of nosocomial infections, and treating these infections with conventional antibiotics have become increasingly difficult in light of the acquisition of antibiotic resistance genes by these organisms. It is anticipated that soon *enterococci* may be untreatable by current antibiotics, and alternative means of combating infections caused by these organisms will be urgently needed. PlyV12 is a viable candidate for such an enterococcal therapeutic agent.

The assays for FIG. 9A were carried out using a measurement of optical density, which corresponds to bacterial viability. However, to better quantitate the extent of bacterial killing, a direct viability assay was performed with *E. faecalis* strain V12 incubated with PlyV12. Results are shown in FIG. 9B, showing a greater than 4-log reduction in viability when exposed to 2.5 units of PlyV12 for 15 minutes, corresponding to a decrease of 200 $mOD_{600}$/min in the optical density assay. Viability continues to decrease in this strain upon further incubation with PlyV12. FIG. 9B shows the results of viability assay of *E. faecalis* strain V12 treated with PlyV12. Viability was measured in colony forming units per milliliter. Interestingly, PlyV12 also exhibits a significant killing effect on strains of pathogenic *streptococci*, including *S. pyogenes* (group A *streptococci*), group B *streptococci*, and group C *streptococci*, in addition to strains of *Staphylococcus aureus*, another high level antibiotic resistant nosocomial pathogen. The above assays were carried out using a measurement of optical density, which corresponds to bacterial viability. However, to better quantitate the extent of bacterial killing, a direct viability assay was performed with *E. faecalis* strain V12 incubated with PlyV12. Results reveal >4-log reduction in viability when exposed to 25 units/mL of PlyV12 for 15 minutes, which corresponds to a decrease of 200 milliunits of $OD_{600}$ per minute ($mOD_{600}$/min) in the optical density assay (FIG. 9B). Viability continues to decrease in this strain upon further incubation with PlyV12.

Examination of the Active Center of PlyV12's Catalytic Activity

Ply12 harbors an Active Site Cysteine at its Catalytic Center

Figure 10:
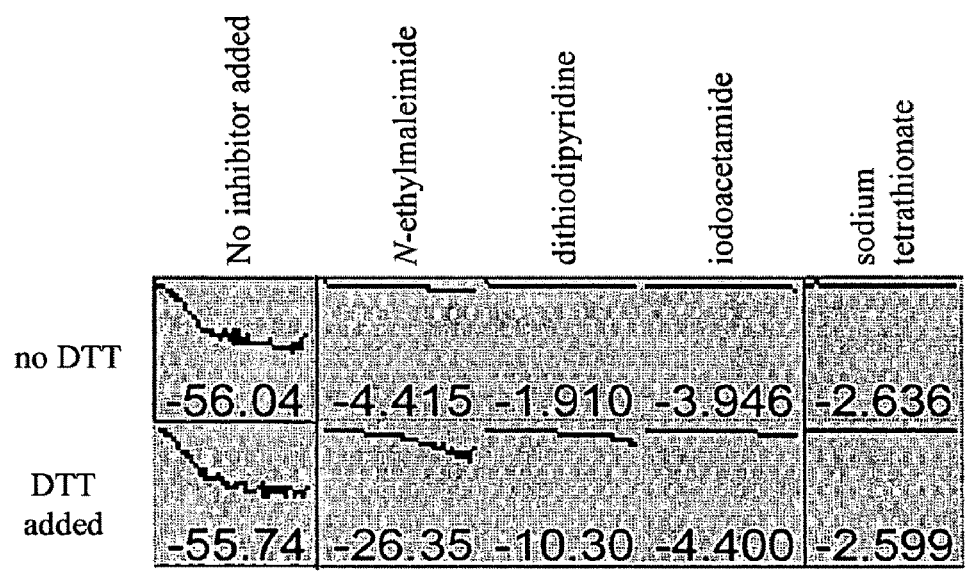
FIG. 10 are graphs showing the inhibition of PlyV12 by various cysteine inhibitors, measured by the $OD_{600}$ change of each reaction.

Some phage lysins harbor a CHAP domain (cysteine, histidine-dependent amidohydrolases/peptidases) within the module of the protein known to confer catalytic activity. As its name suggests, proteins with a CHAP domain are believed to require a cysteine and histidine residue for an active catalytic center. Although a CHAP domain is not identified within PlyV12 by the NCBI Conserved Domain Search program, PlyV12 activity was inhibited by a series of active site cysteine inhibitors, including N-ethylmaleimide, iodoacetamide, sodium tetrathionate and dithiodipyridine (FIG. 10). Inhibition by N-ethylmaleimide is reversible with the addition of DTT. These results strongly indicate that PlyV12 harbors an active site cysteine residue required for its catalytic function. The presence of a conserved cysteine and histidine residue in the catalytic domain, as evidenced in the protein sequence alignment with other lysins, suggests that PlyV12 may possibly contain a CHAP domain. Furthermore, a number of amino acids within the catalytic domain of PlyV12 correspond with the consensus sequence of CHAP domains.

PlyV12 Action is not Dependent on Divalent Cation Cofactors

The lytic activity of PlyV12 is not affected by the addition of EDTA to a final concentration of 5 mM. Since EDTA is known to sequester divalent cations, this result suggests that PlyV12 lytic activity is not dependent on divalent cations. FIG. 10 shows the inhibition of PlyV12 by cysteine inhibitors. Referring to the data shown in FIG. 10, cysteine active site inhibitors N-ethylmaleimide, iodoacetamide and sodium tetrathionate are added to lytic assays of PlyV12 and *E. faecalis* V12 at a final concentration of 2 mM, while dithiodipyridine is added at a final concentration of 30 µM; no DTT is added to the top reactions, while DTT is added to 8 mM on the duplicate reactions on the bottom. Each graph in FIG. 10 represents the $OD_{600}$ change of each reaction monitored over a 15 minute period. The number below each graph is the Vmax value, which represents the change in optical density per unit time.

PlyV12 Activity in the Presence of Mouse and Human Blood

Viability assays of *E. faecalis* V12 exposed to PlyV12 in the presence of mouse and human blood were set up to determine if PlyV12 lytic activity was inhibited in blood. In the presence of blood, PlyV12 activity is indeed severely inhibited, decreasing *E. faecalis* viability by only a log as compared to its activity in the absence of blood which decreased *E. faecalis* viability from $10^7$ CFU/mL to undetectable levels (Table 1). The results from both mouse and human blood are comparable.

Table 1 summarizes the inhibition of PlyV12 lytic activity in the presence of mouse and human blood. One hundred microliters of PlyV12 at 30 units/mL was mixed with 100 µL of *E. faecalis* V12 suspension in the presence of either 500 µL of mouse or human blood. The reactions was incubated for 30 minutes followed by immediate dilutions and plating for viability counts. A series of controls were conducted in parallel where reaction components were replaced with an identical volume of PBS instead.

TABLE 1

|  | Control 1 | Control 2 | Control 3 | Control 4 | Test Reaction |
|---|---|---|---|---|---|
| 500 µL blood | √ |  | √ |  | √ |
| 100 µL E. faecalis | √ | √ |  | √ | √ |
| 100 µL PlyV12 |  | √ |  |  | √ |
| Bacterial counts (CFU/mL) | $10^7$ | 0 | 0 | $10^7$ | $10^6$ |

TABLE 1-continued

| | Control 1 | Control 2 | Control 3 | Control 4 | Test Reaction |
|---|---|---|---|---|---|

Binding Epitope Analysis

Structurally, lysins are commonly found as modular proteins with an amino terminal domain that confers the enzymatic activity for a peptidoglycan bond and a carboxy terminal domain that confers binding specificity to a carbohydrate epitope in the bacterial cell wall. The nature of the PlyV12 binding epitope on the surface of E. faecalis V12 may be delineated by several experiments. First, pronase treated whole E. faecalis V12 remains susceptible to PlyV12 as measured by both OD and viability assays (FIG. 11), suggesting that the PlyV12 binding epitope is not a protein. Second, sodium periodate treated whole E. faecalis V12 is no longer susceptible to the lytic action of PlyV12 as observed by OD assay. While sodium periodate treatment of whole bacteria oxidizes the carbohydrates on the surface thereby affecting the viability of E. faecalis, it does not result in visible cell lysis. For this reason, sodium periodate experiments are preferably monitored by OD and not viability assays. Lastly, E. faecalis V12 surface carbohydrates extracted by a nitrous acid extraction method inhibit PlyV12 lytic activity, confirmed by both OD and viability assays. Taken together, the results strongly point to the PlyV12 binding epitope on the surface of E. faecalis being carbohydrate in nature.

Figure 11:
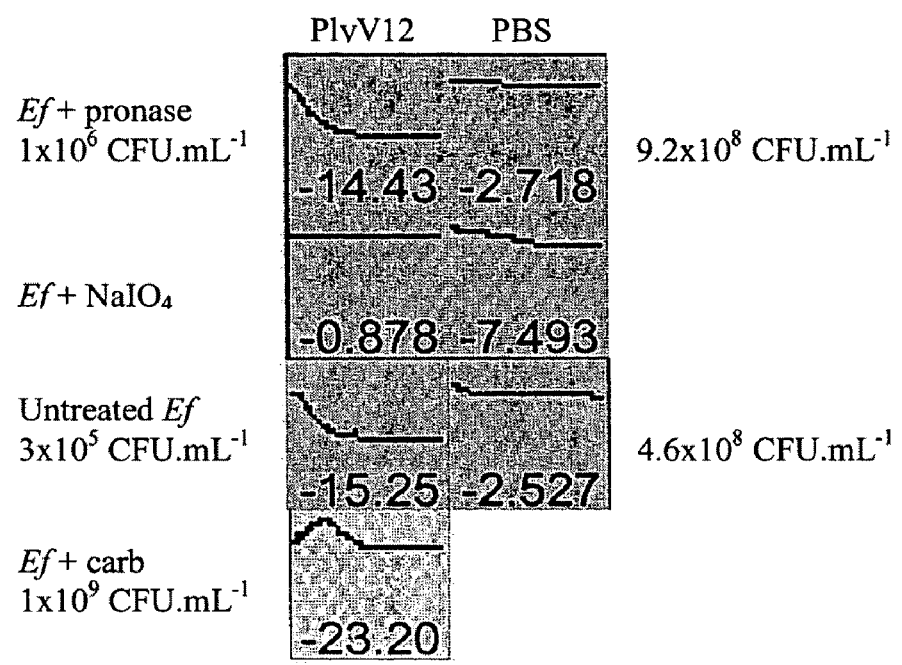
FIG. 11 are graphs showing the effect of PlyV12 on pronase treated, sodium periodate ($NaIO_4$) treated and untreated E. faecalis V12 as observed by 15 minute OD assays (left panels), control reactions with PBS instead of PlyV12 (right panels) and an inhibition assay of PlyV12 lytic activity on E. faecalis V12 by V12 extracted surface carbohydrates (bottom panel).

FIG. 11 summarizes experiments indicating the binding epitope of PlyV12 on the surface of E. faecalis V12 to be carbohydrate in nature. The effect of PlyV12 on pronase treated, sodium periodate ($NaIO_4$) treated and untreated E. faecalis V12 as observed by 15 minute OD assays are shown on the left panels. Control reactions with PBS instead of PlyV12 are shown on the right panels. An inhibition assay of PlyV12 lytic activity on E. faecalis V12 by V12 extracted surface carbohydrates is shown on the bottom. Where viability assays were carried out, the bacterial counts after 15 minute incubation were listed adjacent to the corresponding reaction. The number below each graph is the Vmax value, which represents the change in optical density per unit time.

Mouse Models of E. faecalis Colonization and Infections

Gastrointestinal Colonization with E. faecalis

No antibiotic regiment is believed to be successful in the decolonization of antibiotic resistant enterococci from the gastrointestinal tract (Harbarth, S., S. Cosgrove, and Y. Carmeli, "Effects of antibiotics on nosocomial epidemiology of vancomycin-resistant enterococci," Antimicrob. Agents Chemother. 46, pp. 1619-1628 (2002)). Therefore, a mouse model of E. faecalis colonization is useful to determine if decolonization can be achieved with PlyV12. Endogenous enterococci are isolated from the fecal matter of BALB/c mice at an average of $6.5 \times 10^7$ CFU $g^{-1}$.

Figure 12B:
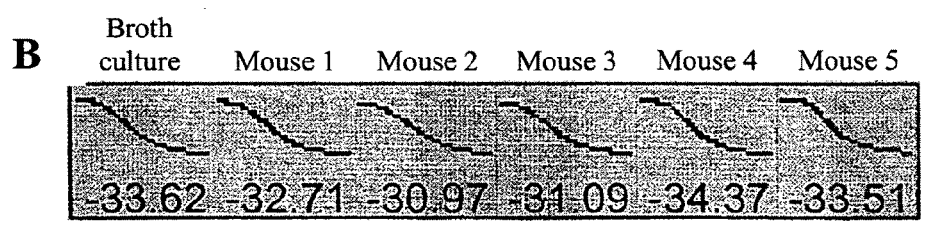
FIG. 12B shows the changes in $OD_{600}$ over a 20 minute period of mouse passaged E. faecalis V12S to PlyV12, as well as the susceptibility of a laboratory culture of E. faecalis V12S to PlyV12 as a control.

FIGS. 12A and 12B show a comparison of the susceptibility of mouse gastrointestinal passaged E. faecalis V12S and endogenous mouse enterococci to PlyV12. Equal volumes of enterococcal suspensions and PlyV12 were analyzed in OD assays. FIG. 12A shows the susceptibility of endogenous enterococci isolated from fecal samples of five BALB/c mice to PlyV12. FIG. 12B shows the susceptibility of mouse passaged E. faecalis V12S to PlyV12, as well as the susceptibility of a laboratory culture of E. faecalis V12S to PlyV12 as a control. Both panels show changes in $OD_{600}$ over a 20-minute period. The number below each graph is the Vmax value, which represents the change in optical density per unit time.

The enterococci endogenous to BALB/c mice were sensitive to streptomycin, but not highly susceptible to PlyV12 lytic activity (FIG. 12A). Thus, for a model of eradicating gastrointestinal colonization of enterococci, endogenous mouse enterococci are preferably replaced by an enterococcal strain that is highly susceptible to PlyV12. Water containing 5 mg/mL streptomycin successfully eliminates endogenous enterococci isolated from mouse fecal matter. Following pretreatment of mice with streptomycin containing water for a week, mice were fed E. faecalis V12S strain V12 (selected for resistance to streptomycin) in their drinking water. E. faecalis V12S suspended in water survived for up to 3 days with no appreciable drop in viability, although the suspension is only left in mouse cages for 1 day. The mice were successfully colonized with E. faecalis V12S, which remained susceptible to PlyV12 lytic action even after passaging through the gastrointestinal tracts of mice and retrieved from their fecal matter (FIG. 12B). Streptomycin-resistant enterococci were retrieved from the fecal matter of colonized mice at an average of $1 \times 10^6$ $CFUg^{-1}$ and testing was carried out for up to the 8 days. The E. faecalis V12S colonized mice refused to drink purified PlyV12 at 30 units/mL left in their cages despite withholding of all fluids for 10 hours prior.

E. faecalis Septicemia Model

Figure 13:
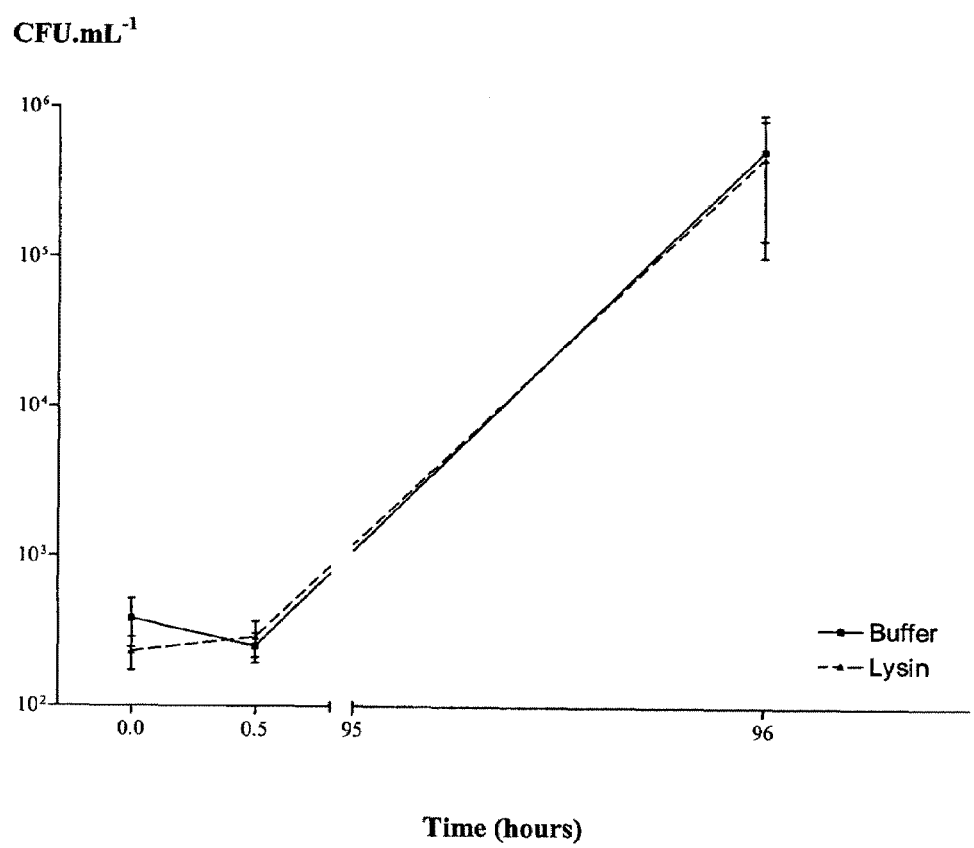
FIG. 13 is a graph showing Enterococcal counts in blood of mice infected with E. faecalis V12 through the intravenous route, followed by treatment with buffer or PlyV12.

FIG. 13 shows Enterococcal counts in blood of mice infected with E. faecalis V12 through the intravenous route, followed by treatment with buffer or PlyV12. This graph demonstrates the colony forming units (CFU) of E. faecalis per milliliter of mouse blood taken at different time points represented in hours. The 0 time point represents the time at which the mice were treated with 100 or 200 μL of either sterile buffer or purified PlyV12 at 30 units/mL, which was 48 hours post infection with $6.5 \times 10^3$ CFU of E. faecalis V12. To obtain the data shown in FIG. 13, blood counts were carried out again at 30 minutes and 4 days post treatment. Sixteen mice were used in the buffer treated group, while 18 mice were used in the PlyV12 treated group. Septicemia was confirmed by the presence of enterococci in blood 48 hours post infection with $6.5 \times 10^8$ CFU E. faecalis V12 injected into the tail vein of each BALB/c mouse. At that time, enterococcal counts were typically on the order of $10^2$ to $10^3$ CFU/mL of blood (FIG. 13, time point 0). At 48 hours post infection, mice are injected with 100 or 200 μL of either purified PlyV12 at 30 units/mL, or sterile buffer into its tail vein. Enterococcal counts in mouse blood were conducted 30 minutes and 4 days post treatment. The 30 minute and day 4 counts of both lysin and buffer treated mice were comparable at an average of $2.65 \times 10^2$ and $5 \times 10^5$ CFU/mL respectively (FIG. 13). The day 4 counts range from undetectable to 106, but the numbers do not always correlate with the state of wellbeing of each mouse. Over the course of a week, the infected mice appeared ill, losing almost 30% of their original body weight and having ruffled fur, although the mortality rate was less than 20%. The number of deaths is comparable between both groups. Data from animals that died is not included in the graph.

E. faecalis Peritonitis Model

In this model, each mouse was injected with 109 CFU E. faecalis V12 in 100 μL mixed with an equal volume of sterile rat fecal extract (SFRE) into the peritoneal cavity. Other studies have shown that injection of SRFE with the enterococcal inoculum lowers the dose that kills 50% of animals ($LD_{50}$) by a log. By this method, the $LD_{50}$ of E. faecalis V12 was estimated at $10^9$ CFU in 24 hours. PlyV12 treatment of mice did not reduce the numbers of mouse deaths, or prolong the lives of mice when compared with the untreated group. Nine mice were used in each group. PlyV12 remained active in the presence of 50% SRFE, while the injection of SRFE itself into the peritoneal cavity of mice had no adverse effect on the mice.

Mutagenesis of PlyV12

Selection for Increased PlyV12 Lytic Activity Against *E. faecalis*

*E. coli* XL1-Red is a commercially available strain that is deficient in three of the primary DNA repair pathways. The random mutation rate in this triple mutant is estimated to be 5,000-fold higher than that of an isogenic strain of wildtype *E. coli*. Random mutagenesis of the plyV12 gene is achieved by passaging the pBAD24-lysin2 plasmid through *E. coli* XL1-Red overnight. The mutagenized plasmids may be transformed into *E. coli* XL1-Blue for selection of mutants that may express a more active lytic enzyme manifesting itself by way of a larger zone of *E. faecalis* clearing than the wildtype plasmid clone in an *E. faecalis* overlay assay. At least three thousand colonies may be screened, with 46 clones selected for further examination. However, a side-by-side overlay assay of the wildtype clone and the 46 selected mutant clones revealed comparable zones of clearing. A mutated version of PlyV12 with higher lytic activity than wildtype PlyV12 was not identified in this approach.

Selection for Increased PlyV12 Lytic Activity Against *S. aureus*

PlyV12 had some lytic effect on several *S. aureus* strains tested, with the most pronounced activity on strain RN6390 (FIG. 9A). *S. aureus* strain RN4220, a strain less susceptible to PlyV12 than RN6390, was subjected to a viability assay upon incubation with PlyV12 at 25 units/mL for 15 minutes and 1 hour. The lytic effect of PlyV12 was confirmed as *S. aureus* RN4220 viability decreased by over a log after 15 minutes and almost 2-logs after one hour incubation with purified PlyV12. A library of XL1-Red mutated plyV12, as above, was screened against *S. aureus* RN6390 for increased lytic activity by way of a larger zone of clearing than unmutated plyV12, but such a clone was not identified.

The Fusion of the PlyV12 Binding Domain with the Catalytic Domain of PlyG

The fusion between the PlyG catalytic domain and the PlyV12 binding domain amplified from both plyV12 and plyV12CO were carried out successfully, with the resulting fusion genes under the control of the arabinose promoter of pBAD24. The clones were confirmed to be correct by DNA sequencing. There was evidence that fusion clones induced for as little as 4 hours, as well as those induced overnight lysed in culture, suggesting that the fusion protein is toxic to *E. coli* DH5α. The fusion clones were induced for shorter periods of time, between 30 minutes and 3 hours, in hope of circumventing its toxic effect against *E. coli*. Both the culture supernatants and cell lysates from different induction times did not produce any detectable lytic activity against *E. faecalis* tested by the OD assay.

Variant Polypeptides

In addition to the lysins encoded by polypeptide sequences of SEQ ID NO: 1, the present disclosure also provides certain variant polypeptides, including fragments thereof and polypeptides with certain substitutions. The modified or altered form of the protein or peptides and peptide fragments, as disclosed herein, includes protein or peptides and peptide fragments that are chemically synthesized or prepared by recombinant DNA techniques, or both. These techniques include, for example, chimerization and shuffling. Peptide variants also include fragments of a polypeptide. When the protein or peptide is produced by chemical synthesis, it is preferably substantially free of chemical precursors or other chemicals, i.e., it is separated from chemical precursors or other chemicals that are involved in the synthesis of the protein. Accordingly such preparations of the protein have less than about 30%, 20%, 10%, 5% (by dry weight) of chemical precursors or compounds other than the polypeptide of interest.

A "variant polypeptide sequence phage associated lytic enzyme" is preferably an active lytic enzyme polypeptide having at least about 80% amino acid sequence identity with a full-length native sequence lytic enzyme polypeptide sequence as disclosed herein. Such lytic enzyme polypeptide variants include, for instance, lytic enzyme polypeptides wherein one or more amino acid residues are added, or deleted, at the N- or C-terminus of the full-length native amino acid sequence. Preferably, a lytic enzyme polypeptide variant will have at least about 80% amino acid sequence identity, preferably at least about 81%, 82%, 83%, 84%, 85%, 86%, 87%, 88%, 89%, 90%, 91%, 92%, 93%, 94%, 95%, 96%, 97%, 98%, 99%, or 99.5% amino acid sequence identity with a full-length native sequence lytic enzyme polypeptide sequence as disclosed herein, a lytic enzyme polypeptide sequence lacking the signal peptide as disclosed herein, an extracellular domain of a lytic enzyme polypeptide, with or without the signal peptide, as disclosed herein or any other specifically defined fragment of a full-length lytic enzyme polypeptide sequence as disclosed herein. Preferably, lytic enzyme variant polypeptides are at least about 10 amino acids in length, often at least about 20, 30, 40, 50, 60, 70, 80, 90, 100, 150, 200 or 300 amino acids in length, or more.

Such phage associated lytic enzyme variants include, for instance, lytic enzyme polypeptides wherein one or more amino acid residues are added, or deleted at the N or C terminus of the sequence of SEQ ID No. 1. In an embodiment one or more amino acids are substituted, deleted, and/or added to any position(s) in the sequence, or sequence portion.

"Percent amino acid sequence identity" with respect to the phage associated lytic enzyme sequences identified herein is defined as the percentage of amino acid residues in a candidate sequence that are identical with the amino acid residues in the phage associated lytic enzyme sequence, after aligning the sequences in the same reading frame and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, such as using publicly available computer software such as blast software.

Polypeptide alignment for purposes of determining percent amino acid sequence identity can be achieved in various ways that are within the skill in the art, for instance using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

The percent amino acid sequence identity values may also be obtained as described below by using the WU-BLAST-2 computer program (Altschul et al., Methods in Enzymology 266:460-480 (1996)). Most of the WU-BLAST-2 search parameters are set to the default values. Those not set to default values are set with the following values: overlap span=1, overlap fraction=0.125, word threshold (T)=11, and scoring matrix=BLOSUM62. When WU-BLAST-2 is employed, a percent amino acid sequence identity value is determined by dividing (a) the number of matching identical amino acid residues between the amino acid sequence of the lytic enzyme polypeptide of interest having a sequence derived from the native lytic enzyme polypeptide and the comparison amino acid sequence of interest (i.e., the sequence against which the lytic enzyme polypeptide of interest is being compared which may be a lytic enzyme variant polypeptide) as determined by WU-BLAST-2 by (b) the total number of amino acid residues of the lytic enzyme polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the lytic enzyme polypeptide of interest.

Percent amino acid sequence identity may also be determined using the sequence comparison program NCBI-BLAST2 (Altschul et al., Nucleic Acids Res. 25:3389-3402 (1997)). The NCBI-BLAST2 sequence comparison program may be downloaded from http://www.ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the percent amino acid sequence identity of a given amino acid sequence A to, with, or against a given amino acid sequence B (which can alternatively be phrased as a given amino acid sequence A that has or comprises a certain percent amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated-that where the length of amino acid sequence A is not equal to the length of amino acid sequence B, the percent amino acid sequence identity of A to B will not equal the percent amino acid sequence identity of B to A.

Lysin Fragments

In some embodiments, biologically active fragments of the lysins, including the polypeptide sequences such as SEQ ID NO: 1 or variants thereof described herein, are provided. As used herein, a "fragment" is a polypeptide variant having an amino acid sequence that entirely is the same as part but not all of the amino acid sequence of the aforementioned polypeptides. A fragment may be "free-standing," or comprised within a larger polypeptide of which they form a part or region, most preferably as a single continuous region, a single larger polypeptide.

Biologically active portions of a protein or peptide fragment of the embodiments, as described herein, include polypeptides comprising amino acid sequences sufficiently identical to or derived from the amino acid sequence of the phage protein of the disclosure, which include fewer amino acids than the full length protein of the phage protein and exhibit at least one activity of the corresponding full length protein. Typically, biologically active portions comprise a domain or motif with at least one activity of the corresponding protein. A biologically active portion of a protein or protein fragment of the disclosure can be a polypeptide which is, for example, 10, 25, 50, 100 less or more amino acids in length. Moreover, other biologically active portions, in which other regions of the protein are deleted, or added can be prepared by recombinant techniques and evaluated for one or more of the functional activities of the native form of a polypeptide of the embodiments.

Fragments may include, for example, truncation polypeptides having a portion of an amino acid sequence corresponding to (e.g., 50% sequence identity, more preferably at least 60% more preferably, at least 70% sequence identity, more preferably at least 80% sequence identity, more preferably at least 95% sequence identity, more preferably at least 97% sequence identity and even more preferably at least or even 98% sequence identity of at least 50 amino acid long region of the Natural Binding Region, or of variants thereof, such as a continuous series of residues that includes the amino terminus, or a continuous series of residues that includes the carboxyl terminus. Degradation forms of the polypeptides of this embodiment in a host cell are also provided in some embodiments. Further provided are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also provided are fragments that have binding activities of at least $10^6$, $10^7$, $10^8$ or $10^9$ against *Enterococcus* bacteria, including those with a similar activity or an improved activity, or with a decreased undesirable activity. Also advantageous are conjugates of binding site and a detectable tag or bacteriocidal tag that confers such desirable clinical function whereby the binding region specifically binds to a bacterial wall.

Variants that are fragments of the polypeptides of the disclosure may be employed for producing the corresponding full-length polypeptide by peptide synthesis; therefore, these variants may be employed as intermediates for producing the full-length polypeptides of embodiments of the disclosure.

Lytic enzyme peptide fragments may be prepared by any of a number of conventional techniques. Desired peptide fragments may be chemically synthesized. An alternative approach involves generating lytic enzyme fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, lytic enzyme polypeptide fragments share at least one biological and/or immunological activity with the native lytic enzyme polypeptide disclosed herein.

For example, libraries of fragments of the coding sequence of a polypeptide of the disclosure can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N terminal and internal fragments of various sizes of the protein of interest. Several techniques are known in the art for screening gene products of combinatorial libraries made by point mutations or truncation, and for screening cDNA libraries for gene products having a selected property. The most widely used techniques, which are amenable to high through put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the disclosure (Arkin and Yourvan (1992) Proc. Natl. Acad. Sci. USA 89:7811 7815; Delgrave et al. (1993) Protein Engineering 6(3):327 331).

Immunologically active portions of a protein or peptide fragment can include regions that bind to antibodies that recognize the phage enzyme. In this context, the smallest portion of a protein (or nucleic acid that encodes the protein) according to embodiments is an epitope that is recognizable as specific for the phage that makes the lysin protein. Accordingly, the smallest polypeptide (and associated nucleic acid that encodes the polypeptide) that can be expected to bind antibody and is useful for some embodiments may be 8, 9, 10, 11, 12, 13, 15, 20, 25, 30, 35, 40, 45, 50, 55, 60, 65, 75, 85, or 100 amino acids long. Although small sequences as short as 8, 9,10, 11, 12 or 15 amino acids long reliably comprise enough structure to act as epitopes, shorter sequences of 5, 6, or 7 amino acids long can exhibit epitopic structure in some conditions and have value in an embodiment. Thus, in some embodiments, the smallest portion of the protein described by SEQ ID No. 1 can includes polypeptides as small as 5, 6, 7, 8, 9, or 10 amino acids long.

Homologous proteins and nucleic acids can be prepared that share functionality with such small proteins and/or nucleic acids (or protein and/or nucleic acid regions of larger molecules) as will be appreciated by a skilled artisan. Such small molecules and short regions of larger molecules, that may be homologous specifically are intended as embodiments. Preferably the homology of such valuable regions is at least 50%, 65%, 70%, 75%, 80%, 85%, and more preferably at least 90%, 95%, 97%, 98%, or at least 99% compared to SEQ ID No. 1. These percent homology values do not include alterations due to conservative amino acid substitutions.

An epitope as described herein may be used to generate an antibody and also can be used to detect binding to molecules that recognize the lysin protein. Another embodiment is a molecule such as an antibody or other specific binder that may be created through use of an epitope such as by regular immunization or by a phase display approach where an epitope can be used to screen a library if potential binders. Such molecules recognize one or more epitopes of lysin protein or a nucleic acid that encodes lysin protein. An antibody that recognizes an epitope may be a monoclonal antibody, a humanized antibody, or a portion of an antibody protein. Desirably the molecule that recognizes an epitope has a specific binding for that epitope which is at least 10 times as strong as the molecule has for serum albumin. Specific binding can be measured as affinity (Km). More desirably the specific binding is at least $10^2$, $10^3$, $10^4$, $10^5$, $10^6$, $10^7$, $10^8$, or even higher than that for serum albumin under the same conditions.

In one example, the antibody or antibody fragment is in a form useful for detecting the presence of the lysin protein. A variety of forms and methods for their synthesis are known as will be appreciated by a skilled artisan. The antibody may be conjugated (covalently complexed) with a reporter molecule or atom such as a fluor, an enzyme that creates an optical signal, a chemilumiphore, a microparticle, or a radioactive atom. The antibody or antibody fragment may be synthesized in vivo, after immunization of an animal, for example. The antibody or antibody fragment may be synthesized via cell culture after genetic recombination. The antibody or antibody fragment may be prepared by a combination of cell synthesis and chemical modification.

Variant Polypeptides

Substitutional variants are those in which at least one residue in the amino acid sequence has been removed and a different residue inserted in its place. Such substitutions may be made in accordance with the following Table 2 when it is desired to finely modulate the characteristics of the protein. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Table 2 shows amino acids which may be substituted for an original amino acid in a protein and which are regarded as conservative substitutions.

TABLE 2

| Original Residue | Conservative Substitutions |
| --- | --- |
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than in Table 2, i.e., selecting residues that differ more significantly in their effect on maintaining: (a) the structure of the polypeptide backbone in the area of the substitution, for example, as a sheet or helical conformation; (b) the charge or hydrophobicity of the molecule at the target site; or (c) the bulk of the side chain. The substitutions which in general are expected to produce the greatest changes in protein properties will be those in which: (a) a hydrophilic residue (e.g., seryl or threonyl) is substituted for (or by) a hydrophobic residue (e.g., leucyl, isoleucyl, phenylalanyl, valyl or alanyl); (b) a cysteine or proline is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain, (e.g., phenylalanine), is substituted for (or by) one not having a side chain (e.g., glycine).

The effects of these amino acid substitutions or deletions or additions may be assessed for derivatives of the lytic protein by analyzing the ability of the derivative proteins to complement the sensitivity to DNA cross-linking agents exhibited by phages in infected bacteria hosts. These assays may be performed by transfecting DNA molecules encoding the derivative proteins into the bacteria as described above. Substantial modifications in function or immunological identity of the lytic enzyme polypeptide may be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Non-conservative substitutions will entail exchanging a member of one of these classes for another class. Such substituted residues also may be introduced into the conservative substitution sites or, more preferably, into the remaining (non-conserved) sites.

Polypeptide variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the lytic enzyme variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, Science. 244: 1081-1085 (1989)]. Alanine is also typically preferred because it is the most common amino acid. Further, it is frequently found in both buried and exposed positions [Creighton, The Proteins, (W. H. Freeman & Co., N.Y.); Chothia, J. Mol. Biol. 150:1 (1976)]. If alanine substitution does not yield adequate amounts of variant, an isoteric amino acid can be used.

Chimeric Fusion Proteins

In some embodiments, a lysin may also be modified to form a chimeric molecule comprising a lytic enzyme fused to another, heterologous polypeptide or amino acid sequence. A "chimeric protein" or "fusion protein" comprises all or (preferably a biologically active) part of a polypeptide of the disclosure operably linked to a heterologous polypeptide. Chimeric proteins or peptides are produced, for example, by combining two or more proteins having two or more active sites. Chimeric protein and peptides can act independently on the same or different molecules, and hence have a potential to treat two or more different bacterial infections at the same time. Chimeric proteins and peptides are also used to treat a bacterial infection by cleaving the cell wall in more than one location.

In one example, such a chimeric molecule comprises a fusion of the lytic enzyme with a tag polypeptide which provides an epitope to which an anti-tag antibody can selectively bind. The epitope tag is generally placed at the amino- or carboxyl-terminus of the lytic enzyme. The presence of such epitope-tagged forms of the lytic enzyme may be detected using an antibody against the tag polypeptide. Also, provision of the epitope tag enables the lytic enzyme to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)1; and the Herpes Simplex virus glycoprotein D (gD) tag and its antibody [Paborsky et al., Protein Engineering: (6):547-553 (1990)]. Other tag polypeptides include the Flag-peptide [Hopp et al., BioTechnology, 6:1204-1210 (1988)]; the KT3 epitope peptide [Martin et al., Science 255: 192-194 (1992)]; an □-tubulin epitope peptide (Skinner et al., J. Biol. Chem., 266:15163-15166 (1991)1; and the T7 gene 10 protein peptide tag (Lutz-Freyermuth et al., Proc. Natl. Acad. Sci. USA, 87:6393-6397 (1990)].

In an alternative embodiment, the chimeric molecule may comprise a fusion of the lytic enzyme with an immunoglobulin or a particular region of an immunoglobulin. For a bivalent form of the chimeric molecule (also referred to as an "immunoadhesin"), such a fusion could be to the Fc region of an IgG molecule. The Ig fusions may include the substitution of a soluble (transmembrane domain deleted or inactivated) form of a lytic enzyme polypeptide in place of at least one variable region within an Ig molecule. The immunoglobulin fusion may include the hinge, CH2 and CH3, or the hinge, CH1, CH2 and CH3 regions of an IgG1 molecule. For the production of immunoglobulin fusions see also U.S. Pat. No. 5,428, 130 issued Jun. 27, 1995.

In another example, the chimeric protein or peptide contains a heterologous signal sequence at its N terminus. For example, the native signal sequence of a polypeptide of the disclosure can be removed and replaced with a signal sequence from another protein. For example, the gp67 secretory sequence of the baculovirus envelope protein can be used as a heterologous signal sequence (Current Protocols in Molecular Biology, Ausubel et al., eds., John Wiley & Sons, 1992, incorporated herein by reference). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

Another example of a useful fusion protein is a GST fusion protein in which the polypeptide of the disclosure is fused to the C terminus of a GST sequence. Such a chimeric protein can facilitate the purification of a recombinant polypeptide of the disclosure.

Another example shows an immunoglobulin fusion protein in which all or part of a polypeptide of the disclosure is fused to sequences derived from a member of the immunoglobulin protein family. An immunoglobulin fusion protein can be incorporated into a pharmaceutical composition and administered to a subject to inhibit an interaction between a ligand (soluble or membrane bound) and a protein on the surface of a cell (receptor), to thereby suppress signal transduction in vivo. The immunoglobulin fusion protein can alter bioavailability of a cognate ligand of a polypeptide of the disclosure. Inhibition of ligand/receptor interaction may be useful therapeutically, both for treating bacterial associated diseases and disorders for modulating (i.e., promoting or inhibiting) cell survival. Moreover, an immunoglobulin fusion protein of the disclosure can be used as an immunogen to produce antibodies directed against a polypeptide of the disclosure in a subject, to purify ligands and in screening assays to identify molecules which inhibit the interaction of receptors with ligands. Chimeric and fusion proteins and peptides of the disclosure can be produced by standard recombinant DNA techniques.

In another embodiment, the fusion gene can be synthesized by conventional techniques, including automated DNA synthesizers. Alternatively, PCR amplification of gene fragments can be carried out using anchor primers which give rise to complementary overhangs between two consecutive gene fragments which subsequently can be annealed and reamplified to generate a chimeric gene sequence (see, i.e., Ausubel et al., supra). Moreover, many expression vectors are commercially available that already encode a fusion moiety (i.e., a GST polypeptide). A nucleic acid encoding a polypeptide of the disclosure can be cloned into such an expression vector such that the fusion moiety is linked in frame to the polypeptide of the disclosure.

Combination with Signal Sequences

In one embodiment of the disclosure, a signal sequence of a polypeptide of can facilitate transmembrane movement of the protein and peptides and peptide fragments of the disclosure to and from mucous membranes, as well as by facilitating secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the disclosure can pertain to the described polypeptides having a signal sequence, as well as to the signal sequence itself and to the polypeptide in the absence of the signal sequence (i.e., the cleavage products). In one embodiment, a nucleic acid sequence encoding a signal sequence of the disclosure can be operably linked in an expression vector to a protein of interest, such as a protein which is ordinarily not secreted or is otherwise difficult to isolate. The signal sequence directs secretion of the protein, such as from an eukaryotic host into which the expression vector is transformed, and the signal sequence is subsequently or concurrently cleaved. The protein can then be readily purified from the extracellular medium by art recognized methods. Alternatively, the signal sequence can be linked to a protein of interest using a sequence, which facilitates purification, such as with a GST domain.

In another example, a signal sequence can be used to identify regulatory sequences, i.e., promoters, enhancers, repressors. Since signal sequences are the most amino terminal sequences of a peptide, it is expected that the nucleic acids which flank the signal sequence on its amino terminal side will be regulatory sequences that affect transcription. Thus, a nucleotide sequence which encodes all or a portion of a signal sequence can be used as a probe to identify and isolate the signal sequence and its flanking region, and this flanking region can be studied to identify regulatory elements therein. The present disclosure also pertains to other variants of the polypeptides of the disclosure. Such variants have an altered amino acid sequence which can function as either agonists (mimetics) or as antagonists. Variants can be generated by mutagenesis, i.e., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein. Variants of a protein of the disclosure which function as either agonists (mimetics) or as antagonists can be identified by screening combinatorial libraries of mutants, i.e., truncation mutants, of the protein of the disclosure for agonist or antagonist activity. In one example, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (i.e., for phage display). There are a variety of methods which can be used to produce libraries of potential variants of the polypeptides of the disclosure from a degenerate oligonucleotide sequence. Methods for synthesizing degenerate oligonucleotides are known in the art (see, i.e., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477, all herein incorporated by reference).

Shuffled Enzymes

Certain examples provide shuffled proteins or peptides comprising one or more lytic enzyme peptides or variants thereof disclosed herein, gene products, or peptides for more than one related phage protein or protein peptide fragments that are randomly cleaved and reassembled into a more active or specific protein. Shuffled oligonucleotides, peptides or peptide fragment molecules are selected or screened to identify a molecule having a desired functional property. This method is described, for example, in Stemmer, U.S. Pat. No. 6,132,970 (Method of shuffling polynucleotides); Kauffman, U.S. Pat. No. 5, 976,862 (Evolution via Condon based Synthesis) and Huse, U.S. Pat. No. 5,808,022 (Direct Codon Synthesis). The contents of these patents are incorporated herein by reference. Shuffling is used to create a protein that is 10 to 100 fold more active than the template protein. The template protein is selected among different varieties of lysin or holin proteins. The shuffled protein or peptides constitute, for example, one or more binding domains and one or more catalytic domains. Each binding or catalytic domain is derived from the same or a different phage or phage protein. The shuffled domains are either oligonucleotide based molecules, as gene or gene products, that either alone or in combination with other genes or gene products are translatable into a peptide fragment, or they are peptide based molecules. Gene fragments include any molecules of DNA, RNA, DNA RNA hybrid, antisense RNA, Ribozymes, ESTs, SNIPs and other oligonucleotide based molecules that either alone or in combination with other molecules produce an oligonucleotide molecule capable or incapable of translation into a peptide.

Covalent Modification of Polypeptides

Other examples provide for covalent modifications of a lytic enzyme, or fragment or variant thereof. One type of covalent modification includes reacting targeted amino acid residues of a lytic enzyme polypeptide with an organic derivatizing agent that is capable of reacting with selected side chains or the N- or C-terminal residues of the lytic enzyme— Derivatization with bifunctional agents is useful, for instance, for crosslinking lytic enzyme to a water-insoluble support matrix or surface for use in the method for purifying anti-lytic enzyme antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl-)dithiolpropioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the □-amino groups of lysine, arginine, and histidine side chains [T. E. Creighton, Proteins: Structure and Molecular Properties, W. H. Freeman & Co., San Francisco, pp 79-86 (1983)], acetylation of the N-terminal amine, and amidation of any C-terminal carboxyl group.

Another type of covalent modification of the lytic enzyme polypeptide provided herein comprises altering the native glycosylation pattern of the polypeptide. Altering the native glycosylation pattern is intended for purposes herein to mean deleting one or more carbohydrate moieties found in native sequence lytic enzyme (either by removing the underlying glycosylation site or by deleting the glycosylation by chemical and/or enzymatic means), and/or adding one or more glycosylation sites that are not present in the native sequence lytic enzyme. In addition, the phrase includes qualitative changes in the glycosylation of the native proteins, involving a change in the nature and proportions of the various carbohydrate moieties present.

Addition of glycosylation sites to the lytic enzyme polypeptide may be accomplished by altering the amino acid sequence. The alteration may be made, for example, by the addition of, or substitution by, one or more serine or threonine residues to the native sequence lytic enzyme (for O-linked glycosylation sites). The lytic enzyme amino acid sequence may optionally be altered through changes at the DNA level, particularly by mutating the DNA encoding the lytic enzyme polypeptide at preselected bases such that codons are generated that will translate into the desired amino acids.

Another means of increasing the number of carbohydrate moieties on the lytic enzyme polypeptide is by chemical or enzymatic coupling of glycosides to the polypeptide. Such methods are described in the art, e.g., in WO 87/05330 published Sep. 11, 1987, and in Aplin and Wriston, CRC Crit. Rev. Biochem., pp. 259-306 (1981).

Removal of carbohydrate moieties present on the lytic enzyme polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification of lytic enzyme comprises linking the lytic enzyme polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

Holin Proteins

The present disclosure also provides the use of holin proteins, for example in combination with one or more lytic enzyme peptides, or variants or fragments thereof. Holin proteins produce holes in the cell membrane. Holin proteins, or "holins," can form lethal membrane lesions. Like the lytic proteins, holin proteins are coded for and carried by a phage. Most holin protein sequences are short, and overall, hydrophobic in nature, with a highly hydrophilic carboxy terminal domain. In many cases, the putative holin protein is encoded on a different reading frame within the enzymatically active domain of the phage. In other cases, holin protein is encoded on the DNA next or close to the DNA coding for the cell wall lytic protein. Holin proteins are frequently synthesized during the late stage of phage infection and found in the cytoplasmic membrane where they cause membrane lesions.

Holins can be grouped into two general classes based on primary structure analysis. Class I holins are usually 95 residues or longer and may have three potential transmembrane domains. Class II holins are usually smaller, at approximately 65 95 residues, with the distribution of charged and hydrophobic residues indicating two TM domains (Young, et al. Trends in Microbiology v. 8, No. 4, March 2000). At least for the phages of gram positive hosts, however, the dual component lysis system may not be universal. Although the presence of holins has been shown or suggested for several phages, no genes have yet been found encoding putative holins for all phages. Holins have been shown to be present in several bacteria, including, for example, lactococcal bacteriophage Tuc2009, lactococcal NLC3, pneumococcal bacteriophage EJ 1, Lacto*Bacillus* gasseri bacteriophage Nadh, *Staphylococcus aureus* bacteriophage Twort, *Listeria monocytogenes* bacteriophages, pneumococcal phage Cp 1, *Bacillus subtillis* phage M29, Lacto*Bacillus* delbrueckki bacteriophage LL H lysin, and bacteriophage N11 of *Staphyloccous aureus*. (Loessner, et al., Journal of Bacteriology, Aug. 1999, p. 4452 4460).

Polynucleotides

A lysin may be produced by any number of different methods. The lytic enzyme is produced by infecting said *Enterococcus* bacteria with the genetic code delivered by a bacteriophage specific for said *Enterococcus* bacteria. In another example of the disclosure, the lytic enzyme is produced by recombinant production from a nucleic acid that comprises a DNA having the sequence of bases of a polynucleotide sequence coding for one or more polypeptides of SEQ ID NO: 1 or a sequence that hybridizes with the complement of bases of a polynucleotide sequence coding for the polypeptide sequences of SEQ ID NO: 1 under suitable hybridization conditions. The lytic enzyme may be produced by removing a gene for the lytic enzyme from the phage genome, introducing said gene into a transfer vector, and cloning said transfer vector into an expression system., wherein the transfer vector is a plasmid. The expression system may be a bacteria, selected from any of the above listed groups, or, from *E. coli*. In another expression system production of the enzyme is by cell free expression system. In one particularly preferred embodiment, the invention provides the polynucleotide sequence of PlyV12 deposited into GenBank under accession number AY581208.

In addition to the full-length native polynucleotide sequences encoding lytic enzyme polypeptides described herein, it is contemplated that lytic enzyme variants can be prepared. The degeneracy of the genetic code further widens the scope of the examples as it enables major variations in the nucleotide sequence of a DNA molecule while maintaining the amino acid sequence of the encoded protein. For example, a representative amino acid residue is alanine. This may be encoded in the cDNA by the nucleotide codon triplet GCT. Because of the degeneracy of the genetic code, three other nucleotide codon triplets—GCT, GCC and GCA—also code for alanine. Thus, the nucleotide sequence of the gene could be changed at this position to any of these three codons without affecting the amino acid composition of the encoded protein or the characteristics of the protein. The genetic code and variations in nucleotide codons for particular amino acids are well known to the skilled artisan. Based upon the degeneracy of the genetic code, variant DNA molecules may be derived from the cDNA molecules disclosed herein using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are herein comprehended by this disclosure.

Lytic enzyme variants can be prepared, for example, by introducing appropriate nucleotide changes into the lytic enzyme DNA, and/or by synthesis of the desired lytic enzyme polypeptide. Those skilled in the art will appreciate that amino acid changes may alter post-translational processes of the lytic enzyme, such as changing the number or position of glycosylation sites or altering the membrane anchoring characteristics.

One skilled in the art will recognize that the DNA mutagenesis techniques described here can produce a wide variety of DNA molecules that code for a bacteriophage lysin specific for *Enterococcus* bacteria yet that maintain the essential characteristics of the lytic protein. Newly derived proteins may also be selected in order to obtain variations on the characteristic of the lytic protein, as will be more fully described below. Such derivatives include those with variations in amino acid sequence including minor deletions, additions and substitutions. While the site for introducing an amino acid sequence variation is predetermined, the mutation per se does not need to be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known. Amino acid substitutions are typically of single residues; insertions usually will be on the order of about from 1 to 10 amino acid residues; and deletions will range about from 1 to 30 residues. Deletions or insertions may be in single form, but preferably are made in adjacent pairs, i.e., a deletion of 2 residues or insertion of 2 residues. Substitutions, deletions, insertions or any combination thereof may be combined to arrive at a final construct. Obviously, the mutations that are made in the DNA encoding the protein should not place the sequence out of reading frame and preferably will not create complementary regions that could produce secondary mRNA structure (EP 75,444A).

"Percent nucleic acid sequence identity" with respect to the phage associated lytic enzyme sequences identified herein is defined as the percentage of nucleotides in a candidate sequence that are identical with the nucleotides in the phage associated lytic enzyme sequence, after aligning the sequences and introducing gaps, if necessary, to achieve the maximum percent sequence identity. Alignment for purposes of determining percent nucleic acid sequence identity can be achieved in various ways that are within the scope of those skilled in the art, including but not limited to the use of publicly available computer software.

Having herein provided nucleotide sequences that code for lytic enzyme genetically coded for by a bacteriophage specific for *Enterococcus* bacteria and fragments of that enzyme, correspondingly provided are the complementary DNA strands of the cDNA molecule and DNA molecules which hybridize under stringent conditions to the lytic enzyme cDNA molecule or its complementary strand. Such hybridizing molecules include DNA molecules differing only by minor sequence changes, including nucleotide substitutions, deletions and additions. Also contemplated by this disclosure are isolated oligonucleotides comprising at least a segment of the cDNA molecule or its complementary strand, such as oligonucleotides which may be employed as effective DNA hybridization probes or primers useful in the polymerase chain reaction. Hybridizing DNA molecules and variants on the lytic enzyme cDNA may readily be created by standard molecular biology techniques.

A large variety of isolated cDNA sequences that encode phage associated lysing enzymes and partial sequences that hybridize with such gene sequences are useful for recombinant production of the lysing enzyme. Representative nucleic acid sequences in this context are polynucleotide sequences coding for the polypeptides of SEQ ID NO:1, sequence and sequences that hybridize, under stringent conditions, with complementary sequences of the DNA encoding the FIG. 1 polypeptide sequence. Still further variants of these sequences and sequences of nucleic acids that hybridize with those shown in the Figures are also contemplated for use in production of lysing enzymes according to the disclosure, including natural variants that may be obtained.

The detection of specific DNA mutations may be achieved by methods such as hybridization using specific oligonucleotides (Wallace et al. (1986). Cold Spring Harbor Symp. Quant. Biol. 51:257-261), direct DNA sequencing (Church and Gilbert (1988). Proc. Natl. Acad. Sci. USA 81:1991-1995), the use of restriction enzymes (Flavell et al. (1978). Cell 15:25), discrimination on the basis of electrophoretic mobility in gels with denaturing reagent (Myers and Maniatis (1986). Cold Spring Harbor Symp. Quant. Biol. 51:275-284), RNase protection (Myers et al. (1985). Science 230:1242), chemical cleavage (Cotton et al. (1985). Proc. Natl. Acad. Sci. USA 85:4397-4401) (incorporated herein by reference), and the ligase-mediated detection procedure (Landegren et al., 1988).

Many of the contemplated variant DNA molecules include those created by standard DNA mutagenesis techniques, such as M13 primer mutagenesis. Details of these techniques are provided in Sambrook et al. (1989) In Molecular Cloning: A Laboratory Manual, Cold Spring Harbor, N.Y. (incorporated herein by reference). By the use of such techniques, variants may be created which differ in minor ways from those disclosed. DNA molecules and nucleotide sequences which are derivatives of those specifically disclosed herein and which differ from those disclosed by the deletion, addition or substitution of nucleotides while still encoding a protein which possesses the functional characteristic of the BSMR protein are contemplated by the disclosure. Also included are one small DNA molecules which are derived from the disclosed DNA molecules. Such small DNA molecules include oligonucleotides suitable for use as hybridization probes or polymerase chain reaction (PCR) primers. As such, these small DNA molecules will comprise at least a segment of a lytic enzyme genetically coded for by a bacteriophage specific for *Enterococcus* bacteria and, for the purposes of PCR, will comprise at least a 10-15 nucleotide sequence and, more preferably, a 15-30 nucleotide sequence of the gene. DNA molecules and nucleotide sequences which are derived from the disclosed DNA molecules as described above may also be defined as DNA sequences which hybridize under stringent conditions to the DNA sequences disclosed, or fragments thereof.

Oligonucleotides specific to normal or mutant sequences are chemically synthesized using commercially available machines, labeled radioactively with isotopes (such as $^{32}$P) or non-radioactively (with tags such as biotin (Ward and Langer et al. Proc. Natl. Acad. Sci. USA 78:6633-6657 1981) (incorporated herein by reference), and hybridized to individual DNA samples immobilized on membranes or other solid supports by dot-blot or transfer from gels after electrophoresis. The presence or absence of these specific sequences are visualized by methods such as autoradiography or fluorometric or colorimetric reactions (Gebeyehu et al. Nucleic Acids Res. 15:4513-4534 1987) (incorporated herein by reference).

Sequence differences between normal and mutant forms of the gene may also be revealed by the direct DNA sequencing method of Church and Gilbert (1988) (incorporated herein by reference). Cloned DNA segments may be used as probes to detect specific DNA segments. The sensitivity of this method is greatly enhanced when combined with PCR (Stoflet et al. Science 239:491-494, 1988) (incorporated herein by reference). In this approach, a sequencing primer which lies within the amplified sequence is used with double-stranded PCR product or single-stranded template generated by a modified PCR. The sequence determination is performed by conventional procedures with radiolabeled nucleotides or by automatic sequencing procedures with fluorescent tags. Such sequences are useful for production of lytic enzymes according to examples of the disclosure.

Hybridization conditions corresponding to particular degrees of stringency vary depending upon the nature of the hybridization method of choice and the composition and length of the hybridizing DNA used. Generally, the temperature of hybridization and the ionic strength (especially the sodium ion concentration) of the hybridization buffer will determine the stringency of hybridization. Calculations regarding hybridization conditions required for attaining particular degrees of stringency are discussed by Sambrook et al. (1989), In Molecular Cloning: A Laboratory Manual, Cold Spring Harbor, N.Y., chapters 9 and 11, (herein incorporated by reference).

An example of such calculation is as follows. A hybridization experiment may be performed by hybridization of a DNA molecule (for example, a natural variation of the lytic enzyme genetically coded for by a bacteriophage specific for *Enterococcus* bacteria) to a target DNA molecule. A target DNA may be, for example, the corresponding cDNA which has been electrophoresed in an agarose gel and transferred to a nitrocellulose membrane by Southern blotting (Southern (1975). J. Mol. Biol. 98:503), a technique well known in the art and described in Sambrook et al. (1989) In Molecular Cloning: A Laboratory Manual, Cold Spring Harbor, N.Y. (incorporated herein by reference). Hybridization with a target probe labeled with isotopic P (32) labeled-dCTP is carried out in a solution of high ionic strength such as 6 times SSC at a temperature that is 20-25 degrees Celsius below the melting temperature, Tm, (described infra). For such Southern hybridization experiments where the target DNA molecule on the Southern blot contains 10 ng of DNA or more, hybridization is carried out for 6-8 hours using 1-2 ng/ml radiolabeled probe (of specific activity equal to $10^9$ CPM/mug or greater). Following hybridization, the nitrocellulose filter is washed to remove background hybridization. The washing conditions are as stringent as possible to remove background hybridization while retaining a specific hybridization signal. The term "Tm" represents the temperature above which, under the prevailing ionic conditions, the radiolabeled probe molecule will not hybridize to its target DNA molecule.

The Tm of such a hybrid molecule may be estimated from the following equation: Tm=81.5 degrees C.−16.6 log 10 of sodium ion concentration)+0.41(% G+C)−0.63(% formamide)−(600/l) where l=the length of the hybrid in base pairs. This equation is valid for concentrations of sodium ion in the range of 0.01M to 0.4M, and it is less accurate for calculations of Tm in solutions of higher sodium ion concentration (Bolton and McCarthy (1962). Proc. Natl. Acad. Sci. USA 48:1390) (incorporated herein by reference). The equation also is valid for DNA having G+C contents within 30% to 75%, and also applies to hybrids greater than 100 nucleotides in length. The behavior of oligonucleotide probes is described in detail in Ch. 11 of Sambrook et al. (1989), In Molecular Cloning: A Laboratory Manual, Cold Spring Harbor, N.Y. (incorporated herein by reference).

Thus, by way of example, of a 150 base pair DNA probe derived from the first 150 base pairs of the open reading frame of a cDNA having a % GC=45%, a calculation of hybridization conditions required to give particular stringencies may be made as follows:

Assuming that the filter will be washed in 0.3×SSC solution following hybridization, sodium ion=0.045M; % GC=45%; Formamide concentration=0 l=150 base pairs (see equation in Sambrook et al.) and so Tm=74.4 degrees C. The Tm of double-stranded DNA decreases by 1-1.5 degrees C. with every 1% decrease in homology (Bonner et al. (1973). J. Mol. Biol. 81:123). Therefore, for this given example, washing the filter in 0.3 times SSC at 59.4-64.4 degrees C. will produce a stringency of hybridization equivalent to 90%; DNA molecules with more than 10% sequence variation relative to the target BSMR cDNA will not hybridize. Alternatively, washing the hybridized filter in 0.3 times SSC at a temperature of 65.4-68.4 degrees C. will yield a hybridization stringency of 94%; DNA molecules with more than 6% sequence variation relative to the target BSMR cDNA molecule will not hybridize. The above example is given entirely by way of theoretical illustration. One skilled in the art will appreciate that other hybridization techniques may be utilized and that variations in experimental conditions will necessitate alternative calculations for stringency.

In some examples, stringent conditions may be defined as those under which DNA molecules with more than 25% sequence variation (also termed "mismatch") will not hybridize. In one example, stringent conditions are those under which DNA molecules with more than 15%, 10% or preferably 6% mismatch will not hybridize.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions," as defined herein, can include one of the following conditions: (1) low ionic strength and high temperature for washing, (for example, 0.015 M sodium chloride/0.0015 M sodium citrate/ 0.1% sodium dodecyl sulfate at 50° C.); (2) including a denaturing agent during hybridization, such as formamide (for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.); or (3) 50% formamide, 5×SSC (0.75 M NaCl, 0.075 M sodium citrate), 50 mM sodium phosphate (pH 6.8), 0-1% sodium pyrophosphate, 5× Denhardt's solution, sonicated salmon sperm DNA (50 □g/ml), 0.1% SDS, and 10% dextran sulfate at 42° C., with washes at 42° C. in 0.2×SSC (sodium chloride/sodium citrate) and 50% formamide at 550 C, followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1.times.SSC at about 37-50° C. The skilled artisan will recognize how to adjust the temperature, ionic strength, etc. as necessary to accommodate factors such as probe length and the like.

Vectors/Host Cells Expressing Polynucleotides for Lysins

Embodiments of the disclosure also include vectors that comprise a polynucleotide or polynucleotides encoding one of the lysin polypeptide sequences described herein, or variants or fragments thereof, including just the binding region, or as much as the entire lysin protein or ligation/conjugate of binding region with other protein. Other examples concern host cells that are genetically engineered with vectors of the disclosure and the production of polypeptides of the disclosure by recombinant techniques. Cell-free translation systems can also be employed to produce such proteins using RNAs derived from the DNA constructs of the disclosure.

For recombinant production, host cells can be genetically engineered to incorporate expression systems or portions thereof or polynucleotides of the disclosure. Introduction of a polynucleotide into the host cell can be effected by methods described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as *Streptococci, Staphylococci, Enterococci, E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, 293 and Bowes melanoma cells; and plant cells.

A great variety of expression systems can be used to produce the polypeptides of the disclosure. Such. vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL, (supra).

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the disclosure can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. High performance liquid chromatography is also employed for purification. Well known techniques for refolding protein may be employed to regenerate active conformation when the polypeptide is denatured during isolation and or purification.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Diagnostic Assays

Detection assays advantageously utilize a heterogeneous format wherein a binding reaction between a conjugated binding agent and an analyte occurs followed by a wash step to remove unbound conjugated binding agent. For example, gold sol particles may be prepared with protein that comprises the binding region with the binding protein immobilized on the particle surfaces. As binding occurs between the protein and bacteria, the particles merge and form a colored product. Analogously, the binding protein may be complexed, for example covalently with an enzyme such as beta galactosidase, peroxidase, or horseradish peroxidase. After wash, the remaining bound enzyme can be detected by adding a substrate such as a fluorogenic or chemilumigenic substrate. The binding protein may be complexed with any other reagent that can make a signal such as a rare earth fluor and detected by time resolved fluorescence, a radioactive material and detected by radioactivity measurement, or a regular fluorescent tag, and detected by fluorescence.

The conjugation of the binding region with a detectable tag may be carried out by synthetic chemistry or a biological process. For example, a DNA sequence coding for the binding region or of the entire lysine protein can be linked to genetic information that encodes a detectable marker such as green fluorescent protein (GFP) or an enzyme such as alkaline phosphatase. This could be accomplished by separating the DNA for the binding domain by removing the N-terminal catalytic domain and replacing it in frame with indicator molecules such as green flourescent protein (GFP) and purifying the expressed fusion molecule for the identification of Enterococcus bacteria. Since the binding domain has a similar binding affinity of an immunoglobulin G molecule, the marked binding domain will effectively identify Enterococcus bacteria with little false positive activity. One also could fuse the GFP molecule or an enzyme at the 5' end of the whole lysin enzyme if necessary, by doing so the enzymatic domain will be at least partly inactivated, still allowing the binding domain to function to bind to its substrate in the cell wall.

The isolated binding domain separated from the catalytic domain may be expressed, purified and labeled using a number of fluorescent molecules such as fluorescein isothiocyanate, rhodamine isothiocyanate and others known by skilled artisans. The binding domain may be modified with biotin to allow formation of a biotin-avidin complex after the binding region adheres to the Enterococcus bacteria for identification.

Other catalytic domains may be added to the binding region. As exemplified by Diaz et al. Proc. Natl. Acad. Sci. U.S.A., 87:8125 (1990) for another system, the catalytic domain may be replaced with catalytic domains from other phage lytic enzymes to cleave other bonds in the peptidoglycan cell wall of Enterococcus bacteria. For example, the portion of the 5' end of the gamma lysin gene that codes for the N-terminal catalytic domain (an amidase) may be removed and replaced with the catalytic domain from phage lytic enzymes of other Bacillus phage and even from phage of other gram-positive and gram-negative bacteria. These catalytic domains may be other amidases (which may have higher activity or special features), muramidases, glucaminidases, or endopeptidases, all of which, when genetically fused to the binding domain of the gamma lysin will cleave their respective bonds in the peptidoglycan of the Enterococcus bacteria. In a related example two or three (or more) tandem catalytic domains of different specificities may be fused (i.e., muramidases-glucaminidases-amidase) to a single gamma lysin binding domain to cleave these bonds in the Enterococcus bacteria cell wall peptidoglycan producing a highly active cleaving enzyme. Navarre (Identification of a D alanyl glycine endopeptidase activity. J Biol Chem. 1999 May 28;274: 15847 56.) has shown that triple enzymatic domains may exist in bacteriophage lytic enzymes.

Various conventional linkers can be used, e.g., diisocyanates, diisothiocyanates, carbodiimides, bis-hydroxysuccinimide esters, maleimide-hydroxysuccinimide esters, glutaraldehyde and the like, such as a selective sequential linker such as the anhydride-isothiocyante linker disclosed in U.S. Pat. No. 4,680,338.

Therapeutic Compositions

In some examples, the present disclosure pertains to lytic enzymes as a prophylactic treatment for preventing those who have possibly been exposed to Enterococcus bacteria, or as a therapeutic treatment for those who have already become ill from the infection. The phage associated lytic enzymes described herein are specific for Enterococcus bacteria and preferably effectively and efficiently break down the cell wall of the Enterococcus bacteria.

The lytic enzyme polypeptides described herein may also be employed as a therapeutic agent. The lytic enzyme polypeptides of the present invention can be formulated according to known methods to prepare pharmaceutically useful compositions, whereby the lytic enzyme product hereof is combined in admixture with a pharmaceutically acceptable carrier vehicle. Compositions which may be used for the prophylactic and therapeutic treatment of a Enterococcus bacteria infection also includes the shuffled and/or chimeric enzyme and a means of application (such as a carrier system or an oral delivery mode) to the mucosal lining of the oral and nasal cavity, such that the enzyme is put in the carrier system or oral delivery mode to reach the mucosa lining.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

Prior to, or at the time the modified lytic enzyme is put in the carrier system or oral delivery mode, the enzyme may be in a stabilizing buffer environment for maintaining a suitable pH range, such as between about 5.0 and about 8.0, including a pH of about 5.0, 6.0, 7.0, 8.0 or any pH interval of 0.05 therebetween, or any interval that is a multiple of 0.05 therebetween, including pH values of 5.2, 6.5, 7.4, 7.5 and 8.5.

Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

Any of the carriers for the lytic enzyme may be manufactured by conventional means. However, if alcohol is used in the carrier, the enzyme should be in a micelle, liposome, or a "reverse" liposome, to prevent denaturing of the enzyme. Similarly, when the lytic enzyme is being placed in the carrier, and the carrier is, or has been heated, such placement should be made after the carrier has cooled somewhat, to avoid heat denaturation of the enzyme. The carrier preferably is sterile. One or more lytic enzymes may be added to these substances in a liquid form or in a lyophilized state, whereupon it will be solubilized when it meets a liquid body.

Stabilizing Buffers

A stabilizing buffer should allow for the optimum activity of the lysin enzyme. The buffer may contain a reducing reagent, such as dithiothreitol. The stabilizing buffer may also be or include a metal chelating reagent, such as ethylenediaminetetracetic acid disodium salt, or it may also contain a phosphate or citrate phosphate buffer, or any other buffer. The DNA coding of these phages and other phages may be altered to allow a recombinant enzyme to attack one cell wall at more than two locations, to allow the recombinant enzyme to cleave the cell wall of more than one species of bacteria, to allow the recombinant enzyme to attack other bacteria, or any combinations thereof. The type and number of alterations to a recombinant bacteriophage produced enzyme are incalculable. Any number of chimeric and shuffled lytic enzymes, alone or along with holin proteins, may be assembled to treat the exposure to *Enterococcus* bacteria.

Mucoadhesives

In some examples, a therapeutic composition comprises a mucoadhesive and a lytic enzyme, or chimeric and/or shuffled lytic enzymes, or their peptide fragments when the composition is directed to the mucosal lining to kill colonizing disease bacteria. The mucosal lining, as disclosed and described herein, includes, for example, the upper and lower respiratory tract, eye, buccal cavity, nose, rectum, vagina, periodontal pocket, intestines and colon. Due to natural eliminating or cleansing mechanisms of mucosal tissues, conventional dosage forms are not retained at the application site for any significant length of time.

For these and other reasons it is advantageous to have materials which exhibit adhesion to mucosal tissues, to be administered with one or more phage enzymes and other complementary agents over a period of time. Materials having controlled release capability are particularly desirable, and the use of sustained release mucoadhesives has received a significant degree of attention.

J. R. Robinson (U.S. Pat. No. 4,615,697, incorporated herein by reference) provides a review of the various controlled release polymeric compositions used in mucosal drug delivery. The patent describes a controlled release treatment composition which includes a bioadhesive and an effective amount of a treating agent. The bioadhesive is a water swellable, but water insoluble fibrous, crosslinked, carboxy functional polymer containing (a) a plurality of repeating units of which at least about 80 percent contain at least one carboxyl functionality, and (b) about 0.05 to about 1.5 percent crosslinking agent substantially free from polyalkenyl polyether. While the polymers of Robinson are water swellable but insoluble, they are crosslinked, not thermoplastic, and are not as easy to formulate with active agents, and into the various dosage forms, as the copolymer systems of the present application. Micelles and multi lamellar micelles may also be used to control the release of enzyme.

Other approaches involving mucoadhesives which are the combination of hydrophilic and hydrophobic materials, are known. Orahesive® from E.R. Squibb & Co is an adhesive which is a combination of pectin, gelatin, and sodium carboxymethyl cellulose in a tacky hydrocarbon polymer, for adhering to the oral mucosa. However, such physical mixtures of hydrophilic and hydrophobic components eventually fall apart. In contrast, the hydrophilic and hydrophobic domains in the present disclosure produce an insoluble copolymer.

U.S. Pat. No. 4,948,580, also incorporated by reference, describes a bioadhesive oral drug delivery system. The composition includes a freeze dried polymer mixture formed of the copolymer poly(methyl vinyl ether/maleic anhydride) and gelatin, dispersed in an ointment base, such as mineral oil containing dispersed polyethylene. U.S. Pat. No. 5,413,792 (incorporated herein by reference) discloses paste like preparations comprising (A) a paste like base comprising a polyorganosiloxane and a water soluble polymeric material which are may be present in a ratio by weight from 3:6 to 6:3, and (B) an active ingredient. U.S. Pat. No. 5,554,380 claims a solid or semisolid bioadherent orally ingestible drug delivery system containing a water in oil system having at least two phases. One phase comprises from about 25% to about 75% by volume of an internal hydrophilic phase and the other phase comprises from about 23% to about 75% by volume of an external hydrophobic phase, wherein the external hydrophobic phase is comprised of three components: (a) an emulsifier, (b) a glyceride ester, and (c) a wax material.

U.S. Pat. No. 5,942,243 describes some representative release materials useful for administering antibacterial agents, which disclosure is incorporated by reference.

A therapeutic composition may contain polymeric mucoadhesives consisting essentially of a graft copolymer comprising a hydrophilic main chain and hydrophobic graft chains for controlled release of biologically active agents. The graft copolymer is a reaction product of (1) a polystyrene macromonomer having an ethylenically unsaturated functional group, and (2) at least one hydrophilic acidic monomer having an ethylenically unsaturated functional group. The graft chains consist essentially of polystyrene, and the main polymer chain of hydrophilic monomeric moieties, some of which have acidic functionality. The weight percent of the polystyrene macromonomer in the graft copolymer is between about 1 and about 20% and the weight percent of the total hydrophilic monomer in the graft copolymer is between 80 and 99%, and wherein at least 10% of said total hydrophilic monomer is acidic, said graft copolymer when fully hydrated having an equilibrium water content of at least 90%.

Compositions containing the copolymers gradually hydrate by sorption of tissue fluids at the application site to yield a very soft jelly like mass exhibiting adhesion to the mucosal surface. During the period of time the composition is adhering to the mucosal surface, it provides sustained release of the pharmacologically active agent, which is absorbed by the mucosal tissue.

Mucoadhesivity of the compositions of these embodiments are, to a large extent, produced by the hydrophilic acidic monomers of the chain in the polystyrene graft copolymer. The acidic monomers include, but are not limited to, acrylic and methacrylic acids, 2 acrylamido 2 methyl propane sulfonic acid, 2 sulfoethyl methacrylate, and vinyl phosphonic acid. Other copolymerizable monomers include, but are not limited to N,N dimethylacrylamide, glyceryl methacrylate, polyethylene glycol monomethacrylate, etc.

The compositions of the disclosure may optionally contain other polymeric materials, such as poly(acrylic acid), poly, (vinyl pyrrolidone), and sodium carboxymethyl cellulose plasticizers, and other pharmaceutically acceptable excipients in amounts that do not cause a deleterious effect upon mucoadhesivity of the composition. The dosage forms of the compositions of this disclosure can be prepared by conventional methods.

Pharmaceuticals

The present disclosure also provides compositions comprising one or more pharmaceutical agents and one or more lysins. Further provided are methods of treatment combining administration of one or more pharmaceutical agents and one or more lysins administered separately or in combination.

Pharmaceuticals that may be used include antimicrobial agents, anti-inflammatory agents, antiviral agents, local anesthetic agents, corticosteroids, destructive therapy agents, antifungals, and antiandrogens. Active pharmaceuticals that may be used in topical formulations include antimicrobial agents, especially those having anti-inflammatory properties such as dapsone, erythromycin, minocycline, tetracycline, clindamycin, and other antimicrobials. Weight percentages for the antimicrobials are from about 0.5% to to about 10%.

Local anesthetics include tetracaine, tetracaine hydrochloride, lidocaine, lidocaine hydrochloride, dyclonine, dyclonine hydrochloride, dimethisoquin hydrochloride, dibucaine, dibucaine hydrochloride, butambenpicrate, and pramoxine hydrochloride. An exemplary concentration for local anesthetics is about 0.025% to about 5% by weight of the total composition. Anesthetics such as benzocaine may also be used at a preferred concentration of about 2% to about 25% by weight.

Corticosteroids that may be used include betamethasone dipropionate, fluocinolone actinide, betamethasone valerate, triamcinolone actinide, clobetasol propionate, desoximetasone, diflorasone diacetate, amcinonide, flurandrenolide, hydrocortisone valerate, hydrocortisone butyrate, and desonide are recommended at concentrations of about 0.01% to 1.0% by weight. The concentrations for corticosteroids such as hydrocortisone or methylprednisolone acetate may be from about 0.2% to about 5.0% by weight.

Destructive therapy agents such as salicylic acid or lactic acid may also be used. A concentration of about 2% to about 40% by weight may be used. Cantharidin is may be utilized, for example, in a concentration of about 5% to about 30% by weight. Typical antifungals that may be used in topical compositions and examples of suitable weight concentrations include: oxiconazole nitrate (0.1% to 5.0%), ciclopirox olamine (0.1% to 5.0%), ketoconazole (0.1% to 5.0%), miconazole nitrate (0.1% to 5.0%), and butoconazole nitrate (0.1% to 5.0%). Other topical agents may be included to address a variety of topical co-infections that may occur as will be appreciated by skilled artisans.

Typically, treatments using a combination of drugs include antibiotics in combination with local anesthetics such as polymycin B sulfate and neomycin sulfate in combination with tetracaine for topical antibiotic gels to provide prophylaxis against infection and relief of pain. Another example is the use of minoxidil in combination with a corticosteroid such as betamethasone diproprionate for the treatment of alopecia ereata. The combination of an anti-inflammatory such as cortisone with an antifungal such as ketoconazole for the treatment of tinea infections is also an example.

The composition may comprise dapsone and ethoxydiglycol, which allows for an optimized ratio of micro particulate drug to dissolved drug. This ratio determines the amount of drug delivered, compared to the amount of drug retained in or above the stratum corneum to function in the supracorneum domain. The system of dapsone and ethoxydiglycol may include purified water combined with "CARBOPOL®" gelling polymer, methylparaben, propylparaben, titanium dioxide, BHA, and a caustic material to neutralize the "CARBOPOL®"

In order to accelerate treatment of the infection, the therapeutic agent may further include at least one complementary agent that can also potentiate the bactericidal activity of the lytic enzyme. The complementary agent can be erythromycin, clarithromycin, azithromycin, roxithromycin, other members of the macrolide family, penicillins, cephalosporins, and any combinations thereof in amounts that are effective to synergistically enhance the therapeutic effect of the lytic enzyme. Virtually any other antibiotic may be used with the modified lytic enzyme. Similarly, other lytic enzymes may be included in the carrier to treat other bacterial infections. Holin proteins may be included in the therapeutic treatment.

In some embodiments, a mild surfactant in an amount effective to potentiate the therapeutic effect of the modified lytic enzyme may be used in or in combination with a therapeutic composition. Suitable mild surfactants include, inter alia, esters of polyoxyethylene sorbitan and fatty acids (Tween series), octylphenoxy polyethoxy ethanol (Triton X series), n Octyl beta.D glucopyranoside, n Octyl betaD thioglucopyranoside, n Decal beta D glucopyranoside, n Dodecyl betaD glucopyranoside, and biologically occurring surfactants, e.g., fatty acids, glycerides, monoglycerides, deoxycholate and esters of deoxycholate.

Administration of Compositions Comprising Lysins

Therapeutic compositions comprising one or more lytic enzymes, such as PlyV12, or variants or fragments thereof, can be administered to a subject by any suitable means. Means of application of the lytic enzyme(s) (modified or unmodified) include, but are not limited to direct, indirect, carrier and special means or any combination of means. Direct application of the lytic enzyme may be by nasal sprays, nasal drops, nasal ointments, nasal washes, nasal injections, nasal packings, bronchial sprays and inhalers, or indirectly through use of throat lozenges, mouthwashes or gargles, or through the use of ointments applied to the nasal nares, or any combination of these and similar methods of application. The forms in which the lytic enzyme may be administered include but are not limited to lozenges, troches, candies, injectants, chewing gums, tablets, powders, sprays, liquids, ointments, and aerosols. It is most probable that exposure to the *Enterococcus* bacteria will be through the nose. It is best to be treated for exposure to the bacteria as soon as possible.

When the lytic enzyme(s) is introduced directly by use of nasal sprays, nasal drops, nasal ointments, nasal washes, nasal injections, nasal packing, bronchial sprays, oral sprays, and inhalers, the enzyme may be in a liquid or gel environment, with the liquid acting as the carrier. A dry anhydrous version of the modified enzyme may be administered by the inhaler and bronchial spray, although a liquid form of delivery may also be used.

The lozenge, tablet, or gum into which the enzyme is added may contain sugar, corn syrup, a variety of dyes, non sugar sweeteners, flavorings, any binders, or combinations thereof.

Similarly, any gum based products may contain acacia, camauba wax, citric acid, corn starch, food colorings, flavorings, non sugar sweeteners, gelatin, glucose, glycerin, gum base, shellac, sodium saccharin, sugar, water, white wax, cellulose, other binders, and combinations thereof.

Lozenges may further contain sucrose, corn starch, acacia, gum tragacanth, anethole, linseed, oleoresin, mineral oil, and cellulose, other binders, and combinations thereof. In another embodiment of the disclosure, sugar substitutes are used in place of dextrose, sucrose, or other sugars.

As noted above, the enzyme may also be placed in a nasal spray, wherein the spray is the carrier. The nasal spray can be a long acting or timed release spray, and can be manufactured by means well known in the art. An inhalant may also be used, so that the enzyme may reach further down into the bronchial tract, including into the lungs.

Any of the carriers for the lytic enzyme may be manufactured by conventional means. However, it is preferred that any mouthwash or similar type products not contain alcohol to prevent denaturing of the enzyme, although enzymes in liposomes and in other protective modes and forms may be used in alcohol. Similarly, when the enzyme(s) is (are) being placed in a cough drop, gum, candy or lozenge during the manufacturing process, such placement should be made prior to the hardening of the lozenge or candy but after the cough drop or candy has cooled somewhat, to avoid heat denaturation of the enzyme. The enzyme can also be sprayed over the surface of the cough drop gum, candy, or lozenge, in high enough dosages to be effective.

The enzyme may be added to these substances in a liquid form or in a lyophilized state, whereupon it will be solubilized when it meets body fluids such as saliva. The enzyme may also be in a micelle or liposome.

Dosage of Lysins

The effective dosage rates or amounts of the enzyme(s) to treat the infection will depend in part on whether the enzyme (s) will be used therapeutically or prophylactically, the duration of exposure of the recipient to the infectious bacteria, the size and weight of the individual, etc. The duration for use of the composition containing the enzyme also depends on whether the use is for prophylactic purposes, wherein the use may be hourly, daily or weekly, for a short time period, or whether the use will be for therapeutic purposes wherein a more intensive regimen of the use of the composition may be needed, such that usage may last for hours, days or weeks, and/or on a daily basis, or at timed intervals during the day. Any dosage form employed should provide for a minimum number of units for a minimum amount of time. The concentration of the active units of enzyme that may provide for an effective amount or dosage of enzyme may be in the range of about 10 units/ml to about 500,000 units/ml of fluid in the wet or damp environment of the nasal and oral passages, and topically as well and possibly in the range of about 10, 20, 30, 40, 50, 60, 70, 80, 90, or 100 units/ml to about 50,000 units/ml. Representative values thus include about 200 units/ml, 300 units/ml, 500 units/ml, 1,000 units/ml, 2,500 units/ml, 5,000 units/ml, 10,000 units/ml, 20,000 units/ml, 30,000 units/ml, and 40,000 units/ml. More specifically, time exposure to the active enzyme units may influence the desired concentration of active enzyme units per ml. It should be noted that carriers that are classified as "long" or "slow" release carriers (such as, for example, certain nasal sprays or lozenges) could possess or provide a lower concentration of active (enzyme) units per ml, but over a longer period of time, whereas a "short" or "fast" release carrier (such as, for example, a gargle) could possess or provide a high concentration of active (enzyme) units per ml, but over a shorter period of time. The amount of active units per ml and the duration of time of exposure depends on the nature of infection, whether treatment is to be prophylactic or therapeutic, and other variables. Thus, the number of dosages will be dependent upon the circumstances and can range from 1-4 times per day or more, with durations from one day to multiple weeks. Infections can occur in the skin and thus such compositions may be formulated for topical application as well, using well known vehicles such as those described in U.S. Pat. Nos. 6,056,954 and 6,056,955.

Methods of Treatment

There are a number of advantages to using lytic enzymes to treat bacterial infections, particularly *Enterococcus* bacteria. The modular design of lysins, with their distinct catalytic and binding domains, makes them ideal for domain swapping experiments in which bacterial specificities and catalytic activities can be improved or adapted for use against alternate pathogens. Since the catalytic and binding targets of lysins (peptidoglycan and associated carbohydrates, respectively) are largely essential for viability, lysin resistance will be rare.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

The formulations to be used for in vivo administration are preferably sterile. This is readily accomplished by filtration through sterile filtration membranes, prior to or following lyophilization and reconstitution. Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems. When treating an bacterial exposure or infection, the lytic enzyme may be administered in any suitable fashion, including parenterally or through the oral or nasal cavity.

Dosages and desired drug concentrations of pharmaceutical compositions of the present invention may vary depending on the particular use envisioned. The determination of the appropriate dosage or route of administration is well within the skill of an ordinary physician. Animal-experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a lytic enzyme is employed, normal dosage amounts may vary from about 10 ng/kg to up to 100 mg/kg of mammal body weight or more per day, or about 1 µg/kg/day to 10 mg/kg/day, depending upon the route of administration. Guidance as to particular dosages and methods of delivery is also provided below, as well as in the literature. It is anticipated that different formulations will be effective for different treatment compounds and different disorders, that administration targeting one organ or tissue, for example, may necessitate delivery in a manner different from that to another organ or tissue.

Where sustained-release administration of a lytic enzyme is desired in a formulation with release characteristics suitable for the treatment of any disease or disorder requiring administration of the lytic enzyme, microencapsulation of the lytic enzyme is contemplated. Microencapsulation of recombinant proteins for sustained release has been successfully performed with human growth hormone (rhGH), interferon-(rhIFN-), interleukin-2, and MN rgp120. Johnson et al., Nat. Med., 2:795-799 (1996); Yasuda, Biomed. Ther., 27:1221-1223 (1993); Hora et al., Bio/Technology. 8:755-758 (1990); Cleland, "Design and Production of Single Immunization Vaccines Using Polylactide Polyglycolide Microsphere Systems." in Vaccine Design: The Subunit and Adjuvant Approach, Powell and Newman, eds, (Plenum Press: New York, 1995), pp. 439462; WO 97/03692, WO 96/40072, WO 96/07399; and U.S. Pat. No. 5,654,010.

The sustained-release formulations of these proteins can use poly-lactic-coglycolic acid (PLGA) polymer due to its biocompatibility and wide range of biodegradable properties. The degradation products of. PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), Biodegradable Polymers as Drul: Delivery Systems (Marcel Dekker: New York, 1990), pp. 1-41.

Cutaneous Infection

Compositions for treating topical infections comprise an effective amount of at least one lytic enzyme produced according to this disclosure and a carrier for delivering at least one lytic enzyme to the infected skin. The mode of application for the lytic enzyme includes a number of different types and combinations of carriers which include, but are not limited to an aqueous liquid, an alcohol base liquid, a water soluble gel, a lotion, an ointment, a nonaqueous liquid base, a mineral oil base, a blend of mineral oil and petrolatum, lanolin, liposomes, protein carriers such as serum albumin or gelatin, powdered cellulose carmel, and combinations thereof. A mode of delivery of the carrier containing the therapeutic agent includes, but is not limited to a smear, spray, a time-release patch, a liquid absorbed wipe, and combinations thereof. The lytic enzyme may be applied to a bandage either directly or in one of the other carriers. The bandages may be sold damp or dry, wherein the enzyme is in a lyophilized form on the bandage. This method of application is most effective for the treatment of infected skin.

The carriers of topical compositions may comprise semi-solid and gel-like vehicles that include a polymer thickener, water, preservatives, active surfactants or emulsifiers, anti-oxidants, sun screens, and a solvent or mixed solvent system. U.S. Pat. No. 5,863,560 (Osborne) discusses a number of different carrier combinations that can aid in the exposure of the skin to a medicament.

Polymer thickeners that may be used include those known to one skilled in the art, such as hydrophilic and hydroalcoholic gelling agents frequently used in the cosmetic and pharmaceutical industries. The hydrophilic or hydroalcoholic gelling agent can comprise, for example, "CARBOPOL®" (B.F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), or "STABILEZE®" (ISP Technologies, Wayne, N.J.). The gelling agent may comprise between about 0.2% to about 4% by weight of the composition. More particularly, an examples of the compositional weight percent range for "CARBOPOL®" may be between about 0.5% to about 2%, while the weight percent range for "NATROSOL®" and "KLUCEL®" may be between about 0.5% to about 4%. A compositional weight percent range for both "HYPAN®" and "STABILEZE®" may be between about 0.5% to about 4%.

"CARBOPOL®" is one of numerous cross-linked acrylic acid polymers that are given the general adopted name carbomer. These polymers dissolve in water and form a clear or slightly hazy gel upon neutralization with a caustic material such as sodium hydroxide, potassium hydroxide, triethanolamine, or other amine bases. "KLUCEL®" is a cellulose polymer that is dispersed in water and forms a uniform gel upon complete hydration. Other gelling polymers include hydroxyethylcellulose, cellulose gum, MVE/MA decadiene crosspolymer, PVM/MA copolymer, or a combination thereof.

Preservatives may also be used in this invention and may comprise, for example, about 0.05% to 0.5% by weight of the total composition. The use of preservatives assures that if the product is microbially contaminated, the formulation will prevent or diminish microorganism growth. Some preservatives useful in this invention include methylparaben, propylparaben, butylparaben, chloroxylenol, sodium benzoate, DMDM Hydantoin, 3-Iodo-2-Propylbutyl carbamate, potassium sorbate, chlorhexidine digluconate, or a combination thereof.

Titanium dioxide may be used as a sunscreen to serve as prophylaxis against photosensitization. Alternative sun screens include methyl cinnamate. Moreover, BHA may be used as an antioxidant, as well as to protect ethoxydiglycol and/or dapsone from discoloration due to oxidation. An alternate antioxidant is BHT.

In one embodiment, the invention comprises a dermatological composition having about 0.5% to 10% carbomer and about 0.5% to 10% of a pharmaceutical that exists in both a dissolved state and a micro particulate state. The dissolved pharmaceutical has the capacity to cross the stratum corneum, whereas the micro particulate pharmaceutical does not. Addition of an amine base, potassium, hydroxide solution, or sodium hydroxide solution completes the formation of the gel. More particularly, the pharmaceutical may include dapsone, an antimicrobial agent having anti-inflammatory properties. One exemplary ratio of micro particulate to dissolved dapsone is five or less.

In another embodiment, the invention comprises about 1% carbomer, about 80-90% water, about 10% ethoxydiglycol, about 0.2% methylparaben, about 0.3% to 3.0% dapsone including. both micro particulate dapsone and dissolved dapsone, and about 2% caustic material. More particularly, the carbomer may include "CARBOPOL® 980" and the caustic material may include sodium hydroxide solution.

In one embodiment, if there is a bacterial infection of the upper respiratory tract, the infection can be prophylactically or therapeutically treated with a composition comprising an effective amount of at least one lytic enzyme produced by a bacteria being infected with a bacteriophage specific for that bacteria, and a carrier for delivering the lytic enzyme to a mouth, throat, or nasal passage. The lytic enzyme may be a lytic enzyme, a chimeric lytic enzyme, and/or shuffled lytic enzyme which may be used in conjunction with a holin protein or a combination thereof. The lytic enzyme may be in an environment having a pH which allows for activity of the lytic enzyme. For example, the pH range for the PlyV12 enzyme is about 5-8. If an individual has been exposed to someone with the upper respiratory disorder, the lytic enzyme will reside in the mucosal lining and prevent any colonization of the infecting bacteria.

Parenteral Administration

In some embodiments, an infection may be treated parenterally. The enzymes which can be used are, as above, lytic enzymes, chimeric lytic, enzymes, shuffled lytic enzymes, and combinations thereof. The enzymes can be administered intramuscularly, intravenously, subcutaneously, subdermally, or combinations thereof. In one embodiment, infections may be treated by injecting into the patient a therapeutic agent comprising the appropriate shuffled and/or chimeric lytic enzyme(s) and a carrier for the enzyme. The carrier may be comprised of distilled water, a saline solution, albumin, a serum, or any combinations thereof. More specifically, solutions for infusion or injection may be prepared in a conventional manner, e.g. with the addition of preservatives such as p-hydroxybenzoates or stabilizers such as alkali metal salts of ethylene diamine tetraacetic acid, which may then be transferred into fusion vessels, injection vials or ampules. Alternatively, the compound for injection may be lyophilized either with or without the other ingredients and be solubilized in a buffered solution or distilled water, as appropriate, at the time of use. Non aqueous vehicles such as fixed oils, liposomes, and ethyl oleate are also useful herein. Other phage associated lytic enzymes, along with a holin protein, may be included in the composition.

In cases where intramuscular injection is the chosen mode of administration, an isotonic formulation may be used. Generally, additives for isotonicity can include sodium chloride, dextrose, mannitol, sorbitol and lactose. In some cases, isotonic solutions such as phosphate buffered saline are used. Stabilizers include gelatin and albumin. In some embodiments, a vasoconstriction agent is added to the formulation. The pharmaceutical preparations are provided sterile and pyrogen free. Generally, as noted above, intravenous injection may be most appropriate.

The carrier suitably contains minor amounts of additives such as substances that enhance isotonicity and chemical stability. Such materials are non toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter ions such as sodium; non ionic surfactants such as polysorbates, poloxamers, or polyethylene glycol (PEG); and/or neutral salts, e.g., NaCl, KCl, $MgCl_2$, $CaCl_2$, etc.

Glycerin or glycerol (1,2,3 propanetriol) is commercially available for pharmaceutical use. Glycerin or glycerol may be diluted in sterile water for injection, or sodium chloride injection, or other pharmaceutically acceptable aqueous injection fluid, and used in concentrations of 0.1 to 100% (v/v), 1.0 to 50% or about 20%.

DMSO, is an aprotic solvent with a remarkable ability to enhance penetration of many locally applied drugs. DMSO may be diluted in sterile water for injection, or sodium chloride injection, or other pharmaceutically acceptable aqueous injection fluid, and used in concentrations of 0.1 to 100% (v/v). The vehicle may also include Ringer's solution, a buffered solution, and dextrose solution, particularly when an intravenous solution is prepared.

Prior to, or at the time the enzyme is put in the carrier system or oral delivery mode, it may be desirable for the enzymes be in a stabilizing buffer environment, maintaining a pH range between about 5.0 and about 7.5.

The stabilizing buffer should allow for the optimum activity of the enzyme. The buffer may be a reducing reagent, such as dithiothreitol. The stabilizing buffer may also be or include a metal chelating reagent, such as ethylenediaminetetracetic acid disodium salt, or it may also contain a phosphate or citrate phosphate buffer. The buffers found in the carrier can serve to stabilize the environment for the lytic enzymes.

The effective dosage rates or amounts of the enzyme to be administered parenterally, and the duration of treatment will depend in part on the seriousness of the infection, the weight of the patient, the duration of exposure of the recipient to the infectious bacteria, the seriousness of the infection, and a variety of a number of other variables. The composition may be applied anywhere from once to several times a day, and may be applied for a short or long term period. The usage may last for days or weeks. Any dosage form employed should provide for a minimum number of units for a minimum amount of time. The concentration of the active units of enzyme believed to provide for an effective amount or dosage of enzyme may be in the range of about 10, 20, 30, 40, 50, 60, 70, 80, 90, or 100 units/ml up to about 10,000,000 units/ml of composition, in a range of about 1000 units/ml to about 10,000,000 units/ml, and from about 10,000 to 10,000,000 units/ml. The amount of active units per ml and the duration of time of exposure depends on the nature of infection, and the amount of contact the carrier allows the lytic enzyme to have. It is to be remembered that the enzyme works best when in a fluid environment. Hence, effectiveness of the enzyme is in part related to the amount of moisture trapped by the carrier. The concentration of the enzyme for the treatment is dependent upon the bacterial count in the blood and the blood volume.

In order to accelerate treatment of the infection, the therapeutic agent may further include at least one complementary agent which can also potentiate the bactericidal activity of the lytic enzyme. The complementary agent can be any antibiotic effective against *Enterococcus* bacteria. Similarly, other lytic enzymes may be included to treat other bacterial infections.

Additionally, a number of methods can be used to assist in transporting the enzyme across the cell membrane. The enzyme can be transported in a liposome, with the enzyme be "inserted" in the liposomes by known techniques. Similarly, the enzyme may be in a reverse micelle. The enzyme can also be pegylated, attaching the polyethylene glycol to the non-active part of the enzyme. Alternatively, hydrophobic molecules can be used to used to transport the enzyme across the cell membrane. Finally, the glycosylation of the enzyme can be used to target specific internalization receptors on the membrane of the cell.

EXAMPLES

A bacteriophage lysin, PlyV12, with killing activity against *E. faecalis* strain V12 as well as several other gram positive bacteria was isolated from the enterococcal bacteriophage φ1, and characterized in a series of exemplary embodiments described below. More specifically, in the examples described below, the efficacy of PlyV12 in killing various Gram positive bacteria, including strains of *Entero-* cocci bacteria was studied both in vitro and in vivo. The PlyV12 lysin was cloned, purified and biochemically characterized, with its spectrum of activity examined against a range of bacterial species. The catalytic activity and binding affinity of the lysin were also investigated.

For the examples described below, unless otherwise indicated, the following bacterial strains, plasmids and media were used.

TABLE 3

Bacterial strains used:

| Bacterial strain | Source |
|---|---|
| *Escherichia coli* | |
| *Escherichia coli* XL1-Blue | 1 |
| *Escherichia coli* DH5-α | 2 |
| *Escherichia coli* RosettaBlue ™ (DE3) pLysS | 3 |
| *Escherichia coli* SCS110 | 1 |
| *Escherichia coli* EPI300 | 4 |
| *Escherichia coli* BL21 (DE3) | 2 |
| *Escherichia coli* XL1-Red | 1 |
| *Escherichia coli* TOP10 | 2 |
| *Enterococci* | |
| *Enterococcus faecalis* V12 | 5 |
| *Enterococcus faecalis* V12S | This work |
| *Enterococcus faecalis* V583 | 6 |
| *Enterococcus faecalis* A220 | 5 |
| *Enterococcus faecalis* A936 | 5 |
| *Enterococcus faecalis* B722 | 5 |
| *Enterococcus faecalis* D76 | 5 |
| *Enterococcus faecalis* JH2-2 | 7 |
| *Enterococcus faecalis* EF-24 | 7 |
| *Enterococcus faecalis* EF-25 | 7 |
| *Enterococcus faecalis* 8413 | 5 |
| *Enterococcus faecalis* HER1323 | 5 |
| *Enterococcus faecalis* (VRE) EF-1 | 7 |
| *Enterococcus faecalis* (VRE) EF-17 | 7 |
| *Enterococcus faecium* (VRE) EFSK-2 | 7 |
| *Enterococcus faecium* (VRE) EFSK-16 | 7 |
| *Enterococcus faecium* (VRE) EFSK-33 | 7 |
| Lancefield group *streptococci* | |
| Group A *streptococcus* strain D471 | 5 |
| Group A *streptococcus* strain CS24 | 5 |
| Group A *streptococcus* strain CS112 | 5 |
| Group A *streptococcus* strain A486 variant | 5 |
| Group B *streptococcus* strain NC11237 | 5 |
| Group B *streptococcus* strain A349 | 5 |
| Group B *streptococcus* strain A909 | 5 |
| Group C *streptococcus* strain 2GRP66 | 5 |
| Group E *streptococcus* strain K131 | 5 |
| Group F *streptococcus* strain F68C | 5 |
| Group G *streptococcus* strain D166B | 5 |
| Group L *streptococcus* strain D167A | 5 |
| Group N *streptococcus* strain C559 | 5 |
| Other *streptococci* | |
| *Streptococcus pneumoniae* GB2162 | 5 |
| *Streptococcus pneumoniae* PK1850 | 5 |
| *Streptococcus uberis* 45 | 5 |
| *Streptococcus uberis* ATCC27958 | 5 |
| *Streptococcus gordonii* GP251 | 8 |
| *Streptococcus gordonii* FS12 | 5 |
| *Streptococcus gordonii* PK488 | 5 |
| *Streptococcus mutans* ATCC25175 | 5 |
| *Streptococcus mutans* 10449 | 5 |
| *Streptococcus oralis* PK34 | 5 |
| *Streptococcus salivarius* ATCC9222 | 5 |
| *Streptococcus rattus* BHT | 5 |
| *Streptococcus sobrinus* 6715 | 5 |
| *Streptococcus mitis* J22 | 5 |
| *Streptococcus intermedius* PK2821 | 5 |
| *Streptococcus parasanguis* PK2564 | 5 |
| *Streptococcus crista* PK1408 | 5 |
| *Staphylococci* | |

TABLE 3-continued

Bacterial strains used:

| Bacterial strain | Source |
|---|---|
| *Staphylococcus aureus* RN4220 | 5 |
| *Staphylococcus aureus* RN6390 | 5 |
| *Staphylococcus aureus* HER1283 | 5 |
| *Staphylococcus epidermidis* BJ0018 | 5 |
| *Bacillus* | |
| *Bacillus megaterium* WH320 | 9 |

Sources of Bacteria

1, Strategene, La Jolla CA;

2, Invitrogen, Carlsbad CA;

3, Novagen, San Diego CA;

4, Epicentre, Madison WI;

5, Rockefeller University Bacteria Collection, New York NY;

6, American Type Culture Collection, Manassas VA;

7, Alexander Tomasz, Rockefeller University, New York NY;

8, Thomas Broudy, Rockefeller University, New York NY;

9, MoBiTec, Marco Island FL.

VRE, vancomycin resistant *enterococci*.

Competent Bacterial Cells and DNA Transformation

Chemically competent *E. coli* were either purchased from commercial sources, or made competent in the laboratory using a calcium chloride method and transformed according to standard protocols (Sambrook, J., E. F. Fritsch, and T. Maniatis. 1989. Molecular cloning: a laboratory manual, 2nd ed. Cold Spring Harbor Laboratory Press, Cold Spring Harbor). *Streptococcus gordonii* GP251 was made competent and transformed with plasmid DNA following procedures by Pozzi et al (Pozzi, G., R. A. Musmanno, M. Stellini and A. M. Molina. 1987. Transformation of *Streptococcus sanguis* Challis with a plasmid of *Streptococcus pneumoniae*. FEMS Microbiol. Lett. 48:189-194). *B. megaterium* WH320 (MoBiTec, Marco Island Fla.) was made competent and transformed with plasmid DNA according to manufacturer's instructions.

Plasmids

All plasmids were extracted from bacteria using QIAprep spin miniprep and maxi plasmid kits (Qiagen, Valencia Calif.). Unless otherwise indicated, plasmids generated in this work were constructed by polymerase chain reaction (PCR) amplification of a selected open reading frame (ORF) with primers harboring restriction sites on the 5' end. When possible, different restriction sites were used to achieve directional cloning. The digested PCR product and corresponding phosphatase treated (USB, Cleveland Ohio) plasmid vector were then ligated. Resulting plasmid clones were confirmed to be correct by DNA sequencing, restriction digest pattern and/or PCR.

TABLE 4

Plasmids used and constructed in these experiments.

| Plasmid | Features | References |
| --- | --- | --- |
| pBAD24 | Arabinose inducible cloning vector for *E. coli*, containing a ribosome binding site | 1 |
| pBAD24-lysin2 | Inducible expression of PlyV12 with about a hundred basepairs flanking sequence | This work |
| pBAD24-lysin1.5 | Inducible expression of PlyV12 with about a hundred basepairs downstream sequence | This work |
| pBAD24-PlyGcat + PlyV12bind | Inducible expression of fusion protein consisting of catalytic domain of PlyG and binding domain of PlyV12 from plyV12 | This work |
| pBAD24-PlyGcat + PlyV12CObind | Inducible expression of fusion protein consisting of catalytic domain of PlyG and binding domain of PlyV12 from plyV12CO | This work |
| pBAD24-EF0355 | Inducible expression of *E. faecalis* V583 EF0355 | This work |
| pBAD24-EF1293 | Inducible expression of *E. faecalis* V583 EF1293 | This work |
| pBAD24-EF2086 | Inducible expression of *E. faecalis* V583 EF2086 | This work |
| pBAD24-EF2802 | Inducible expression of *E. faecalis* V583 EF2802 | This work |
| pBAD/HisB | Arabinose inducible histidine tag fusion vector | 1 |
| pBAD-6xhis-lysin | Inducible expression of histidine tagged PlyV12 | This work |
| pBAD TOPO | Arabinose inducible TOPO cloning vector | 1 |
| pBluescript KS+ | IPTG inducible cloning vector for *E. coli* | 3 |
| pBluescript-lysin2 | Inducible expression of PlyV12 with about a hundred basepairs flanking sequence | This work |
| pSTOP | *E. coli-streptococcus* shuttle vector | 4 |
| pDG148 | IPTG inducible *E. coli-Bacillus* shuttle vector | 2 |
| pDG148-lysin2* | Inducible expression of PlyV12 with about a hundred basepairs flanking sequence | This work |
| pDG148-6xhis-lysin | Inducible expression of histidine tagged PlyV12 | This work |
| pVK55a | IPTG inducible *E. coli-Bacillus* shuttle vector | 2 |
| pVK55a-lysin2 | Inducible expression of PlyV12 with about a hundred basepairs flanking sequence | This work |
| pUC18-plyV12CO | Codon optimized plyV12 in opposite orientation to the promoter | 5 |
| pGEX-5X-3 | Glutathione S-transferase (GST) fusion vector | 6 |
| pCC1 | Inducible copy number plasmid | 7 |
| pCC1-plyV12CO | Codon optimized plyV12 in pCC1 | This work |
| pMSP3535 | *E. coli-enterococcus* shuttle vector | 8 |
| pWH1520 | *E. coli-B. megaterium* shuttle vector | 9 |

1, Invitrogen, Carlsbad CA;
2, Raymond Schuch, Rockefeller University, New York NY;
3, Stratagene, La Jolla CA;
4, Thomas Broudy, Rockefeller University, New York NY;
5, GenScript Corporation, Piscataway NJ;
6, Matthias Collin, Rockefeller University, New York NY;
7, Epicentre, Madison WI;
8, Gary Dunny, University of Minnesota, Minneapolis MN;
9, MoBiTec, Marco Island FL.
*pDG148-lysin2 was described as pPY1 in Yoong, P., R. Schuch, D. Nelson, and V. A. Fischetti. 2004. Identification of a broadly active phage lytic enzyme with lethal activity against antibiotic-resistant *Enterococcus faecalis* and *Enterococcus faecium*. J. Bacteriol. 186: 4808-4812.

Media

Luria-Bertani (LB) media was used for the growth of *E. coli* strains and *B. megaterium* strain WH320. Todd Hewitt media supplemented with 1% yeast extract (THY) and brain heart infusion (BHI) were used interchangeably for the culturing of *enterococcal, streptococcal* and staphylococcal strains. For solid medium, agar was added to 1.5%, while 0.75% was added to soft agar employed in overlays. BBL™ Enterococcosel™ Agar (Difco, Sparks Md.) was used in selective culturing of *enterococci* from a mixed bacterial population.

Where necessary, antibiotics were added to media for the selection and maintenance of plasmids. Ampicillin at 100 μg/mL was used in the selection of pBluescript, pGEX-5X-3, pWH1520 and pBAD based vectors, chloramphenicol at 12.5 μg/mL was used in the maintenance of pCC1 and 34 μg/mL for *E. coli* RosettaBlue, kanamycin at 15 μg/mL for pDG148, spectinomycin at 100 μg/mL for pVK55a, and erythromycin at 5 μg/mL for pSTOP, and between 100 to 250 μg/mL for pMSP3535. Streptomycin was used at various concentrations, with specific concentrations used listed in the relevant sections. For pBAD based vectors, protein expression was induced upon the addition of arabinose to 0.25%, while expression from pDG148 was induced with 1 mM IPTG. T7 polymerase was also induced with 1 mM IPTG from *E. coli* BL21 (DE3).

Unless otherwise stated, molecular cloning enzymes were purchased from New England Biolabs (Beverly Mass.), and reagents from Sigma-Aldrich (St. Louis, Mo.).

Example 1

Phage Manipulations

Table 5 lists the bacteriophages used in certain exemplary embodiments below, and the sources thereof.

TABLE 5

Bacteriophages used

| Enterococcus faecalis | Source |
|---|---|
| φ1 | 1 |
| φVD13 | 1 |
| φ182 | 1 |
| φVD1884 | 1 |

Sources of Bacteriophages used in this study:
1, Rockefeller University Phage Collection, New York N.Y.

Phage Propagation

The bacteriophages φ1 and φVD13 were propagated on *E. faecalis* strains V12 and 8413 respectively, beginning on a small scale and gradually scaling up production to increase phage titers. To begin, 100 µL of phage was mixed with 100 µL of the corresponding *E. faecalis* overnight culture, with the addition of 5 mL THY broth, followed by stationary overnight incubation at 37° C. The following day, the bacterial lysate was centrifuged and filtered through a 0.22 µm filter. Five milliliters of the phage containing lysate was added to 2 mL of *E. faecalis* overnight culture with 200 mL THY broth, and incubated overnight at 37° C. with aeration. The lysate was centrifuged and 200 mL of the unfiltered phage containing supernatant added to 300 mL of *E. faecalis* grown in THY broth to an optical density at 600 nm ($OD_{600}$) of 0.3. The mixture was incubated at 37° C. with aeration for an additional 3 to 5 hours at which time it was centrifuged to remove unlysed bacteria. The phage suspensions were stored at 4° C. in the presence of 5 mL chloroform.

Phage Titering by Plaque Assays

Plaque assays of *E. faecalis* bacteriophages were performed. One hundred microliters of an overnight *E. faecalis* culture was mixed with 2.5 mL of soft THY agar and overlaid on a THY agar plate. Phage dilutions were dropped on the surface of each plate at 10 or 20 µL. The plates were incubated at 37° C. overnight, with single plaques counted the following day in order to calculate plaque forming units per milliliter (PFU /mL).

Phage Isolation from Environmental Samples

Attempts were made at isolating *E. faecalis* bacteriophages from 2 sewage samples, 2 separate samples from the East River, a landfill dirt suspension, water from a pond in Long Island and water from Cold Spring Harbor. One to two milliliters of each filtered and concentrated samples were added to 100 µL of overnight cultures of at least 4 different *E. faecalis* strains with 10 mL THY broth containing 3 mM CaCl2, followed by stationary overnight incubation at 37° C. The next day, the mixture was centrifuged and filtered. The titering of any amplified phages were carried out on the strain of *E. faecalis* it was propagated on.

Phage Induction

Phage inducting was performed using Mitomycin C. Overnight cultures of *E. faecalis* at 0.5 mL were added to 10 mL THY broth. Mitomycin C was added to a final concentration of 1 µg/mL and incubated at 37° C. overnight. The mixture was centrifuged and filtered the following day. One hundred microliters of the filtrate was added to 100 µL of *E. faecalis* overnight culture, and mixed with 3 mL THY soft agar overlaid on a THY agar plate. The plates were incubated overnight at 37° C. Plaques on the *E. faecalis* lawns were indicative of successful phage induction.

Phage induction was also performed using UV induction. A THY agar overlay consisting of 100 µL *E. faecalis* overnight culture and 2.5 mL THY soft agar was UV irradiated for 20, 40, 60 and 90 seconds. Overlays were generated with several different *E. faecalis* strains. Following irradiation, dilutions of at least 4 strains of *E. faecalis* were dropped onto the surface of each plate in 10 µL drops. After an overnight incubation at 37° C., the plates were observed for plaques within the *E. faecalis* drops.

Phage DNA Extraction

Where necessary, phage suspensions were concentrated with an Amicon 8400 unit (Millipore, Bedford Mass.) through a 10 kDa cutoff membrane. Media containing phage was ultracentrifuged at a speed of 30,000 revolutions per minute (rpm) for 2 hours to pellet the phage particles (Beckman model L5-65 ultracentrifuge). Each pellet resulting from 50 mL of phage containing media was suspended in 500 µL of 20 mM Tris at pH 7.4 containing 50 mM sodium chloride (NaCl). DNAse and RNase were each added to a final concentration of 20 ng/mL for the digestion of any contaminating non-phage DNA. The phage DNA would remain intact as it would be protected by its protein capsid. The nucleic acids digest was carried out at 37° C. for 30 minutes. To digest the phage capsid, 50 µL of 0.5M ethylenediaminetetraacetic acid (EDTA) was added to stop the nucleic acid digest, followed by the addition of protease K to 400 µg/mL and sodium dodecyl sulfate (SDS) to 0.5% and incubated at 60° C. for 1 hour. The phage DNA was then extracted using the phenol-chloroform method and ethanol precipitated (Sambrook, J., E. F. Fritsch, and T. Maniatis. 1989. Molecular cloning: a laboratory manual, 2nd ed. Cold Spring Harbor Laboratory Press, Cold Spring Harbor). The DNA pellet was suspended in 500 µL of 10 mM Tris at pH 8.5.

Example 2A

Identification and Cloning of Phage Lysins

Phage Genomic Library Method; Identification of the Gene for PlyV12 from *E. faecalis* Phase φ1

This method used to clone phage lysins was a variation of that used by Loessner et al (Loessner, M., G. Wendlinger, and S. Scherer. 1995. Heterogeneous endolysins in *Listeria monocytogenes* bacteriophages: a new class of enzymes and evidence for conserved holin genes within the siphoviral lysis cassettes. Mol. Microbiol. 16:1231-1241; and Loessner, M., S. Gaeng, and S. Scherer. 1999. Evidence for a holin-like protein gene fully embedded out of frame in the endolysin gene of *Staphylococcus aureus* bacteriophage 187. J. Bacteriol. 181:4452-4460). It was used successfully to clone the lysin encoding gene from φ1, a bacteriophage isolated from *E. faecalis* strain V12, but not successful in isolating a lysin encoding gene from φVD13. Briefly, phage DNA was either partially digested with Tsp509I, or digested to completion with HindIII. Following agarose gel electrophoresis, the partially digested Tsp509I DNA fragments were excised in the range of 0.5 to 3.5 kilobases (kb) and extracted from the gel using a commercially available spin column. All the bands from the complete HindIII digest were purified directly using a spin column. The Tsp509I and HindIII fragments were ligated into pBAD24 treated with EcoRI and HindIII respectively, followed by treatment with shrimp alkaline phosphatase. pBAD24 is an *E. coli* plasmid expression vector with an arabinose inducible promoter upstream of a multiple cloning site. Both libraries were transformed into chemically competent *E. coli* XL1-Blue, followed by selection on LB agar plates supplemented with ampicillin to 100 g/mL. The transformants were then replica plated onto glass plates containing LB agar supplemented with 100 μg/mL ampicillin and 0.25% arabinose in order to induce expression of gene/s cloned downstream of the arabinose promoter of pBAD24. After an overnight incubation at 37° C., resulting colonies on the glass plates were exposed to chloroform vapors for 10 minutes to permeabilize the cell membrane, and 6 mL of soft LB agar overlay containing 0.5 mL of 100-fold concentrated log phase E. faecalis V12 was applied. After overnight incubation at room temperature, colonies were screened for lytic activity by observing for zones of E. faecalis clearing around any E. coli clones. At least 1,000 colonies were screened from each library. One positive clone was isolated from a Tsp509I φ1 library, and another from a HindIII φ1 library. Both clones were sequenced and found to contain overlapping DNA sequence. Putative ORFs from approximately 4 kb of sequenced DNA from both φ1 clones with lytic activity against E. faecalis were identified using the ORF Finder program within the National Center for Biotechnology Information (NCBI) website (http://www.ncbi.nlm.nih.gov).

The gene encoding PlyV12, the lysin from φ1, was identified as detailed above. The ORF, along with about 100 basepairs (bp) of flanking up and downstream sequence was amplified from the phage DNA and cloned into the pBAD24 vector, the resulting clone named pBAD24-lysin2 (Table 6). The same insert was cloned into pBluescript, pDG148 and pVK55a. A pBAD24 clone containing the plyV12 coding sequence with its 100 bp downstream sequence was generated and named pBAD24-lysin1.5. Creation of a polyhistidine tag fusion of PlyV12 was carried out by cloning plyV12 without its first three nucleotides into the BglII and EcoRI sites of pBAD/HisB. This fusion gene was subcloned into pDG148 as well.

Linker Amplified Shotgun Libraries (LASL)

This technique, named linker amplified shotgun libraries or LASL, was developed by Breitbart et al (Breitbart, M., P. Salamon, B. Andresen, J. M. Mahaffy, A. M. Segall, D. Mead, F. Adam, and F. Rohwer. 2002. Genomic analysis of uncultured marine viral communities. Prot. Natl. Acad. Sci. USA. 99:14250-14255). It is a genetic technique that allows the amplification of DNA from bacteriophages that are viable in nature but not culturable under laboratory conditions, thereby omitting the need to culture those phages in order to harvest their genetic material. Briefly, water from various natural sources were filtered to remove most bacterial and eukaryotic cells, but not phages. The phage containing filtrate is then concentrated and phages purified by cesium chloride gradient. Purified phage DNA was digested or sheared to approximately 2 kb fragments and ligated with double stranded DNA linkers. Phage DNA is amplified by PCR using primers specific to the linker DNA sequences, followed by cloning into an inducible expression vector to generate a phage DNA library. In this work, the pBAD TOPO vector was used, followed by transformation of the cloned DNA library into E. coli TOP10.

Using this method, DNA libraries generated from Lake Havasu in Arizona and a human fecal sample were screened for lytic activity against E. faecalis strain V12 as in the preceding section. Several thousand colonies from each library were screened using the overlay method. Master LB ampicillin agar plates containing several thousand colonies of E. coli TOP10 harboring the Lake Havasu DNA library cloned into PBAD TOPO were generously provided by Matthias Collin and Raymond Schuch of the Fischetti laboratory. The PCR amplified human fecal sample was provided by Dr. Collin.

Four clones from the human sample that appeared to have lytic activity against E. faecalis were sent for DNA sequencing.

Identification and Cloning of Lysogenic Phage Lysins

The E. faecalis strain V583 complete genome sequence is accessible at the NCBI website. Five putative lysogenic phage lysins were identified in the genome of this sequenced E. faecalis strain. This was achieved by searching for ORFs annotated as putative phage holins, followed by manual scanning of flanking ORFs. Lysins and holins are often found adjacent to each other as part of the phage 'lysis cassette'. The identified ORFs encoding for putative phage lysins were EF0355, EF1293, EF1992, EF2086 and EF2802. As the codon usage pattern of these ORFs were estimated to be similar with that of plyV12 with about 20% of each gene being under the threshold of expression in E. coli, initial cloning attempts were made into the E. coli-B. megaterium shuttle vector pWH1520. Subsequently, the ORFs were cloned into pBAD24. The pBAD24 clones of the lysogenic phage lysins were transformed into both E. coli XL1-Blue and RosettaBlue. Two different induction protocols were tried. In both E. coli strains, each culture was grown at 37° C. for 2 hours before the addition of arabinose. Upon addition of arabinose, the cultures were either grown at 37° C. for another 4 hours, or transferred to 30° C. for 4 hours followed by gentle shaking overnight at 4° C. Cell lysis was achieved with the BugBuster reagent (See Example 3 below).

PCR of Enterococcal Phages Using Primers Specific to φ1

In addition to φ1, there are three additional enterococcal phages in the Rockefeller Phage Collection, including φ182, φVD1884 and φVD13. Gradient PCR using DNA from these other enterococcal phages as template with primers specific to φ1 sequences were attempted in hope of identifying lysin encoding genes from those phages that may bare some resemblance to plyV12. Primer annealing temperatures used began as low as 30° C. using plyV12 specific primers and primers that anneal to the sequence flanking plyV12.

Example 2B

Isolation of PlyV12

The plyV12 gene was initially cloned into several Escherichia coli expression systems, however, the enzyme yields were very low in all cases. PlyV12 (as other lytic enzymes) is translated without a leader sequence, thus it remains in the cytoplasm where it cannot exert an effect on its peptidoglycan substrate, therefore making it possible to be expressed in a wide range of systems. Subsequently, the plyV12 gene and approximately 100 bp of flanking sequence was amplified by polymerase chain reaction and cloned into an E. coli-Bacillus shuttle vector pDG148, yielding pPY1. PlyV12 was then expressed in Bacillus megaterium strain WH320 (MoBiTec, Marco Island, Fla.) by induction with isopropyl-β-D-thiogalactopyranoside for 1 hour, at which time the culture was centrifuged. The pelleted bacteria were suspended in 100 mL of a lysis reagent, BugBuster (diluted from a 10× concentration to 1× in phosphate buffered saline {PBS} containing 100 μg/ml lysozyme) (Novagen, San Diego, Calif.). This cell lysate was allowed to remain at 37° C. for 1 hour, followed by centrifugation at 4,000 revolutions per minute to pellet the cell debris. The supernatant containing the crude lysin was diluted 1 in 3 in 50 mM MES at pH 6.7 prior to loading on three 5 mL HiTrap SP HP columns connected in series (Amersham Biosciences, Piscataway, N.J.). The columns were washed with the 50 mM MES buffer until the optical density at a wavelength of 280 nm reached baseline. PlyV12 was eluted with a 20 column volume linear gradient to 1M sodium chloride (NaCl), and a peak at ~330 mM NaCl was found to contain the lytic activity. Furthermore, sodium dodecyl sulfate-polyacrylamide gel electrophoresis (SDS-PAGE) revealed a 34 kDa band corresponding to this peak, which matched the predicted size of PlyV12. Fractions constituting the peak were pooled and concentrated to 25 units/mL (see below) in an Amicon Ultra unit with a 10 kDa cutoff (Millipore, Billerica, Mass.). The final PlyV12 sample was purified >85% based on spot desitometry (Alpha Innotech's Alphalmager™, San Leandro, Calif.) of the SDS-PAGE gel images of crude and purified PlyV12 that were obtained by sodium dodecyl sulfate-polyacrylamide gel electrophoresis.

Example 3

Bacterial Lysis

Chloroform Extraction

This method was used to extract heterologous proteins expressed in *E. coli*. The bacterial culture was pelleted by centrifugation, and the resulting pellet washed with 50 mM potassium phosphate buffer at pH 7.4 or phosphate buffered saline (PBS). This wash step was repeated and the pellet suspended in phosphate buffer at 1/20 the original culture volume. Chloroform was added at 1/5 volume of the bacterial suspension and the mixture was rotated gently at room temperature for 1 hour. The mixture was centrifuged at 4,000 rpm, and the top layer containing the cell lysate was carefully removed.

Lysis Reagent

BugBuster™ is the tradename of a lysis reagent purchased from a commercial source (Novagen, San Diego Calif.) as a 10× concentrated stock. For use, it was diluted to 1× concentration with PBS containing 100 μg/mL lysozyme. A bacterial cell pellet was typically resuspended in 1× BugBuster containing 100 μg/mL lysozyme at 1/20 the original culture volume, followed by incubation at 37° C. for 1 hour. A centrifugation step at 4,000 rpm sediments the cell debris, while the supernatant contains the cell lysate.

Homogenization

Bacterial cultures were centrifuged and suspended in 1/20 volume of an appropriate buffer. The bacterial suspension was passaged through a high pressure homogenizer (EmulsiFlex-C5; Avestin Inc., Ottowa, Canada) above 15,000 pounds per square inch (psi) between 3 to 4 times to effectively lyse the cells. A centrifugation step at 7,000 rpm was required to remove the cell debris.

*Escherichia coli* RosettaBlue™ (DE3) pLysS

*E. coli* RosettaBlue™ (DE3) pLysS expresses T7 lysozyme from its pLysS plasmid. Lysis of this *E. coli* strain can be achieved by freezing a pellet form of it, followed by suspension in an appropriate buffer.

Example 4

Assays for Phage Lysin Activity Against Bacteria

Overlay Method

The overlay method was outlined in the screening of phage genomic DNA libraries for lysins against *E. faecalis* in previous sections. To summarize, this method entailed the spotting of *E. coli* clones on the surface of agar plates, growing these clones overnight, then exposure to chloroform vapor in order to permeabilize the cell membrane, followed by an overlay with the indicator bacterial strain. For the screening of lytic activity against *E. faecalis*, 6 mL of soft LB agar overlay containing 0.5 mL of 100-fold concentrated log phase *E. faecalis* was applied. *E. faecalis* strain V12 was used for screening the φ1 library, while *E. faecalis* strain 8413 was used in screening the φVD13 library. After overnight incubation at room temperature, colonies were screened for lytic activity by observing for zones of *E. faecalis* clearing around *E. coli* clones.

Optical Density Assays

For OD assays with PlyV12, *E. faecalis* V12 was grown in THY or BHI broth with aeration at 37° C. for approximately 3 hours. The culture was pelleted and suspended in PBS to $OD_{600}$ of 2.0. Enterococcal, streptococcal and staphylococcal strains were grown and processed in this manner as well. One hundred microliters of the bacterial suspension was mixed with 100 μL of lysate containing PlyV12 or purified PlyV12 in a 96 well plate. $OD_{600}$ was read on a spectrophotometric plate reader (SpectraMax Plus384; Molecular Devices, Sunnyvale Calif.) every 15 to 30 seconds over a 15 minute to 1 hour time period to monitor any OD changes. Control reactions were set up in parallel containing PBS instead of lysin. Where crude cell lysates were obtained using the lysis reagent BugBuster, a control reaction containing BugBuster instead of PBS was used.

Viability Assays

Viability assays were performed as follows: *E. faecalis* V12 was grown as above; bacterial suspensions and lysin were mixed together in a similar manner as the previous section; and at the end of the incubation period, the reactions were serially diluted in PBS to $10^{-2}$, $10^{-4}$, $10^{-6}$ and $10^{-8}$ with 50 μL of each dilution plated on a quadrant of a BHI agar plate. The resulting viability counts were calculated from the number of colonies that arise following overnight incubation at 37° C.

Example 5

Variations in Lysin Activity Assays

Quantitation of Lysin Activity

The quantitation of lysin activity is based on the Optical Density ("OD") assay method (described in the Optical Density Assay portion of Example 4 above). The *E. faecalis* indicator strain for the PlyV12 enzyme was grown and washed as described, while the lysin sample to be quantified was serially diluted 2-fold with PBS. One hundred microliters of each bacterial suspension was added to an equal volume of each lysin dilution. The starting optical density of each bacterial suspension was typically 2.0. The optical density change of each reaction was monitored for 15 minutes. The lytic activity of lysins is expressed in units per milliliter, in which units represent the reciprocal of the highest dilution of enzyme resulting in a 50% reduction in bacterial $OD_{600}$ in 15 minutes.

Determining the pH Profile of PlyV12 Activity

*E. faecalis* V12 was grown as above, but instead of suspension in PBS, the bacterial cells were resuspended in 100 mM acetate buffer at pH 5.2, 100 mM morpholinepropanesulfonic acid at pH 6.5, or 100 mM Tris at pH 7.5 or pH 8.5 instead. One hundred microliters of each enterococcal suspension was mixed with 100 μL of purified PlyV12 at 25 units/mL. The $OD_{600}$ of each reaction was measured over a 15 minute period at 15 second intervals.

Analyzing Lysin Activities in Increasing Salt Concentrations

A 5M sodium chloride stock was added to E. faecalis V12-PlyV12 assays to achieve final concentrations of NaCl up to 500 mM in each reaction. NaCl was added to 20, 50, 100, 250 and 500 mM in E. faecalis V12-PlyV12 reactions, with the effects analyzed in a 20 minute OD assay.

Effect of Mouse and Human Blood on PlyV12 Activity

One hundred microliters of purified PlyV12 at 30 units/mL was added to a 100 µL suspension of E. faecalis V12 in the presence of 500 µL of mouse or human heparinized blood. Reactions were incubated at room temperature for 30 minutes, then diluted and plated immediately for bacterial counts.

Effect of E. faecalis V12 Extracted Surface Carbohydrates on PlyV12 Activity

Bacterial surface carbohydrates were extracted using a nitrous acid extraction method (see Example 8 for carbohydrate extraction protocol). Fifty microliters of purified PlyV12 at 4 units/mL was added to 50 µL E. faecalis V12 extracted surface carbohydrates and preincubated for several minutes prior to the addition of a 100 µL suspension. of E. faecalis V12 in PBS. All reactions were incubated at room temperature for 15 minutes, immediately followed by serial dilutions and plating for viability counts. The carbohydrate suspensions were used at 100 mg/mL.

Effect of Cysteine Active Site Inhibitors and a Divalent Cation Chelator on lysin Activities Cysteine active site inhibitors N-ethylmaleimide, iodoacetamide and sodium tetrathionate were added to lytic assays of PlyV12 and E. faecalis V12 at a final concentration of 2 mM, while dithiodipyridine was added at a final concentration of 30 µM due to low solubility. To duplicate reactions, dithiothreitol (DTT) was added to 8 mM, as N-ethylmaleimide is reversible by DTT. EDTA, a chelator of divalent cations, was used at 5 mM. Reactions were monitored by a 15 minute OD assay to determine if these compounds have an effect on PlyV12 lytic activity.

Increasing Expression or Catalytic Activity of PlyV12

Codon Optimization of PlyV12 for Expression in E. coli and Cloning into Multiple Expression Vectors The inability to express PlyV12 to high levels in E. coli was likely due to a difference in the codon usage patterns of the plyV12 ORF and that of E. coli. DNA sequences of plyV12 and other E. faecalis phage lysins were analyzed on the E. coli Codon Usage Analyzer 2.0 program at www.biology.ualberta.ca/pilgrim.hp/links/usage2.0c.html. References were also made to the Codon Usage Database at www.kazusa.or.jp/codon, as well as an article by Kane on rare codon clusters in E. coli (Kane, J. F. 1995. Effects of rare codon clusters on high-level expression of heterologous proteins in Escherichia coli. Curr. Biol. 6:494-500). With an estimated 20% of the plyV12 ORF below the threshold of expression in E. coli, a company named GenScript Corporation (Piscataway, N.J.) was commissioned to custom synthesize the plyV12 gene with codons optimized for expression in E. coli, while preserving the amino acid sequence. The resulting altered gene was named plyV12CO. plyV12CO arrived cloned into pUC18 in the opposite direction with respect to the lac promoter: Attempts at subcloning the gene into plasmid vectors pBAD24 and pBAD18 were made initially. Subsequently, attempts were made at subcloning plyV12CO into the histidine tag fusion vector pBAD/HisB and GST fusion vector pGEX-5X-3. Finally, plyV12CO was cloned into pCC1, a plasmid with tight copy number control, according to manufacturer's instructions. Several resulting pCC1-plyV12CO clones were subsequently transformed into E. coli BL21 (DE3). E. coli BL21/pCC1-plyV12CO were grown at 37° C. for 3 hours, followed by IPTG induction of T7 polymerase for 5 hours. Cell lysates were obtained by chloroform extraction.

Cloning of plyV12 and plyV12CO into a number of Grampositive plasmids were also tried. Attempts were made at cloning the wildtype plyV12 into the streptococcal plasmid pSTOP. Cloning of both the codon optimized and wildtype plyV12 into the E. coli-enterococcal shuttle vector pMSP3535 and an E. coli-B. megaterium shuttle vector pWH1520 were tried.

Mutagenesis of PlyV12 by Passage Through E. coli XL1-Red

The plasmid pBAD24-lysin2 was transformed into E. coli XL1-Red chemically competent cells (Stratagene, La Jolla, Calif.) and selected on 5 LB agar plates containing ampicillin. The resulting colonies on each plate were suspended into a small volume of LB broth, then each suspension was inoculated into 12 mL of LB broth containing ampicillin and grown overnight at 37° C. Plasmid minipreps were carried out on each culture, with the resulting plasmids transformed into chemically competent E. coli XL1-Blue. Several thousand colonies were screened for increased lytic activity against E. faecalis V12 and S. aureus RN6390 using the overlay method. The S. aureus RN6390 overlay consisted of 500 µL of the S. aureus overnight culture and 6 mL BHI soft agar.

Catalytic Domain Switch with PlyG

A fusion protein consisting of the catalytic domain from PlyG (Schuch, R., D. Nelson, and V. A. Fischetti. 2002. A bacteriolytic agent that detects and kills Bacillus anthracis. Nature. 418:884-888), and the binding domain from PlyV12 was constructed. The catalytic domain of both PlyG and PlyV12 are estimated to be contained within the first 150 amino acids (aa). The first 495 bp (165aa) of PlyG and the final 435 bp (145aa) of PlyV12 were linked by an engineered SmaI restriction site with the sequence CCCGGG, which translates into an added proline and glycine residue. Both the wildtype and codon optimized gene versions of the PlyV12 binding domain were used in this experiment. The plyV12 and plyV12CO binding domain were cloned into pBAD24 first using the EcoRI and SmaI sites of BAD24, followed by the plyG catalytic domain using the SmaI and XbaI sites. A number of fusion clones were induced between 30 minutes and 18 hours. Lytic activities of these clones were checked by OD assays.

Example 7

Protein Purification Techniques

Histidine Tagged PlyV12 Purification

Confirmation of expression of histidine tagged PlyV12 was performed by Western blot. Lysates from induced E. coli RosettaBlue/pBAD24-lysin2 and E. coli RosettaBlue/pBAD-6×his-lysin were mixed with an equal volume of SDS sample buffer and boiled for at least 5 minutes, and 45 µL of each sample was subjected to 10% sodium dodecyl sulfate-polyacrylamide gel electrophoresis (SDS-PAGE). The separated proteins were transferred to a polyvinylidene difluoride membrane for Western blot analysis with antibodies directed against the histidine tag (Sambrook, J., E. F. Fritsch, and T. Maniatis. 1989. Molecular cloning: a laboratory manual, 2nd ed. Cold Spring Harbor Laboratory Press, Cold Spring Harbor).

The purification kit sold under the tradename HIS BIND® Purification Kit (Novagen, San Diego Calif.) allows purification of histidine tagged proteins under native or denaturing conditions. Attempts at purifying the histidine tagged PlyV12 expressed from overnight induced *E. coli* RosettaBlue/pBAD-6×his-lysin under native conditions were initially made according to manufacturer's instructions. Subsequently, purification of the protein under native conditions was carried out with decreased imidazole concentrations, lowered from 10 mM to 0 in the binding buffer and halved from 20 to 10 mM in the wash buffer. Using the same kit, protein purification under denaturing conditions in the presence of 8M urea was also attempted.

FPLC purification of the polyhistidine tagged PlyV12 was also attempted using a nickel charged HiTrap Chelating HP 5 mL column (Amersham Biosciences, Piscataway, N.J.) on an FPLC system (AKTA, Amersham Biosciences). Binding of the histidine tagged PlyV12 was carried out in 20 mM sodium phosphate monobasic ($NaH_2PO_4$) buffer. After washing the column with the same buffer, bound proteins were eluted with 20 mM $NaH_2PO_4$ with a linear imidazole gradient up to a concentration of 500 mM. Protein elution was monitored by absorbance at 280 nm.

To ensure that the histidine tag did not interfere with the catalytic function of PlyV12, the tag was removed with enterokinase (EKMaX™; Invitrogen, Carlsbad Calif.).

PlyV12 Purification by Ion Exchange Chromatography

PlyV12 was expressed in *B. megaterium* strain WH320 by induction with IPTG for 1 hour, at which time the culture was centrifuged and lysed with BugBuster. The cell lysate was diluted 1 in 3 in 50 mM morpholineethanesulfonic acid (MES) at pH 6.7 prior to being loaded on three 5 mL HiTrap SP HP columns (Amersham Biosciences) connected in series. The columns were washed with 50 mM MES until the optical density at OD280 reached the baseline. PlyV12 was eluted with a 20 column volume linear gradient to a concentration of 1 M NaCl. An OD280 peak at approximately 330 mM NaCl was found to contain the lytic activity. Purified PlyV12 was concentrated through a 30 kDa cutoff Amicon Ultra filter unit (Millipore).

Example 8

Phage Lysin Binding Epitope Analyses

Extraction of Surface Carbohydrates from *E. faecalis* V12

The surface carbohydrates of *E. faecalis* V12 were extracted using a nitrous acid extraction method (Pancholi, V., and V. A. Fischetti. 1988. Isolation and characterization of the cell-associated region of group A streptococcal M6 protein. J. Bacteriol. 170:2618-2624). One liter of overnight grown bacteria was centrifuged, washed in PBS and suspended in 80 mL PBS. On a rotary shaker in the fume hood, 10 mL 4N sodium nitrite and 10 mL glacial acetic acid were added to the suspension and shaken vigorously for 15 minutes. The mixture was centrifuged at 7,000 g for 15 minutes to remove the bacterial cells. The supernatant containing the extracted carbohydrates was neutralized with sodium hydroxide and dialyzed at 4° C. overnight through a 1 kDa membrane against distilled water. The dialysate was lyophilized to obtain a crude dried carbohydrate preparation. This procedure was scaled up or down where necessary.

Pronase Treatment of *E. faecalis* V12

*E. faecalis* V12 was grown in liquid media for two and a half hours, at which point the culture was divided into two. Pronase was added to one batch to a final concentration of 1 mg/mL, while PBS was added to the other at the same volume and the cultures were allowed to grow for an additional 30 minutes. Bacteria were then washed twice in PBS. *E. faecalis* suspensions were assayed with PlyV12 containing cell lysate. All reactions were monitored by the OD assay for 15 minutes, followed by immediate plating for viability counts.

Periodate Treatment of *E. faecalis* V12

*E. faecalis* V12 was grown in liquid media for 3 hours, centrifuged and suspended in PBS. The suspension was divided equally, and sodium periodate was added to one tube to a final concentration of 10 mM, while PBS was added to the other at the same volume. The reactions were incubated at room temperature for 10 minutes, followed by washing of bacterial cells twice with PBS (Guzman, C. A., C. Pruzzo, M. Plate, M. C. Guardati, and L. Calegari. 1991. Serum dependent expression of *Enterococcus faecalis* adhesins involved in the colonization of heart cells. Microb. Pathog. 11:399-409). *E. faecalis* suspensions were assayed with PlyV12 enzyme. All reactions were monitored by the OD assay for 15 minutes.

Example 9

In Vitro Mouse Models

All mice used were female BALB/c mice ranging between 5 to 8 weeks old (Charles River Laboratories, Inc., Wilmington Mass.).

Gastrointestinal Colonization with *E. faecalis*

For an estimation of endogenous gastrointestinal enterococcal counts, several fecal pellets were collected from each mouse, homogenized in PBS and plated on Enterococcosel™ agar selective for *enterococci*. Water containing 5 mg/mL streptomycin was replaced as the sole water source for mice for 1 week. Streptomycin treatment eliminated the endogenous mouse *enterococci* as none were subsequently detected in the feces. Prior to recolonization of mice with *E. faecalis* V12 resistant to streptomycin (designated strain V12S), water was withheld from mice for 10 hours. A log phase culture of *E. faecalis* V12S was pelleted and suspended in sterile water to $OD_{600}$ of 0.7, which corresponded to approximately 108 colony forming units per milliter (CFU/mL). Mice were placed in fresh bedding and housing. This *E. faecalis* V12S suspension was administered to the mice as the sole fluid supply for 24 hours, after which time, it was replaced with water containing 200 μg/mL streptomycin. In order to administer PlyV12 to mice colonized with *E. faecalis* V12S, water was again withheld from mice for 10 hours. Purified PlyV12 at 30 units/mL was placed as the sole source of fluids in the cage for 20 hours.

*E. faecalis* Septicemia Model

A 3 hour log phase culture of *E. faecalis* V12 was adjusted to $OD_{600}$ of 1, which corresponds to approximately 109 CFU/mL. The culture was then concentrated 10-fold by centrifugation followed by suspension in PBS at 1/10 the original culture volume. Each mouse was injected in its tail vein with *E. faecalis* V12 at an average of $6.5 \times 10^8$ CFU in 100 μL. Septicemia was confirmed by the presence of *enterococci* in blood 48 hours post infection by plating on Enterococcosel™ agar (Gentry-Weeks, C., M. Estay, C. Loui, and D. Baker. 2003. Intravenous mouse infection model for studying the pathology of *Enterococcus faecalis* infections. Infect. Immun. 71:1434-1441). At that time, purified PlyV12 at 30 units/mL, or sterile 50 mM MES at pH 6.7 was injected into the tail vein of each mouse at a volume of either 100 or 200 μL. Blood samples were taken 30 minutes and 6 days post treatment. Blood was collected by performing a retro orbital bleed or cardiac puncture. The mice were anesthetized prior to blood sampling. Eighteen mice were used in the lysin treated group, while 16 mice were used in the buffer treated group.

*E. faecalis* Peritonitis Model

An overnight culture of *E. faecalis* V12 was concentrated 15-fold by centrifugation followed by suspension in PBS at 1/15 the original culture volume. This suspension was injected into the peritoneal cavity of each mouse at $10^9$ CFU per 100 μL, mixed with an equal volume of sterile rat fecal extract (SRFE) (Chenoweth, C. E., K. A. Robinson, and D. R. Schaberg. 1990. Efficacy of ampicillin versus trimethoprim-sulfamethoxazole in a mouse model of lethal enterococcal peritonitis. Antimicrob. Agents Chemother. 34:1800-1802; Gollapudi, S. V. S., A. Gupta, H. Thadepalli, and A. Perez. 1988. Use of lymphokines in treatment of experimental intra-abdominal abcess caused by Bacteroides fragilis. Infect. Immun. 56:2369-2372; Singh, K. V., T. M. Coque, G. M. Weinstock, and B. E. Murray. 1998. In vivo testing of an *Enterococcus faecalis* efaA mutant and use of efaA homologs for species identification. FEMS Immunol. Med. Microbiol. 21:323-331; and Singh, K. V., X. Qin, G. M. Weinstock, and B. E. Murray. 1998. Generation and testing of mutants of *Enterococcus faecalis* in a mouse peritonitis model. J. Infect. Dis. 178:1412-1420). Mice were treated with 200 μL purified PlyV12 at 30 units/mL by injection into the peritoneal cavity 15 minutes after infection, or left untreated. Nine mice were used in each group.

We claim:

1. A therapeutic composition comprising an isolated polypeptide comprising the isolated amino acid sequence of SEQ ID NO:1 the therapeutic composition having killing activity against one or more enterococcal bacteria.

2. The therapeutic composition of claim 1, where the isolated polypeptide is a bacteriophage lysin with lytic killing activity against E. faecalis V12.

3. The therapeutic composition of claim 2, where the bacteriophage lysin has a lytic killing activity against E. faecalis V12 and one or more bacteria selected from the group consisting of: E. faecalis EF-1, E. faecalis EF-17, E. faecalis EFSK-2, E. faecalis EFSK-16, E. faecalis EFSK-33, Streptococcal bacteria is selected from the group consisting of: Streptococcal Group A D471, Streptococcal Group A CS24, Streptococcal Group A CS112, Streptococcal Group A variant A486, Streptococcal Group B NC11237, Streptococcal Group B A349, Streptococcal Group B A909, Streptococcal Group C 2GRP66, Streptococcal Group E K131, Streptococcal Group F F68C, Streptococcal Group G D166B, Streptococcal Group L D167A, Streptococcal Group N C559, S. uberis #45, S. uberis ATCC27958, S. gordonii FS12, S. intermedius PK2821, S. parasanguis PK2564, Staphylococcal S. crista PK1408 and Staphylococcal S. aureus RN6390.

4. The therapeutic composition of claim 1, where the bacteriophage lysin has a lytic killing activity against vancomycin-resistant enterococci bacteria characterized by an average reduction of at least about 50 milliunits of $OD_{600}$ per minute measured by an optical density lytic killing activity assay; where the vancomycin-resistant enterococci bacteria is selected from the group consisting of: E. faecalis EF-1, E. faecalis EF-17, E. faecalis EFSK-2, E. faecalis EFSK-16 and E. faecalis EFSK-33; and
   a. where the optical density lytic killing activity assay is performed by measuring a first $OD_{600}$ of an assay mixture upon forming the assay mixture, and measuring a second $OD_{600}$ of the assay mixture 15 minutes after forming the assay mixture;
   b. where the assay mixture is formed by mixing 100 μL of a bacterial suspension with 100 μL of a bacteriophage lysin solution at a temperature of about 25° ;
   c. where the bacterial suspension comprises mid-logarithmic phase enterococci bacteria in brain heart infusion broth, pelleted and resuspended in PBS at pH of about 7.4 to and $OD_{600}$ of 2.0;
   d. where the bacteriophage lysin solution comprises a preparation of the bacteriophage lysin at 25 lysin activity units/mL in PBS at a pH of about 7.4; and
   e. where the lysin activity unit is the reciprocal of the highest dilution of bacteriophage lysin resulting in a 50% reduction in bacterial $OD_{600}$ in 15 mm.

5. The therapeutic composition of claim 1, where the bacteriophage lysin has a lytic killing activity against Streptococcal bacteria characterized by an average reduction of at least about 50 milliunits of $OD_{600}$ per minute measured by an optical density lytic killing activity assay; where the Streptococcal bacteria is selected from the group consisting of: Group A D471, Group A CS24, Group A CS112, Group A variant A486, Group B NO 11237, Group B A349, Group B A909, Group C 2GRP66, Group E K131, Group F F68C, Group G D166B, Group L D167A, Group N C559, S. uberis #45, S. uberis ATCC27958, S. gordonii FS12, S. intermedius PK2821, and S. parasanguis PK2564; and
   a. where the optical density lytic killing activity assay is performed by measuring a first $OD_{600}$ of an assay mixture upon forming the assay mixture, and measuring a second $OD_{600}$ of the assay mixture 15 minutes after forming the assay mixture;
   b. where the assay mixture is formed by mixing 100 μL of a bacterial suspension with 100 μL of a bacteriophage lysin solution at a temperature of about 25° C.;
   c. where the bacterial suspension comprises mid-logarithmic phase Streptococcal bacteria in brain heart infusion broth, pelleted and resuspended in PBS at pH of about 7.4 to and $OD_{600}$ of 2.0;
   d. where the bacteriophage lysin solution comprises a preparation of the bacteriophage lysin at 25 lysin activity units/mL in PBS at a pH of about 7.4; and
   e. where the lysin activity unit is the reciprocal of the highest dilution of bacteriophage lysin resulting in a 50% reduction in bacterial $OD_{600}$ in 15 mm.

6. The therapeutic composition of claim 1, where the bacteriophage lysin has a lytic killing activity against Staphylococcal bacteria characterized by an average reduction of at least about 50 milliunits of $OD_{600}$ per minute measured by an optical density lytic killing activity assay; where the Staphylococcal bacteria is selected from the group consisting of: S. crista PK1408, and S. aureus RN6390; and
   a. where the optical density lytic killing activity assay is performed by measuring a first $OD_{600}$ of an assay mixture upon forming the assay mixture, and measuring a second $OD_{600}$ of the assay mixture 15 minutes after forming the assay mixture;
   b. where the assay mixture is formed by mixing 100 μL of a bacterial suspension with 100 μL of a bacteriophage lysin solution at a temperature of about 25° C.;
   c. where the bacterial suspension comprises mid-logarithmic phase Staphylococcal bacteria in brain heart infusion broth, pelleted and resuspended in PBS at pH of about 7.4 to and $OD_{600}$ of 2.0;
   d. where the bacteriophage lysin solution comprises a preparation of the bacteriophage lysin at 25 lysin activity units/mL in PBS at a pH of about 7.4; and
   e. where the lysin activity unit is the reciprocal of the highest dilution of bacteriophage lysin resulting in a 50% reduction in bacterial $OD_{600}$ in 15 mm.

7. The therapeutic composition of claim 1, where the isolated polypeptide consists of the isolated amino acid sequence of SEQ ID NO:1.

8. The therapeutic composition of claim 2 where the bacteriophage lysin consists of the amino acid sequence of SEQ ID NO:1.

9. The therapeutic composition of claim 1, further comprising a holin protein.

10. A method of treating an enterococcal bacterial infection, the method comprising the step of administering to a patient having an enterococcal bacterial infection, a therapeutic composition comprising an isolated amino acid sequence comprising the polypeptide of SEQ ID NO:1.

11. The method of claim 10, where the therapeutic composition is administered at a pH of between about 5.0 and about 8.0.

12. The method of claim 11 where the therapeutic composition is administered at a pH of between about 6.0 and about 7.5.

13. The method of claim 10, where the isolated amino acid sequence consists of the polypeptide of SEQ ID NO:1.

14. A method for treating an enterococcal infection comprising the step of administering a composition to a subject comprising at least one bacteriophage lysin comprising at least the amino acid sequence of SEQ ID NO:1 or a polypeptide variant of SEQ ID NO:1 in which one or more amino acid residues are conservatively substituted, where the bacteriophage lysin has a lytic killing activity against E. faecalis V12.

15. The method of claim 14, where the bacteriophage lysin consists of the isolated amino acid of SEQ ID NO:1.

16. The method of claim 14, where the composition is administered at a pH of about 5.0-8.5.

17. The method of claim 14, where the composition is formulated for parenteral administration.

18. The method of claim 14, where the composition further comprises a carrier and is formulated for topical, oral or nasal administration.

19. A therapeutic composition comprising a polypeptide having an amino acid sequence which has at least 95% identity with the amino acid sequence of SEQ ID NO:1, wherein the therapeutic composition has killing activity against one or more enterococcal bacteria.

20. A composition comprising an isolated polypeptide comprising the amino acid sequence of SEQ ID NO:1 the composition having killing activity against one or more enterococcal bacteria.

21. The composition of claim 20, where the isolated polypeptide is a bacteriophage lysin with lytic killing activity against E. faecalis V12.

22. The composition of claim 21, where the bacteriophage lysin has a lytic killing activity against vancomycin-resistant enterococci bacteria characterized by an average reduction of at least about 50 milliunits of $OD_{600}$ per minute measured by an optical density lytic killing activity assay; where the vancomycin-resistant enterococci bacteria is selected from the group consisting of: E. faecalis EF-1, E. faecalis EF-17, E. faecalis EFSK-2, E. faecalis EFSK-16 and E. faecalis EFSK-33; and a. where the optical density lytic killing activity assay is performed by measuring a first OD600 of an assay mixture upon forming the assay mixture, and measuring a second $OD_{600}$ of the assay mixture 15 minutes after forming the assay mixture;

b. where the assay mixture is formed by mixing 100μL of a bacterial suspension with 100μL of a bacteriophage lysin solution at a temperature of about 25° C.;

c. where the bacterial suspension comprises mid-logarithmic phase enterococci bacteria in brain heart infusion broth, pelleted and resuspended in PBS at pH of about 7.4 to and $OD_{600}$ of 2.0;

d. where the bacteriophage lysin solution comprises a preparation of the bacteriophage lysin at 25 lysin activity units/mL in PBS at a pH of about 7.4; and e. where the lysin activity unit is the reciprocal of the highest dilution of bacteriophage lysin resulting in a 50% reduction in bacterial $OD_{600}$ in 15 min.

23. The composition of claim 20 where the bacteriophage lysin has a lytic killing activity against Streptococcal bacteria characterized by an average reduction of at least about 50 milliunits of 0D600 per minute measured by an optical density lytic killing activity assay; where the Streptococcal bacteria is selected from the group consisting of: Group A D471, Group A CS24, Group A CS112, Group A variant A486, Group B NC11237, Group BA349, Group B A909, Group C 2GRP66, Group E K131, Group F F68C, Group G D166B, Group L D167A, Group N C559, S. uberis #45, S. uberis ATCC27958, S. gordonii FS12, S. intermedius PK2821, and S. parasanguis PK2564; and a. where the optical density lytic killing activity assay is performed by measuring a first $OD_{600}$ of an assay mixture upon forming the assay mixture, and measuring a second $OD_{600}$ of the assay mixture 15 minutes after forming the assay mixture;

b. where the assay mixture is formed by mixing 100μL of a bacterial suspension with 100μL of a bacteriophage lysin solution at a temperature of about 25° C.;

c. where the bacterial suspension comprises mid-logarithmic phase Streptococcal bacteria in brain heart infusion broth, pelleted and resuspended in PBS at pH of about 7.4 to and $OD_{600}$ of 2.0;

d. where the bacteriophage lysin solution comprises a preparation of the bacteriophage lysin at 25 lysin activity units/mL in PBS at a pH of about 7.4; and e. where the lysin activity unit is the reciprocal of the highest dilution of bacteriophage lysin resulting in a 50 % reduction in bacterial $OD_{600}$ in 15 min.

24. The composition of claim 20, where the bacteriophage lysin has a lytic killing activity against Staphylococcal bacteria characterized by an average reduction of at least about 50 milliunits of $OD_{600}$ per minute measured by an optical density lytic killing activity assay; where the Staphylococcal bacteria is selected from the group consisting of: S. crista PK1408, and S. aureus RN6390; and a. where the optical density lytic killing activity assay is performed by measuring a first $OD_{600}$ of an assay mixture upon forming the assay mixture, and measuring a second $OD_{600}$ of the assay mixture 15 minutes after forming the assay mixture;

b. where the assay mixture is formed by mixing 100μL of a bacterial suspension with 100μL of a bacteriophage lysin solution at a temperature of about 25° C. ;

c. where the bacterial suspension comprises mid-logarithmic phase Staphylococcal bacteria in brain heart infusion broth, pelleted and resuspended in PBS at pH of about 7.4 to and $OD_{600}$ of 2.0;

d. where the bacteriophage lysin solution comprises a preparation of the bacteriophage lysin at 25 lysin activity units/mL in PBS at a pH of about 7.4; and p1 e. where the lysin activity unit is the reciprocal of the highest dilution of bacteriophage lysin resulting in a 50% reduction in bacterial $OD_{600}$ in 15min.

25. The composition of claim 20, where the isolated polypeptide consists of the isolated amino acid sequence of SEQ ID NO:1.

26. The composition of claim 21 where the bacteriophage lysin consists of the amino acid sequence of SEQ ID NO:1.

27. The composition of claim 20, further comprising a holin protein.

\* \* \* \* \*